US011236311B2

(12) United States Patent
Miller et al.

(10) Patent No.: US 11,236,311 B2
(45) Date of Patent: *Feb. 1, 2022

(54) T7 RNA POLYMERASE VARIANTS

(71) Applicant: Codexis, Inc., Redwood City, CA (US)

(72) Inventors: Mathew G. Miller, San Carlos, CA (US); Chinping Chng, Menlo Park, CA (US); Oscar Alvizo, Fremont, CA (US); Melissa Ann Mayo, Foster City, CA (US); James Nicholas Riggins, San Francisco, CA (US); Xiang Yi, Foster City, CA (US); Jonathan S. Penfield, Truckee, CA (US); Gjalt W. Huisman, Redwood City, CA (US); Jared Davis, Cheshire, CT (US); Yasushi Saotome, Solana Beach, CA (US)

(73) Assignee: Codexis, Inc., Redwood City, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/938,793

(22) Filed: Jul. 24, 2020

(65) Prior Publication Data

US 2020/0354698 A1 Nov. 12, 2020

Related U.S. Application Data

(62) Division of application No. 16/012,462, filed on Jun. 19, 2018, now Pat. No. 10,738,286.

(60) Provisional application No. 62/527,740, filed on Jun. 30, 2017, provisional application No. 62/528,840, filed on Jul. 5, 2017.

(51) Int. Cl.
| | |
|---|---|
| *C12N 9/12* | (2006.01) |
| *C12N 1/20* | (2006.01) |
| *C12N 15/00* | (2006.01) |
| *C12P 19/34* | (2006.01) |

(52) U.S. Cl.
CPC ........... *C12N 9/1247* (2013.01); *C12N 15/00* (2013.01); *C12Y 207/07006* (2013.01); *C12P 19/34* (2013.01)

(58) Field of Classification Search
CPC .................................................. C12N 9/1247
See application file for complete search history.

(56) References Cited

U.S. PATENT DOCUMENTS

| | | | |
|---|---|---|---|
| 4,795,699 A | 1/1989 | Tabor et al. |
| 4,921,794 A | 5/1990 | Tabor et al. |
| 4,942,130 A | 7/1990 | Tabor et al. |
| 4,946,786 A | 8/1990 | Tabor et al. |
| 4,952,496 A | 8/1990 | Studier et al. |
| 4,994,372 A | 2/1991 | Tabor et al. |
| 5,145,776 A | 9/1992 | Tabor et al. |
| 5,173,411 A | 12/1992 | Tabor et al. |
| 5,266,466 A | 11/1993 | Tabor et al. |
| 5,605,793 A | 2/1997 | Stemmer |
| 5,811,238 A | 9/1998 | Stemmer et al. |
| 5,830,721 A | 11/1998 | Stemmer et al. |
| 5,834,252 A | 11/1998 | Stemmer et al. |
| 5,837,458 A | 11/1998 | Minshull et al. |
| 5,928,905 A | 7/1999 | Stemmer et al. |
| 6,096,548 A | 8/2000 | Stemmer |
| 6,117,679 A | 9/2000 | Stemmer |
| 6,132,970 A | 10/2000 | Stemmer |
| 6,165,793 A | 12/2000 | Stemmer |
| 6,180,406 B1 | 1/2001 | Stemmer |
| 6,251,674 B1 | 6/2001 | Tobin et al. |
| 6,277,638 B1 | 8/2001 | Stemmer |
| 6,287,861 B1 | 9/2001 | Stemmer et al. |
| 6,287,862 B1 | 9/2001 | delCardayre et al. |
| 6,291,242 B1 | 9/2001 | Stemmer |
| 6,297,053 B1 | 10/2001 | Stemmer |
| 6,303,344 B1 | 10/2001 | Patten et al. |
| 6,309,883 B1 | 10/2001 | Minshull et al. |
| 6,319,713 B1 | 11/2001 | Patten et al. |
| 6,319,714 B1 | 11/2001 | Crameri et al. |
| 6,323,030 B1 | 11/2001 | Stemmer |
| 6,326,174 B1 | 12/2001 | Joyce et al. |
| 6,326,204 B1 | 12/2001 | delCardayre et al. |
| 6,335,160 B1 | 1/2002 | Patten et al. |
| 6,335,198 B1 | 1/2002 | delCardayre et al. |
| 6,344,356 B1 | 2/2002 | Stemmer |
| 6,352,859 B1 | 3/2002 | delCardayre et al. |

(Continued)

FOREIGN PATENT DOCUMENTS

| | | |
|---|---|---|
| EP | 2316934 A1 | 5/2011 |
| EP | 2377938 A1 | 10/2011 |

(Continued)

OTHER PUBLICATIONS

Straney, D.C., et al., "A stressed intermediate in the formation of stably initiated RNA chains at the *Escherichia coli* lac UV5 promoter," J. Mol. Biol., 193:267-78 [1987].

(Continued)

*Primary Examiner* — Yong D Pak
(74) *Attorney, Agent, or Firm* — Codexis, Inc.

(57) ABSTRACT

The present invention provides engineered RNA polymerase variants and compositions comprising these variants. The present invention further provides engineered T7 RNA polymerase variants and compositions comprising these variants. These variants have been evolved for selective incorporation of the m7G(5')ppp(5')m7G cap analog over GTP at the initiation of in vitro transcription. The present invention also provides methods for selective capping of RNA transcripts.

25 Claims, 1 Drawing Sheet
Specification includes a Sequence Listing.

(56) References Cited

U.S. PATENT DOCUMENTS

| | | |
|---|---|---|
| 6,355,484 B1 | 3/2002 | Patten et al. |
| 6,358,740 B1 | 3/2002 | Patten et al. |
| 6,358,742 B1 | 3/2002 | Stemmer |
| 6,365,377 B1 | 4/2002 | Patten et al. |
| 6,365,408 B1 | 4/2002 | Stemmer |
| 6,368,861 B1 | 4/2002 | Crameri et al. |
| 6,372,497 B1 | 4/2002 | Stemmer |
| 6,376,246 B1 | 4/2002 | Crameri et al. |
| 6,379,964 B1 | 4/2002 | delCardayre et al. |
| 6,387,702 B1 | 5/2002 | Stemmer |
| 6,391,552 B2 | 5/2002 | Stemmer |
| 6,391,640 B1 | 5/2002 | Minshull et al. |
| 6,395,547 B1 | 5/2002 | Stemmer |
| 6,406,855 B1 | 6/2002 | Patten et al. |
| 6,406,910 B1 | 6/2002 | Patten et al. |
| 6,413,745 B1 | 7/2002 | Patten et al. |
| 6,413,774 B1 | 7/2002 | Stemmer |
| 6,420,175 B1 | 7/2002 | Stemmer |
| 6,423,542 B1 | 7/2002 | Crameri et al. |
| 6,426,224 B1 | 7/2002 | Crameri et al. |
| 6,436,675 B1 | 8/2002 | Welch et al. |
| 6,444,468 B1 | 9/2002 | Stemmer et al. |
| 6,455,253 B1 | 9/2002 | Patten et al. |
| 6,479,652 B1 | 11/2002 | Crameri et al. |
| 6,482,647 B1 | 11/2002 | Stemmer |
| 6,489,146 B2 | 12/2002 | Stemmer et al. |
| 6,506,602 B1 | 1/2003 | Stemmer |
| 6,506,603 B1 | 1/2003 | Stemmer |
| 6,519,065 B1 | 2/2003 | Colbourne et al. |
| 6,521,453 B1 | 2/2003 | Crameri et al. |
| 6,528,311 B1 | 3/2003 | delCardayre et al. |
| 6,537,746 B2 | 3/2003 | Arnold et al. |
| 6,573,098 B1 | 6/2003 | Stemmer |
| 6,576,467 B1 | 6/2003 | Stemmer |
| 6,579,678 B1 | 6/2003 | Patten et al. |
| 6,586,182 B1 | 7/2003 | Patten et al. |
| 6,602,986 B1 | 8/2003 | Stemmer et al. |
| 6,613,514 B2 | 9/2003 | Patten et al. |
| 6,653,072 B1 | 11/2003 | Patten et al. |
| 6,716,631 B1 | 4/2004 | delCardayre et al. |
| 6,777,218 B1 | 8/2004 | Mikkelsen et al. |
| 6,867,027 B1 | 3/2005 | Hayashizaki et al. |
| 6,917,882 B2 | 7/2005 | Selfinov et al. |
| 6,946,296 B2 | 9/2005 | Patten et al. |
| 6,961,664 B2 | 11/2005 | Selfinov et al. |
| 6,995,017 B1 | 2/2006 | Stemmer |
| 7,024,312 B1 | 4/2006 | Selfinov et al. |
| 7,058,515 B1 | 6/2006 | Selfinov et al. |
| 7,105,297 B2 | 9/2006 | Minshull et al. |
| 7,141,665 B1 | 11/2006 | Joyce et al. |
| 7,148,054 B2 | 12/2006 | delCardayre et al. |
| 7,288,375 B2 | 10/2007 | Stemmer et al. |
| 7,335,471 B2 | 2/2008 | Guillerez et al. |
| 7,421,347 B2 | 9/2008 | Selfinov et al. |
| 7,430,477 B2 | 9/2008 | Selfinov et al. |
| 7,507,567 B2 | 3/2009 | Sugiyama et al. |
| 7,534,564 B2 | 5/2009 | Patten et al. |
| 7,620,500 B2 | 11/2009 | Mundorff et al. |
| 7,620,502 B2 | 11/2009 | Selfinov et al. |
| 7,629,157 B2 | 12/2009 | Davis et al. |
| 7,629,170 B2 | 12/2009 | delCardayre et al. |
| 7,702,464 B1 | 4/2010 | Emig et al. |
| 7,747,391 B2 | 6/2010 | Gustafsson et al. |
| 7,747,393 B2 | 6/2010 | Fox |
| 7,751,986 B2 | 7/2010 | Gustafsson et al. |
| 7,776,598 B2 | 8/2010 | Patten et al. |
| 7,783,428 B2 | 8/2010 | Gustafsson et al. |
| 7,795,030 B2 | 9/2010 | Minshull et al. |
| 7,807,817 B2 | 10/2010 | Joyce et al. |
| 7,853,410 B2 | 12/2010 | Selfinov et al. |
| 7,868,138 B2 | 1/2011 | Stemmer et al. |
| 7,873,477 B1 | 1/2011 | Gustafsson et al. |
| 7,873,499 B2 | 1/2011 | Selfinov et al. |
| 7,904,249 B2 | 3/2011 | Selfinov et al. |
| 7,957,912 B2 | 6/2011 | Selfinov et al. |
| 8,014,961 B2 | 9/2011 | Bass et al. |
| 8,029,988 B2 | 10/2011 | Crameri et al. |
| 8,058,001 B2 | 11/2011 | Crameri et al. |
| 8,076,138 B2 | 12/2011 | delCardayre et al. |
| 8,101,385 B2 | 1/2012 | Cload et al. |
| 8,105,813 B2 | 1/2012 | Diener et al. |
| 8,170,806 B2 | 5/2012 | Selfinov et al. |
| 8,377,681 B2 | 2/2013 | delCardayre et al. |
| 8,383,346 B2 | 2/2013 | Colbeck et al. |
| 8,457,903 B1 | 6/2013 | Emig et al. |
| 8,481,685 B2 | 7/2013 | Bourn et al. |
| 8,504,498 B2 | 8/2013 | Fox |
| 8,551,752 B2 | 10/2013 | Oe et al. |
| 8,589,085 B2 | 11/2013 | Selfinov et al. |
| 8,762,066 B2 | 6/2014 | Fox |
| 8,768,871 B2 | 7/2014 | Fox |
| 8,836,348 B2 | 9/2014 | Iwasawa et al. |
| 8,846,348 B2 | 9/2014 | Jendrisak et al. |
| 8,849,575 B2 | 9/2014 | Gustafsson et al. |
| 9,005,930 B2 | 4/2015 | Jendrisak et al. |
| 9,023,633 B2 | 5/2015 | Faurholm et al. |
| 9,062,292 B2 | 6/2015 | Coleman |
| 9,115,380 B2 | 8/2015 | Jendrisak et al. |
| 9,163,246 B2 | 10/2015 | Barnes |
| 9,193,959 B2 | 11/2015 | Sobek et al. |
| 9,260,703 B2 | 2/2016 | Eberwine et al. |
| 9,447,388 B2 | 9/2016 | Ishino et al. |
| 9,499,811 B2 | 11/2016 | Kucera et al. |
| 9,540,671 B2 | 1/2017 | Jais |
| 9,593,326 B2 | 3/2017 | Clark et al. |
| 9,665,694 B2 | 5/2017 | Cope |
| 9,822,348 B2 | 11/2017 | Anton et al. |
| 10,000,772 B2 | 6/2018 | Doudna et al. |
| 10,793,841 B2 * | 10/2020 | Miller ............ C12Y 207/07006 |
| 2008/0220990 A1 | 9/2008 | Fox |
| 2009/0312196 A1 | 12/2009 | Colbeck et al. |
| 2012/0252071 A1 | 10/2012 | Greif et al. |
| 2013/0224793 A1 | 8/2013 | Martin et al. |
| 2014/0005057 A1 | 1/2014 | Clark et al. |
| 2014/0214391 A1 | 7/2014 | Cope |
| 2014/0221216 A1 | 8/2014 | Cope et al. |
| 2014/0363875 A1 | 12/2014 | Ishino et al. |
| 2015/0050658 A1 | 2/2015 | Cho |
| 2015/0133307 A1 | 5/2015 | Zhang et al. |
| 2015/0134315 A1 | 5/2015 | Sarmiento et al. |
| 2016/0002647 A1 | 1/2016 | Dunham et al. |
| 2016/0010069 A1 | 1/2016 | Greif et al. |
| 2016/0024547 A1 | 1/2016 | Bancel et al. |
| 2016/0032260 A1 | 2/2016 | Sobek et al. |
| 2016/0168558 A1 | 6/2016 | Eberwine et al. |
| 2016/0244787 A1 | 8/2016 | Chan et al. |

FOREIGN PATENT DOCUMENTS

| | | |
|---|---|---|
| JP | 2011051943 A | 3/2011 |
| WO | 95/22625 A1 | 8/1995 |
| WO | 96/00787 A1 | 1/1996 |
| WO | 97/0078 A1 | 1/1997 |
| WO | 97/35966 A1 | 10/1997 |
| WO | 98/27230 A1 | 6/1998 |
| WO | 00/42651 A1 | 7/2000 |
| WO | 01/75767 A2 | 10/2001 |
| WO | 2006/004648 A1 | 1/2006 |
| WO | 2008/078180 A2 | 7/2008 |
| WO | 2009/021191 A2 | 2/2009 |
| WO | 2009/113718 A1 | 9/2009 |
| WO | 2009/152336 A1 | 12/2009 |
| WO | 2010/144103 A1 | 12/2010 |
| WO | 2015/143318 A1 | 9/2015 |
| WO | 2017/139412 A1 | 8/2017 |
| WO | 2018/011067 A2 | 1/2018 |
| WO | 2019/005540 A1 | 1/2019 |

OTHER PUBLICATIONS

Studier, F.W., et al., "Use of bacteriophage T7 RNA polymerase to direct selective high-level expression of cloned genes," J. Mol. Biol., 189:113-130 [1986].

(56) References Cited

OTHER PUBLICATIONS

Tahirov, T.H., et al., "Structure of a T7 RNA polymerase elongation complex at 2.9 Å resolution," Nature, 420:43-50 [2002].
Temiakov, D., et al., "The specificity loop of T7 RNA polymerase interacts first with the promoter and then with the elongating transcript, suggesting a mechanism for promoter clearance ," Proc. Natl. Acad. Sci. USA, 97(26): 14109-14 [2000].
Wells, J.A., et al., "Cassette mutagenesis: an efficient method for generation of multiple mutations at defined sites," Gene, 34:315-323 (1985).
Wilson, R.H., et al., "Engineered DNA ligases with improved activities in vitro," Prot. Engin. Des. Select., 26(7):471-478 [2013].
Yamagami, T., et al., "Mutant Taq DNA polymerases with improved elongation ability as a useful reagent for genetic engineering," Frontiers in Microbiology, 5(Article 461): 1-10 [2014].
Yin, Y.W., et al., "Structural Basis for the Transition from Initiation to Elongation Transcription in T7 RNA Polymerase," Science, 298(5597): 1387-95 [2002].
Young, B.A., et al., "Views of Transcription Initiation," Cell, 109(4):417-20 [2002].
Zhang, J-H., et al., "Directed evolution of a fucosidase from a galactosidase by DNA shuffling and screening ," Proc. Nat. Acad. Sci., U.S.A., 94:4504-4509 (1997).
Zhao, H., et al., "Molecular evolution by staggered extension process (StEP) in vitro recombination," Nat. Biotechnol., 16:258-261 (1998).
Julius, C., et al., "Bacterial RNA polymerase caps RNA with various cofactors and cell wall precursors," Nucleic Acids Research, 45(14):8282-8290 [2017].
Park, W., et al., "Over-expression of recombinant proteins with N-terminal His-tag via subcellular uneven distribution in *Escherichia coli*," Acta Biochimica et Biophysica Sinica, 47(7):488-495 [2015].
Bonner, G., et al., "The thumb subdomain of T7 RNA polymerase functions to stabilize the ternary complex during processive transcription," J. Biol. Chem., 269: 25129-36 [1994].
Studer, R.A., et al., "Residue mutations and their impact on protein structure and function: detecting beneficial and pathogenic changes," Biochem. J., 449:581 594 [2013].
Altschul, S., et al., "Basic local alignment search tool," J. Mol. Biol., 215: 403-410 (1990).
Altschul, S.F., et al., "Gapped BLAST and PSI-BLAST: a new generation of protein database search programs," Nucleic Acids Res., 25(17):3389-3402 (1997).
Bandwar, R.P., et al., "Sequential Release of Promoter Contacts during Transcription Initiation to Elongation Transition," J. Mol. Biol., 360(2):466-83 [2006].
Beaucage, S.L., et al., "Deoxynucleoside phosphoamidites—A new class of key intermediates for deoxypolynucleotide synthesis," Tetrahedron Letters, 22(20):1859-62 (1981).
Black, M.E., et al., "Creation of drug-specific herpes simplex virus type 1 thymidine kinase mutants for gene therapy," Proc Natl Acad Sci USA, 93:3525-3529 (1996).
Botstein, D., et al., "Strategies and applications of in vitro mutagenesis," Science, 229(4719):1193-1201, 1985.
Caldwell, R.C., et al., "Mutagenic PCR," PCR Methods Appl., 3:S136-S140 [1994].
Carpousis, A.J., et al., "Interaction of RNA polymerase with lacUV5 promoter DNA during mRNA initiation and elongation: Footprinting, methylation, and rifampicin-sensitivity changes accompanying transcription initiation," J. Mol. Biol., 183(2): 165-77 [1985].
Carter, P., "Site-directed mutagenesis," Biochem. J., 237:1-7 (1986).
Cheetham, G.M.T., et al., "Structure of a Transcribing T7 RNA Polymerase Initiation Complex," Science, 286(5448):2305-9 [1999].
Cheetham, G.M.T., et al., "Transcription Regulation, Initiation, and "DNA Scrunching" by T7 RNA Polymerase," Cold Spring Harb. Symp Quant. Biol., 63:263-8 [1998].
Cheetham, G.M.T., et al., "Structural basis for initiation of transcription from an RNA polymerase-promoter complex," Nature, 399:80-83 [1999].

Christians, F.C., et al., "Directed evolution of thymidine kinase for AZT phosphorylation using DNA family shuffling," Nat. Biotechnol., 17:259-264 (1999).
Crameri, A., et al., "DNA shuffling of a family of genes from diverse species accelerates directed evolution", Nature, 391:288-291 (1998).
Crameri, A., et al., "Improved green fluorescent protein by molecular evolution using DNA shuffling," Nat. Biotechnol., 14(3):315-319 (1996).
Crameri, A., et al., "Molecular evolution of an arsenate detoxification pathway by DNA shuffling," Nat. Biotechnol., 15(5):436-438 (1997).
Dale, S.J., et al., "Oligonucleotide-directed random mutagenesis using the phosphorothioate method," Methods Mol. Biol., 57:369-74 (1996).
Esposito, E.A., et al., "Cross-linking of Promoter DNA to T7 RNA Polymerase Does Not Prevent Formation of a Stable Elongation Complex," J. Biol. Chem., 279:44270-6 [2004].
Furuichi, Y., et al., "5'-Terminal structure and mRNA stability," Nature, 266:235-9 [1977].
Greenough, L., et al., "Adapting capillary gel electrophoresis as a sensitive, high-throughput method to accelerate characterization of nucleic acid metabolic enzymes," Nuc. Acids Res., 44(2): e15, pp. 1-11 [2016].
Grudzien, E., et al., "Novel cap analogs for in vitro synthesis of mRNAs with high translational efficiency," RNA, 10:1479-87 [2004].
Guo, Q., et al., "Multiple Roles for the T7 Promoter Nontemplate Strand during Transcription Initiation and Polymerase Release," J. Biol. Chem., 280:3474-82 [2005].
Guo, Z., et al., "3'-End-Forming Signals of Yeast mRNA," Mol. Cell. Biol., 15(11):5983-5990 [1995].
Henikoff, S., et al., "Amino acid substitution matrices from protein blocks," Proc. Natl. Acad. Sci. USA, 89:10915-10919 [1992].
Hieb, A.R., et al., "An 8 nt RNA triggers a rate-limiting shift of RNA polymerase II complexes into elongation," EMBO J., 25:3100-09 [2006].
Hsu, L.M., "Promoter clearance and escape in prokaryotes," Biochim. Biophys. Acta, 1577:191-207 [2002].
Huang, J., et al., "Misincorporation by Wild-Type and Mutant T7 RNA Polymerases: Identification of Interactions That Reduce Misincorporation Rates by Stabilizing the Catalytically Incompetent Open Conformation," Biochem., 39(38):11571-11580 [2000].
Ikeda, R.A., et al., "Interactions of a proteolytically nicked RNA polymerase of bacteriophage T7 with its promoter," J. Biol. Chem., 262(8):3800-8 [1987].
Ikeda, R.A., et al., "Interactions of the RNA polymerase of bacteriophage T7 with its promoter during binding and initiation of transcription," Proc. Natl. Acad Sci. USA, 83(11):3614-8 [1986].
Kennedy, W.P., et al., "Mechanism for De Novo RNA Synthesis and Initiating Nucleotide Specificity by T7 RNA Polymerase," J. Mol. Biol., 370(2):256-68 [2007].
Kinsella, L., et al., "RNA polymerase: correlation between transcript length abortive product synthesis and formation of a stable ternary complex," Biochem., 21(11):2719-23 [1982].
Kramer, B., et al., "Different base/base mismatches are corrected with different efficiencies by the methyl-directed DNA mismatch-repair system of *E. coli*," Cell, 38(3):879-887, 1984.
Krummel, B., et al., "RNA chain initiation by *Escherichia coli* RNA polymerase. Structural transitions of the enzyme in early ternary complexes," Biochem., 28(19):7829-7842 [1989].
Lewis, J.D., et al., "The Role of the Cap Structure in RNA Processing and Nuclear Export," Eur. J. Biochem., 247:461-9 [1997].
Ling, M.M., et al., "Approaches to DNA Mutagenesis: An Overview," Anal. Biochem., 254(2):157-78 [1997].
Ma, K., et al., "Major Conformational Changes Occur during the Transition from an Initiation Complex to an Elongation Complex by T7 RNA Polymerase ," J. Biol. Chem., 277(45):43206-15 [2002].
Mao, X., et al., "Intrinsic RNA (guanine-7) methyltransferase activity of the vaccinia virus capping enzyme D1 subunit is stimulated by the D12 subunit. Identification of amino acid residues in the D1 protein required for subunit association and methyl group transfer," J. Biol. Chem., 269(39):24472-9 [1994].

(56) References Cited

OTHER PUBLICATIONS

Matthes, H.W.D., et al., "Simultaneous rapid chemical synthesis of over one hundred oligonucleotides on a microscale," EMBO J., 3(4):801-05 (1984).

Minshull, J., et al., "Protein evolution by molecular breeding," Curr. Op. Chem. Biol., 3(3):284-290 (1999).

Mukherjee, S., et al., "Structural Transitions Mediating Transcription Initiation by T7 RNA Polymerase," Cell, 110:81-91 [2002].

Needleman, S., et al., "A general method applicable to the search for similarities in the amino acid sequence of two proteins," J. Mol. Biol. 48:443-453 (1970).

Nielsen, D.A., et al., "Preparation of capped RNA transcripts using T7 RNA polymerase," Nucl. Acids Res., 14(14):5936 [1986].

Pearson, W.R., "Improved tools for biological sequence comparison," Proc. Nat'l. Acad. Sci. USA, 85:2444-2448(1988).

Peng, Z., et al., "Synthesis and Application of a Chain-Terminating Dinucleotide mRNA Cap Analog," Org. Lett., 4(2):161-164 [2002].

Romanos, M.A., et al., "Foreign gene expression in yeast: a review," Yeast 8:423-488 [1992].

Smith, M., "In vitro mutagenesis," Ann. Rev. Genet., 19:423-462 (1985).

Smith, T., et al., "Comparison of Biosequences," Adv. Appl. Math, 2:482-489 (1981).

Sousa, R., et al., "T7 RNA Polymerase," Prog. Nucl. Acid Res. Mol. Biol., 73:1-41 [2003].

Stemmer, W., "DNA Shuffling by Random Fragmentation and Reassembly: In vitro Recombination for Molecular Evolution," Proc. Natl. Acad. Sci. USA, 91:10747-10751 (1994).

Stemmer, W.P.C., "Rapid evolution of a protein in vitro by DNA shuffling", Nature, 370:389-391 (1994).

European Search Report for EP18824385.1, dated Mar. 22, 2021.

European Search Report for EP application No. EP18824479.2, dated Mar. 4, 2021.

\* cited by examiner

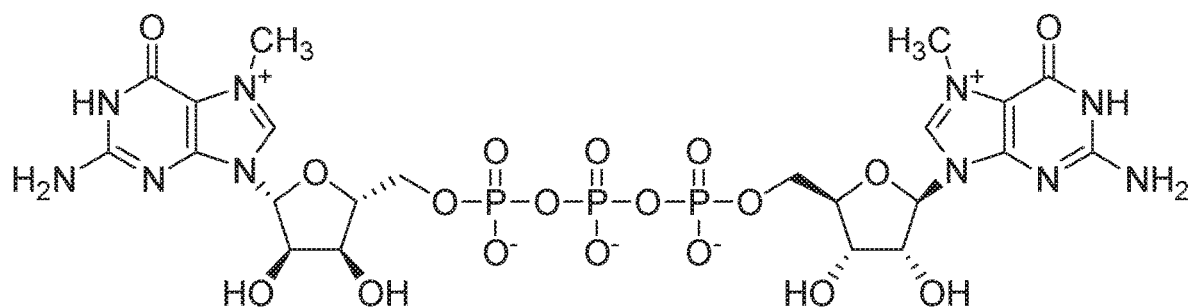

SEQUENCE LISTING

<160> NUMBER OF SEQ ID NOS: 40

<210> SEQ ID NO 1
<211> LENGTH: 2649
<212> TYPE: DNA
<213> ORGANISM: Artificial Sequence
<220> FEATURE:
<223> OTHER INFORMATION: T7RNAP Wild Type

<400> SEQUENCE: 1

```
atgaacacga ttaacatcgc taagaacgac ttctctgaca tcgaactggc tgctatcccg      60
ttcaacactc tggctgacca ttacggtgag cgtttagctc gcgaacagtt ggcccttgag     120
catgagtctt acgagatggg tgaagcacgc ttccgcaaga tgtttgagcg tcaacttaaa     180
gctggtgagg ttgcggataa cgctgccgcc aagcctctca tcactaccct actccctaag     240
atgattgcac gcatcaacga ctggtttgag gaagtgaaag ctaagcgcgg caagcgcccg     300
acagccttcc agttcctgca agaaatcaag ccggaagcca tagcgtacat caccattaag     360
accactctgg cttgcctaac cagtgctgac aatacaaccg ttcaggctgt agcaagcgca     420
atcggtcggg ccattgagga cgaggctcgc ttcggtcgta tccgtgacct tgaagctaag     480
cacttcaaga aaacgttga ggaacaactc aacaagcgcg tagggcacgt ctacaagaaa     540
gcatttatgc aagttgtcga ggctgacatg ctctctaagg gtctactcgg tggcgaggcg     600
tggtcttcgt ggcataagga agactctatt catgtaggag tacgctgcat cgagatgctc     660
attgagtcaa ccggaatggt tagcttacac cgccaaaatg ctggcgtagt aggtcaagac     720
tctgagacta tcgaactcgc acctgaatac gctgaggcta tcgcaacccg tgcaggtgcg     780
ctggctggca tctctccgat gttccaacct tgcgtagttc ctcctaagcc gtggactggc     840
attactggtg gtggctattg ggctaacggt cgtcgtcctc tggcgctggt gcgtactcac     900
agtaagaaag cactgatgcg ctacgaagac gtttacatgc ctgaggtgta caaagcgatt     960
aacattgcgc aaaacaccgc atggaaaatc aacaagaaag tcctagcggt cgccaacgta    1020
atcaccaagt ggaagcattg tccggtcgag gacatccctg cgattgagcg tgaagaactc    1080
ccgatgaaac cggaagacat cgacatgaat cctgaggctc tcaccgcgtg gaaacgtgct    1140
gccgctgctg tgtaccgcaa ggacaaggct cgcaagtctc gccgtatcag ccttgagttc    1200
atgcttgagc aagccaataa gtttgctaac cataaggcca tctggttccc ttacaacatg    1260
gactggcgcg gtcgtgttta cgctgtgtca atgttcaacc cgcaaggtaa cgatatgacc    1320
aaaggactgc ttacgctggc gaaagtaaa ccaatcggta aggaagttta ctactggctg    1380
aaaatccacg gtgcaaactg tgcgggtgtc gataaggttc cgttccctga gcgcatcaag    1440
ttcattgagg aaaaccacga gaacatcatg gcttgcgcta gtctccact ggagaacact    1500 tggtgggctg agcaagattc tccgttctgc ttccttgcgt tctgctttga gtacgctggg    1560
gtacagcacc acggcctgag ctataactgc tcccttccgc tggcgtttga cgggtcttgc    1620
tctggcatcc agcacttctc cgcgatgctc cgagatgagg taggtggtcg cgcggttaac    1680
ttgcttccta gtgaaaccgt tcaggacatc tacgggattg ttgctaagaa agtcaacgag    1740
attctacaag cagacgcaat caatgggacc gataacgaag tagttaccgt gaccgatgag    1800
aacactggtg aaatctctga gaaagtcaag ctgggcacta aggcactggc tggtcaatgg    1860
```

```
ctggcttacg gtgttactcg cagtgtgact aagcgttcag tcatgacgct ggcttacggg    1920
tccaaagagt tcggcttccg tcaacaagtg ctggaagata ccattcagcc agctattgat    1980
tccggcaagg gtctgatgtt cactcagccg aatcaggctg ctggatacat ggctaagctg    2040
atttgggaat ctgtgagcgt gacggtggta gctgcggttg aagcaatgaa ctggcttaag    2100
tctgctgcta agctgctggc tgctgaggtc aaagataaga agactggaga gattcttcgc    2160
aagcgttgcg ctgtgcattg ggtaactcct gatggtttcc ctgtgtggca ggaatacaag    2220
aagcctattc agacgcgctt gaacctgatg ttcctcggtc agttccgctt acagcctacc    2280
attaacacca caaagatag cgagattgat gcacacaaac aggagtctgg tatcgctcct    2340
aactttgtac acagccaaga cggtagccac cttcgtaaga ctgtagtgtg gcacacgag    2400 aagtacggaa tcgaatcttt tgcactgatt cacgactcct tcggtaccat tccggctgac    2460
gctgcgaacc tgttcaaagc agtgcgcgaa actatggttg acacatatga gtcttgtgat    2520
gtactggctg atttctacga ccagttcgct gaccagttgc acgagtctca attggacaaa    2580
atgccagcac ttccggctaa aggtaacttg aacctccgtg acatcttaga gtcggacttc    2640
gcgttcgcg                                                             2649

<210> SEQ ID NO 2
<211> LENGTH: 883
<212> TYPE: PRT
<213> ORGANISM: Artificial Sequence
<220> FEATURE:
<223> OTHER INFORMATION: T7RNAP Wild Type

<400> SEQUENCE: 2

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
```

```
            210                 215                 220
Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Tyr Trp Ala
        275                 280                 285

Asn Gly Arg Arg Pro Leu Ala Leu Val Arg Thr His Ser Lys Lys Ala
        290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Leu Pro Met Lys Pro Glu Asp Ile Asp
        355                 360                 365

Met Asn Pro Glu Ala Leu Thr Ala Trp Lys Arg Ala Ala Ala Val
370                 375                 380

Tyr Arg Lys Asp Lys Ala Arg Lys Ser Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
        435                 440                 445

Gly Lys Pro Ile Gly Lys Glu Gly Tyr Tyr Trp Leu Lys Ile His Gly
        450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
        515                 520                 525

Asn Cys Ser Leu Pro Leu Ala Phe Asp Gly Ser Cys Ser Gly Ile Gln
        530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
        595                 600                 605

Val Lys Leu Gly Thr Lys Ala Leu Ala Gly Gln Trp Leu Ala Tyr Gly
        610                 615                 620

Val Thr Arg Ser Val Thr Lys Arg Ser Val Met Thr Leu Ala Tyr Gly
625                 630                 635                 640
```

```
Ser Lys Glu Phe Gly Phe Arg Gln Gln Val Leu Glu Asp Thr Ile Gln
                645                 650                 655
Pro Ala Ile Asp Ser Gly Lys Gly Leu Met Phe Thr Gln Pro Asn Gln
            660                 665                 670
Ala Ala Gly Tyr Met Ala Lys Leu Ile Trp Glu Ser Val Ser Val Thr
        675                 680                 685
Val Val Ala Ala Val Glu Ala Met Asn Trp Leu Lys Ser Ala Ala Lys
    690                 695                 700
Leu Leu Ala Ala Glu Val Lys Asp Lys Lys Thr Gly Glu Ile Leu Arg
705                 710                 715                 720
Lys Arg Cys Ala Val His Trp Val Thr Pro Asp Gly Phe Pro Val Trp
                725                 730                 735
Gln Glu Tyr Lys Lys Pro Ile Gln Thr Arg Leu Asn Leu Met Phe Leu
            740                 745                 750
Gly Gln Phe Arg Leu Gln Pro Thr Ile Asn Thr Asn Lys Asp Ser Glu
        755                 760                 765
Ile Asp Ala His Lys Gln Glu Ser Gly Ile Ala Pro Asn Phe Val His
    770                 775                 780
Ser Gln Asp Gly Ser His Leu Arg Lys Thr Val Val Trp Ala His Glu
785                 790                 795                 800
Lys Tyr Gly Ile Glu Ser Phe Ala Leu Ile His Asp Ser Phe Gly Thr
                805                 810                 815
Ile Pro Ala Asp Ala Ala Asn Leu Phe Lys Ala Val Arg Glu Thr Met
            820                 825                 830
Val Asp Thr Tyr Glu Ser Cys Asp Val Leu Ala Asp Phe Tyr Asp Gln
        835                 840                 845
Phe Ala Asp Gln Leu His Glu Ser Gln Leu Asp Lys Met Pro Ala Leu
    850                 855                 860
Pro Ala Lys Gly Asn Leu Asn Leu Arg Asp Ile Leu Glu Ser Asp Phe
865                 870                 875                 880
Ala Phe Ala

<210> SEQ ID NO 3
<211> LENGTH: 2673
<212> TYPE: DNA
<213> ORGANISM: Artificial Sequence
<220> FEATURE:
<223> OTHER INFORMATION: 6His-T7RNAP

<400> SEQUENCE: 3
atgcaccatc accatcacca tatgaacacg attaacatcg ctaagaacga cttctctgac      60
atcgaactgg ctgctatccc gttcaacact ctggctgacc attacggtga gcgtttagct     120
cgcgaacagt tggcccttga gcatgagtct tacgagatgg gtgaagcacg cttccgcaag     180
atgtttgagc gtcaacttaa agctggtgag gttgcggata cgctgccgc caagcctctc     240 atcactaccc tactccctaa gatgattgca cgcatcaacg actggtttga ggaagtgaaa     300
gctaagcgcg gcaagcgccc gacagccttc cagttcctgc aagaaatcaa gccggaagcc     360
gtagcgtaca tcaccattaa gaccactctg gcttgcctaa ccagtgctga caatacaacc     420
gttcaggctg tagcaagcgc aatcggtcgg gccattgagg acgaggctcg cttcggtcgt     480
atccgtgacc ttgaagctaa gcacttcaag aaaaacgttg aggaacaact caacaagcgc     540
gtagggcacg tctacaagaa agcatttatg caagttgtcg aggctgacat gctctctaag     600
ggtctactcg gtggcgaggc gtggtcttcg tggcataagg aagactctat tcatgtagga     660
```

-continued

```
gtacgctgca tcgagatgct cattgagtca accggaatgg ttagcttaca ccgccaaaat    720
gctggcgtag taggtcaaga ctctgagact atcgaactcg cacctgaata cgctgaggct    780
atcgcaaccc gtgcaggtgc gctggctggc atctctccga tgttccaacc ttgcgtagtt    840
cctcctaagc cgtggactgg cattactggt ggtggctatt gggctaacgg tcgtcgtcct    900
ctggcgctgg tgcgtactca cagtaagaaa gcactgatgc gctacgaaga cgtttacatg    960
cctgaggtgt acaaagcgat taacattgcg caaaacaccg catggaaaat caacaagaaa   1020
gtcctagcgg tcgccaacgt aatcaccaag tggaagcatt gtccggtcga ggacatccct   1080
gcgattgagc gtgaagaact cccgatgaaa ccggaagaca tcgacatgaa tcctgaggct   1140
ctcaccgcgt ggaaacgtgc tgccgctgct gtgtaccgca aggacaaggc tcgcaagtct   1200
cgccgtatca gccttgagtt catgcttgag caagccaata agtttgctaa ccataaggcc   1260
atctggttcc cttacaacat ggactggcgc ggtcgtgttt acgctgtgtc aatgttcaac   1320
ccgcaaggta acgatatgac caaaggactg cttacgctgg cgaaaggtaa accaatcggt   1380
aaggaaggtt actactggct gaaaatccac ggtgcaaact gtgcgggtgt cgataaggtt   1440
ccgttccctg agcgcatcaa gttcattgag gaaaaccacg agaacatcat ggcttgcgct   1500
aagtctccac tggagaacac ttggtgggct gagcaagatt ctccgttctg cttccttgcg   1560
ttctgctttg agtacgctgg ggtacagcac cacggcctga gctataactg ctcccttccg   1620
ctggcgtttg acgggtcttg ctctggcatc cagcacttct ccgcgatgct ccgagatgag   1680
gtaggtggtc gcgcggttaa cttgcttcct agtgaaaccg ttcaggacat ctacgggatt   1740
gttgctaaga aagtcaacga gattctacaa gcagacgcaa tcaatgggac cgataacgaa   1800
gtagttaccg tgaccgatga gaacactggt gaaatctctg agaaagtcaa gctgggcact   1860
aaggcactgg ctggtcaatg gctggcttac ggtgttactc gcagtgtgac taagcgttca   1920
gtcatgacgc tggcttacgg gtccaaagag ttcggcttcc gtcaacaagt gctggaagat   1980
accattcagc cagctattga ttccggcaag ggtctgatgt tcactcagcc gaatcaggct   2040
gctggataca tggctaagct gatttgggaa tctgtgagcg tgacggtggt agctgcggtt   2100
gaagcaatga actggcttaa gtctgctgct aagctgctgg ctgctgaggt caaagataag   2160
aagactggag agattcttcg caagcgttgc gctgtgcatt gggtaactcc tgatggtttc   2220
cctgtgtggc aggaatacaa gaagcctatt cagacgcgct tgaacctgat gttcctcggt   2280
cagttccgct tacagcctac cattaacacc aacaaagata gcgagattga tgcacacaaa   2340
caggagtctg tatcgctcc taactttgta cacagccaag acggtagcca ccttcgtaag   2400
actgtagtgt gggcacacga gaagtacgga atcgaatctt ttgcactgat tcacgactcc   2460
ttcggtacca ttccggctga cgctgcgaac ctgttcaaag cagtgcgcga aactatggtt   2520
gacacatatg agtcttgtga tgtactggct gatttctacg accagttcgc tgaccagttg   2580
cacgagtctc aattggacaa aatgccagca cttccggcta aggtaacttg aacctccgt   2640 gacatcttag agtcggactt cgcgttcgcg taa                                2673
```

<210> SEQ ID NO 4
<211> LENGTH: 890
<212> TYPE: PRT
<213> ORGANISM: Artificial Sequence
<220> FEATURE:
<223> OTHER INFORMATION: 6His-T7RNAP
<400> SEQUENCE: 4

```
Met His His His His His Met Asn Thr Ile Asn Ile Ala Lys Asn
 1               5                  10                  15

Asp Phe Ser Asp Ile Glu Leu Ala Ala Ile Pro Phe Asn Thr Leu Ala
             20                  25                  30

Asp His Tyr Gly Glu Arg Leu Ala Arg Glu Gln Leu Ala Leu Glu His
             35                  40                  45

Glu Ser Tyr Glu Met Gly Glu Ala Arg Phe Arg Lys Met Phe Glu Arg
             50                  55                  60

Gln Leu Lys Ala Gly Glu Val Ala Asp Asn Ala Ala Lys Pro Leu
 65              70                  75                  80

Ile Thr Thr Leu Leu Pro Lys Met Ile Ala Arg Ile Asn Asp Trp Phe
                 85                  90                  95

Glu Glu Val Lys Ala Lys Arg Gly Lys Arg Pro Thr Ala Phe Gln Phe
                100                 105                 110

Leu Gln Glu Ile Lys Pro Glu Ala Val Ala Tyr Ile Thr Ile Lys Thr
            115                 120                 125

Thr Leu Ala Cys Leu Thr Ser Ala Asp Asn Thr Thr Val Gln Ala Val
        130                 135                 140

Ala Ser Ala Ile Gly Arg Ala Ile Glu Asp Glu Ala Arg Phe Gly Arg
145                 150                 155                 160

Ile Arg Asp Leu Glu Ala Lys His Phe Lys Lys Asn Val Glu Glu Gln
                165                 170                 175

Leu Asn Lys Arg Val Gly His Val Tyr Lys Lys Ala Phe Met Gln Val
            180                 185                 190

Val Glu Ala Asp Met Leu Ser Lys Gly Leu Leu Gly Gly Glu Ala Trp
        195                 200                 205

Ser Ser Trp His Lys Glu Asp Ser Ile His Val Gly Val Arg Cys Ile
210                 215                 220

Glu Met Leu Ile Glu Ser Thr Gly Met Val Ser Leu His Arg Gln Asn
225                 230                 235                 240

Ala Gly Val Val Gly Gln Asp Ser Glu Thr Ile Glu Leu Ala Pro Glu
                245                 250                 255

Tyr Ala Glu Ala Ile Ala Thr Arg Ala Gly Ala Leu Ala Gly Ile Ser
            260                 265                 270

Pro Met Phe Gln Pro Cys Val Val Pro Pro Lys Pro Trp Thr Gly Ile
        275                 280                 285

Thr Gly Gly Gly Tyr Trp Ala Asn Gly Arg Arg Pro Leu Ala Leu Val
        290                 295                 300

Arg Thr His Ser Lys Lys Ala Leu Met Arg Tyr Glu Asp Val Tyr Met
305                 310                 315                 320

Pro Glu Val Tyr Lys Ala Ile Asn Ile Ala Gln Asn Thr Ala Trp Lys
            325                 330                 335

Ile Asn Lys Lys Val Leu Ala Val Ala Asn Val Ile Thr Lys Trp Lys
            340                 345                 350

His Cys Pro Val Glu Asp Ile Pro Ala Ile Glu Arg Glu Glu Leu Pro
        355                 360                 365

Met Lys Pro Glu Asp Ile Asp Met Asn Pro Glu Ala Leu Thr Ala Trp
        370                 375                 380

Lys Arg Ala Ala Ala Val Tyr Arg Lys Asp Lys Ala Arg Lys Ser
385                 390                 395                 400

Arg Arg Ile Ser Leu Glu Phe Met Leu Glu Gln Ala Asn Lys Phe Ala
                405                 410                 415

Asn His Lys Ala Ile Trp Phe Pro Tyr Asn Met Asp Trp Arg Gly Arg
```

```
            420                 425                 430
Val Tyr Ala Val Ser Met Phe Asn Pro Gln Gly Asn Asp Met Thr Lys
            435                 440                 445
Gly Leu Leu Thr Leu Ala Lys Gly Lys Pro Ile Gly Lys Glu Gly Tyr
            450                 455                 460
Tyr Trp Leu Lys Ile His Gly Ala Asn Cys Ala Gly Val Asp Lys Val
465                 470                 475                 480
Pro Phe Pro Glu Arg Ile Lys Phe Ile Glu Glu Asn His Glu Asn Ile
                    485                 490                 495
Met Ala Cys Ala Lys Ser Pro Leu Glu Asn Thr Trp Trp Ala Glu Gln
                500                 505                 510
Asp Ser Pro Phe Cys Phe Leu Ala Phe Cys Phe Glu Tyr Ala Gly Val
            515                 520                 525
Gln His His Gly Leu Ser Tyr Asn Cys Ser Leu Pro Leu Ala Phe Asp
            530                 535                 540
Gly Ser Cys Ser Gly Ile Gln His Phe Ser Ala Met Leu Arg Asp Glu
545                 550                 555                 560
Val Gly Gly Arg Ala Val Asn Leu Leu Pro Ser Glu Thr Val Gln Asp
                565                 570                 575
Ile Tyr Gly Ile Val Ala Lys Lys Val Asn Glu Ile Leu Gln Ala Asp
                580                 585                 590
Ala Ile Asn Gly Thr Asp Asn Glu Val Val Thr Val Thr Asp Glu Asn
            595                 600                 605
Thr Gly Glu Ile Ser Glu Lys Val Lys Leu Gly Thr Lys Ala Leu Ala
            610                 615                 620
Gly Gln Trp Leu Ala Tyr Gly Val Thr Arg Ser Val Thr Lys Arg Ser
625                 630                 635                 640
Val Met Thr Leu Ala Tyr Gly Ser Lys Glu Phe Gly Phe Arg Gln Gln
                645                 650                 655
Val Leu Glu Asp Thr Ile Gln Pro Ala Ile Asp Ser Gly Lys Gly Leu
                660                 665                 670
Met Phe Thr Gln Pro Asn Gln Ala Ala Gly Tyr Met Ala Lys Leu Ile
            675                 680                 685
Trp Glu Ser Val Ser Val Thr Val Ala Ala Val Glu Ala Met Asn
            690                 695                 700
Trp Leu Lys Ser Ala Ala Lys Leu Leu Ala Ala Glu Val Lys Asp Lys
705                 710                 715                 720
Lys Thr Gly Glu Ile Leu Arg Lys Arg Cys Ala Val His Trp Val Thr
                725                 730                 735
Pro Asp Gly Phe Pro Val Trp Gln Glu Tyr Lys Lys Pro Ile Gln Thr
            740                 745                 750
Arg Leu Asn Leu Met Phe Leu Gly Gln Phe Arg Leu Gln Pro Thr Ile
            755                 760                 765
Asn Thr Asn Lys Asp Ser Glu Ile Asp Ala His Lys Gln Ser Gly
            770                 775                 780
Ile Ala Pro Asn Phe Val His Ser Gln Asp Gly Ser His Leu Arg Lys
785                 790                 795                 800
Thr Val Val Trp Ala His Glu Lys Tyr Gly Ile Glu Ser Phe Ala Leu
                805                 810                 815
Ile His Asp Ser Phe Gly Thr Ile Pro Ala Asp Ala Ala Asn Leu Phe
            820                 825                 830
Lys Ala Val Arg Glu Thr Met Val Asp Thr Tyr Glu Ser Cys Asp Val
            835                 840                 845
```

Leu Ala Asp Phe Tyr Asp Gln Phe Ala Asp Gln Leu His Glu Ser Gln
            850                 855                 860

Leu Asp Lys Met Pro Ala Leu Pro Ala Lys Gly Asn Leu Asn Leu Arg
865                 870                 875                 880

Asp Ile Leu Glu Ser Asp Phe Ala Phe Ala
                885                 890

<210> SEQ ID NO 5
<211> LENGTH: 3060
<212> TYPE: DNA
<213> ORGANISM: Artificial Sequence
<220> FEATURE:
<223> OTHER INFORMATION: DNA template

<400> SEQUENCE: 5

| | | | | | | |
|---|---|---|---|---|---|---|
| gatcttcttg | agatcctttt | tttctgcgcg | taatctgctg | cttgcaaaca | aaaaaaccac | 60 |
| cgctaccagc | ggtggtttgt | ttgccggatc | aagagctacc | aactcttttt | ccgaaggtaa | 120 |
| ctggcttcag | cagagcgcag | ataccaaata | ctgttcttct | agtgtagccg | tagttagccc | 180 |
| accacttcaa | gaactctgta | gcaccgccta | catacctcgc | tctgctaatc | ctgttaccag | 240 |
| tggctgctgc | cagtggcgat | aagtcgtgtc | ttaccgggtt | ggactcaaga | cgatagttac | 300 |
| cggataaggc | gcagcggtcg | ggctgaacgg | ggggttcgtg | cacacagccc | agcttggagc | 360 |
| gaacgaccta | caccgaactg | agatacctac | agcgtgagct | atgagaaagc | gccacgcttc | 420 |
| ccgaagggag | aaaggcggac | aggtatccgg | taagcggcag | ggtcggaaca | ggagagcgca | 480 |
| cgagggagct | tccaggggga | aacgcctggt | atctttatag | tcctgtcggg | tttcgccacc | 540 |
| tctgacttga | gcgtcgattt | ttgtgatgct | cgtcagggg | gcggagccta | tggaaaaacg | 600 |
| ccagcaacgc | ggcctttta | cggttcctgg | ccttttgctg | gccttttgct | cacatgttct | 660 |
| ttcctgcgtt | atcccctgat | tctgtggata | accgtattac | cgcctttgag | tgagctgata | 720 |
| ccgctcgccg | cagccgaacg | accgagcgca | gcgagtcagt | gagcgaggaa | gcggaaggcg | 780 |
| agagtaggga | actgccaggc | atcaaactaa | gcagaaggcc | cctgacggat | ggcctttttg | 840 |
| cgtttctaca | aactcttttct | gtgttgtaaa | acgacggcca | gtcttaagct | cgggcccct | 900 |
| gggcggttct | gataacgagt | aatcgttaat | ccgcaaataa | cgtaaaaacc | cgcttcggcg | 960 |
| ggttttttta | tggggggagt | ttagggaaag | agcatttgtc | agaatattta | agggcgcctg | 1020 |
| tcactttgct | tgatatatga | gaattatttta | accttataaa | tgagaaaaaa | gcaacgcact | 1080 |
| ttaaataaga | tacgttgctt | tttcgattga | tgaacaccta | taattaaact | attcatctat | 1140 |
| tatttatgat | tttttgtata | tacaatattt | ctagtttgtt | aaagagaatt | aagaaaataa | 1200 |
| atctcgaaaa | taataaaggg | aaaatcagtt | tttgatatca | aaattataca | tgtcaacgat | 1260 |
| aatacaaaat | ataatacaaa | ctataagatg | ttatcagtat | ttattatgca | tttagaataa | 1320 |
| attttgtgtc | gcccttgtac | ttagtcgctg | aataatacga | ctcactatag | cggaacccaa | 1380 |
| gctaagcgcc | agaactggca | ccttcgggtg | ccagttgacg | aggtgggtt | atcgagatt | 1440 |
| tcggcggatg | actcccggtt | gttcatcaca | accgcaagct | tttacttaaa | tcattaaggt | 1500 |
| gacttagtgg | acaaaggtga | aagtgtgatg | aaacccgacc | tggacggagg | cgcgcccgag | 1560 |
| atgagtaggc | tgtcccatca | ggggaggaat | cggggacggc | tgaaaggcga | gggcgccgaa | 1620 |
| gcgagcagag | ttcctcccgc | tctgcttggc | tgggggtgag | gggaataccc | ttaccactgt | 1680 |
| cgcgaaagcg | gagagccgtc | caggatcccg | tcaaaagggc | gacacccat | aattagcccg | 1740 |
| ggcgaaaggc | ccagtctttc | gactgagcct | ttcgttttat | ttgatgcctg | gcagttccct | 1800 |

```
actctcgcat ggggagtccc cacactacca tcggcgctac ggcgtttcac ttctgagttc    1860
ggcatggggt caggtgggac caccgcgcta ctgccgccag gcaaacaagg ggtgttatga    1920
gccatattca ggtataaatg ggctcgcgat aatgttcaga attggttaat tggttgtaac    1980
actgacccct atttgtttat ttttctaaat acattcaaat atgtatccgc tcatgagaca    2040
ataaccctga taaatgcttc aataatattg aaaaggaag aatatgagta ttcaacattt     2100
ccgtgtcgcc cttattccct tttttgcggc attttgcctt cctgttttg ctcacccaga     2160 aacgctggtg aaagtaaaag atgctgaaga tcagttgggt gcacgagtgg gttacatcga    2220
actggatctc aacagcggta agatccttga gagttttcgc cccgaagaac gttttccaat    2280
gatgagcact tttaaagttc tgctatgtgg cgcggtatta tcccgtattg acgccgggca    2340
agagcaactc ggtcgccgca tacactattc tcagaatgac ttggttgagt actcaccagt    2400
cacagaaaag catcttacgg atggcatgac agtaagagaa ttatgcagtg ctgccataac    2460
catgagtgat aacactgcgg ccaacttact tctgacaacg atcggaggac cgaaggagct    2520
aaccgctttt ttgcacaaca tgggggatca tgtaactcgc cttgatcgtt gggaaccgga    2580
gctgaatgaa gccataccaa acgacgagcg tgacaccacg atgcctgtag cgatggcaac    2640
aacgttgcgc aaactattaa ctggcgaact acttactcta gcttcccggc aacaattaat    2700
agactggatg gaggcggata aagttgcagg accacttctg cgctcggccc ttccggctgg    2760
ctggtttatt gctgataaat ccggagccgg tgagcgtggt tctcgcggta tcatcgcagc    2820 gctgggggcca gatggtaagc cctcccgtat cgtagttatc tacacgacgg ggagtcaggc    2880
aactatggat gaacgaaata gacagatcgc tgagataggt gcctcactga ttaagcattg    2940
gtaaaagcag agcattacgc tgacttgacg gacggcgca agctcatgac caaaatccct     3000
taacgtgagt tacgcgcgcg tcgttccact gagcgtcaga ccccgtagaa aagatcaaag    3060
```

<210> SEQ ID NO 6
<211> LENGTH: 334
<212> TYPE: RNA
<213> ORGANISM: Artificial Sequence
<220> FEATURE:
<223> OTHER INFORMATION: RNA Transcript

<400> SEQUENCE: 6

```
gcggaaccca agcuaagcgc cagaacuggc accuucgggu gccaguugac gaggugggu     60 uuaucgagau uucggcggau gacucccggu uguucaucac aaccgcaagc uuuuacuuaa    120
aucauuaagg ugacuuagug gacaaaggug aaagugugua gaaacccgac cuggacggag    180
gcgcgcccga gaugaguagg cugucccauc aggggaggaa ucgggacgg cugaaaggcg     240 agggcgccga agcgagcaga guuccucccg cucugcuugg cuggggguga gggaauacc     300 cuuaccacug ucgcgaaagc ggagagccgu ccag                                334
```

<210> SEQ ID NO 7
<211> LENGTH: 16
<212> TYPE: RNA
<213> ORGANISM: Artificial Sequence
<220> FEATURE:
<223> OTHER INFORMATION: RNA cleavage product

<400> SEQUENCE: 7

```
gcggaaccca agcuaa                                                    16
```

<210> SEQ ID NO 8

<211> LENGTH: 4671
<212> TYPE: DNA
<213> ORGANISM: Artificial Sequence
<220> FEATURE:
<223> OTHER INFORMATION: Substrate etc

<400> SEQUENCE: 8

```
gagttacgcg cgcgtcgttc cactgagcgt cagaccccgt agaaaagatc aaaggatctt      60
cttgagatcc ttttttttctg cgcgtaatct gctgcttgca acaaaaaaaa ccaccgctac     120
cagcggtggt ttgtttgccg gatcaagagc taccaactct ttttccgaag gtaactggct     180
tcagcagagc gcagatacca aatactgttc ttctagtgta gccgtagtta gcccaccact     240
tcaagaactc tgtagcaccg cctacatacc tcgctctgct aatcctgtta ccagtggctg     300
ctgccagtgg cgataagtcg tgtcttaccg ggttggactc aagacgatag ttaccggata     360
aggcgcagcg gtcgggctga acggggggtt cgtgcacaca gcccagcttg gagcgaacga     420
cctacaccga actgagatac ctacagcgtg agctatgaga aagcgccacg cttcccgaag     480
ggagaaaggc ggacaggtat ccggtaagcg gcagggtcgg aacaggagag cgcacgaggg     540
agcttccagg gggaaacgcc tggtatcttt atagtcctgt cgggtttcgc cacctctgac     600
ttgagcgtcg attttttgtga tgctcgtcag ggggcggag cctatggaaa aacgccagca     660
acgcggcctt tttacggttc ctggcctttt gctggccttt tgctcacatg ttctttcctg     720
cgttatcccc tgattctgtg gataaccgta ttaccgcctt tgagtgagct gataccgctc     780
gccgcagccg aacgaccgag cgcagcgagt cagtgagcga ggaagcggaa ggcgagagta     840
gggaactgcc aggcatcaaa ctaagcagaa ggccccctgac ggatggcctt tttgcgtttc     900
tacaaactct ttctgtgttg taaaacgacg gccagtctta agctcgggcc cctgggcgg     960
ttctgataac gagtaatcgt taatccgcaa ataacgtaaa aacccgcttc ggcgggtttt    1020
tttatggggg gagtttaggg aaagagcatt tgtcagaata tttaagggcg cctgtcactt    1080
tgcttgatat atgagaatta tttaaccta taaatgagaa aaaagcaacg cactttaaat    1140
aagatacgtt gctttttcga ttgatgaaca cctataatta aactattcat ctattattta    1200
tgattttttg tatatacaat atttctagtt tgttaaagag aattaagaaa ataaatctcg    1260
aaaataataa agggaaaatc agttttttgat atcaaaatta tacatgtcaa cgataataca    1320
aaatataata caaactataa gatgttatca gtatttatta tgcatttaga atacgtactc    1380
agcgtctggg ttccccatcg gtgatgtcgt ataagagacg tataggagac ctatagtgtc    1440
ttcggggtaa tacgactcac tatagcggaa cccaagcttg gcattccggt actgttggta    1500
aagccaccat ggaagatgcg aagaacataa agaaaggtcc cgccccattt tacccactcg    1560
aggatggaac agctggggag caactgcaca aggccatgaa gcgctatgcg ttggtgccgg    1620
gaaccatcgc gttcaccgac gcacacatcg aagtgaacat cacttacgcc gagtactttg    1680
agatgagcgt caggctggcc gaggctatga acgcatacgg tctgaacacc aaccaccgga    1740
tcgtggtctg ctctgaaaac agcctgcagt tcttcatgcc ggtcctgggg gccctgttca    1800
tcggcgtggc cgtggcaccc gccaacgata tctacaacga gagagaattg ctgaactcga    1860
tgaacatctc ccagcctacc gtggtgttcg tgtcgaagaa ggggttgcag aagatcctga    1920
acgtgcagaa gaagctgccc atcattcaaa agattatcat tatggattcc aaaaccgact    1980
accagggttt ccagtcaatg tataccttcg tgacctccca tctgccccct ggcttcaacg    2040
aatacgactt cgtgcctgaa agcttcgacc gcgacaagac gatcgccctc atcatgaact    2100
cgtccggctc gaccgggctg cccaaaggag tggcctgcc acaccggacc gcttgcgtgc    2160
```

```
ggttctccca cgcccgggac cctatttttcg gcaatcagat cattccggac actgccatcc    2220
tgagcgtggt cccccttccat cacgggtttg gatgtttac cactctgggc tacctcatct    2280
gcggattcag ggtggtgctg atgtaccggt tcgaggaaga acttttcctg cggagcctgc    2340
aggattacaa gatccagtcc gccctcctcg tgccaaccct cttctcattc ttcgctaagt    2400
ccactctcat cgataagtac gacctgtcga atctccacga aattgcgtcc ggtggtgcac    2460
cgctgtccaa ggaggtcggc gaagccgtgg ccaagcgctt ccacctcccg ggaatacgcc    2520
agggatacgg cctgactgaa acgaccagcg cgattctgat caccccggag ggcgacgaca    2580
agccgggtgc cgtggggaaa gtggtgccgt tcttcgaagc aaaggtcgtg gatctggata    2640
ccggaaagac tctgggcgtg aaccagagag gggaactttg tgtgcgcgga ccgatgatta    2700
tgtccggata tgtcaacaac cccgaggcca ctaatgccct gatcgacaag acgacgatggt    2760 tgcatagcgg cgacatcgca tactgggacg aggacgagca cttttttcatt gtggatcggc    2820 tcaagtccct gatcaagtac aagggatacc aggtcgcccc tgccgaactt gagtccatcc    2880
tgctgcaaca tccgaacatt ttcgacgcgg gcgtcgctgg ccttcctgat gatgacgccg    2940
gagagctgcc cgcggccgtg gtggtgctcg aacacggaaa aactatgacc gagaaggaaa    3000
tcgtggacta cgtggcgtca caagtcacca ctgccaagaa actgcgcggc ggagtcgtgt    3060
tcgtggacga ggtgcccaag ggcctgaccg gaaagctgga cgctagaaag atccgggaga    3120
tcctgattaa ggccaagaag ggaggaaagt ccaagctctg agatctagag ggccctattc    3180
tatagtgtca cctaaatgct aaaaaaaaaa aaaaaaaaa aaaaaaaaaa aaaaaaaaa    3240 aaaaaaaaaa aaaaaaaaaa aaaaaaaaaa aaaaaaaaaa aaaaaaaaaa aaaaaaaaaa    3300
gaattcaaaa gaagaccata tacgtctcct ataggtctcg tatactgctt cctatacgac    3360
atcaccgatg gggaacacga agcgatccag ccccccttat tagcccgggc gaaaggccca    3420
gtctttcgac tgagcctttc gttttatttg atgcctggca gttccctact ctcgcatggg    3480
gagtccccac actaccatcg gcgctacggc gtttcacttc tgagttcggc atggggtcag    3540
gtgggaccac cgcgctactg ccgccaggca acaagggggt gttatgagcc atattcaggt    3600
ataaatgggc tcgcgataat gttcagaatt ggttaattgg ttgtaacact gacccctatt    3660
tgtttatttt tctaaataca ttcaaatatg tatccgctca tgagacaata accctgataa    3720
atgcttcaat aatattgaaa aaggaagaat atgagtattc aacatttccg tgtcgccctt    3780
attccctttt ttgcggcatt ttgccttcct gtttttgctc acccagaaac gctggtgaaa    3840
gtaaaagatg ctgaagatca gttgggtgca cgagtgggtt acatcgaact ggatctcaac    3900
agcggtaaga tccttgagag ttttcgcccc gaagaacgtt ttccaatgat gagcactttt    3960
aaagttctgc tatgtggcgc ggtattatcc cgtattgacg ccgggcaaga gcaactcggt    4020
cgccgcatac actattctca gaatgacttg gttgagtact caccagtcac agaaaagcat    4080
cttacggatg gcatgacagt aagagaatta tgcagtgctg ccataaccat gagtgataac    4140
actgcggcca acttacttct gacaacgatc ggaggaccga aggagctaac cgcttttttg    4200
cacaacatgg ggatcatgt aactcgcctt gatcgttggg aaccggagct gaatgaagcc    4260
ataccaaacg acgagcgtga caccacgatg cctgtagcga tggcaacaac gttgcgcaaa    4320
ctattaactg gcgaactact tactctagct tcccggcaac aattaataga ctggatggag    4380
gcggataaag ttgcaggacc acttctgcgc tcggcccttc cggctggctg gtttattgct    4440
gataaatccg gagccggtga gcgtggttct cgcggtatca tcgcagcgct ggggccagat    4500
```

```
ggtaagccct cccgtatcgt agttatctac acgacgggga gtcaggcaac tatggatgaa    4560
cgaaatagac agatcgctga gataggtgcc tcactgatta agcattggta agcagagcat    4620
tacgctgact tgacgggacg gcgcaagctc atgaccaaaa tcccttaacg t             4671
```

<210> SEQ ID NO 9
<211> LENGTH: 1697
<212> TYPE: RNA
<213> ORGANISM: Artificial Sequence
<220> FEATURE:
<223> OTHER INFORMATION: Substrate etc

<400> SEQUENCE: 9

```
gcggaaccca agcuuggcau uccgguacug uugguaaagc caccauggaa gaugcgaaga      60
acauaaagaa aggucccgcc ccauuuuacc cacucgagga uggaacagcu ggggagcaac     120
ugcacaaggc caugaagcgc uaugcguugg ugccgggaac caucgcguuc accgacgcac     180
acaucgaagu gaacaucacu uacgccgagu acuuugagau gagcgucagg cuggccgagg     240
cuaugaagcg auacggucug aacaccaacc accggaucgu ggucugcucu gaaaacagcc     300
ugcaguucuu caugccgguc cuggggggccc uguucaucgg cguggccgug gcacccgcca     360
acgauaucua caacgagaga gaauugcuga acucgaugaa caucucccag ccuaccgugg     420 uguucgcuguc gaagaagggg uugcagaaga uccugaacgu gcagaagaag cugcccauca     480
uucaaaagau uauauauug gauuccaaaa ccgacuacca ggguuccag ucaauguaua       540 ccuucgugac cucccaucug cccccuggcu ucaacgaaua cgacuucgug ccugaaagcu     600
ucgaccgcga caagacgauc gcccucauca ugaacucguc cggcucgacc gggcugccca     660 aaggagugc ccugccacac cggaccgcuu gcgugcgguu ucccacgcc cgggacccua       720 uuuucgcaa ucagaucauu ccggacacug ccauccugag cguggucccc uuccaucacg      780 gguuuggau guuuaccacu cugggcuacc ucaucugcgg auucaggugug ugcugaugu     840 accgguucga ggaagaacuu uuccugcgga gccugcagga uuacaagauc caguccgccc    900
uccucgugcc aacccucuuc ucauucuucg cuaagccac ucuacgau aaguacgacc       960 ugucgaaucu ccacgaaaauu gcguccggug gugcaccgcu guccaaggag ucggcgaag    1020 ccguggccaa gcgcuuccac cucccgggaa uacgccaggg auacggccug acugaaacga    1080
ccagcgcgau ucugauccacc ccggagggcg acgacaagcc gggugccgug gggaaagugg   1140
ugccguucuu cgaagcaaag gucguggauc uggauaccgg aaagacucug ggcgugaacc    1200
agagagggga acuuugugug cgcggaccga ugauuaugucc cggauagguc aacacccccg   1260
aggccacuaa ugcccugauc gacaaggacg gauggguguca uagcggcgac aucgcauacu   1320
gggacgagga cgagcacuuu uucauugugg aucggcucaa gucccugauc aaguacaagg    1380
gauaccaggu cgccccugcc gaacuugagu ccauccugcu gcaacauccg aacauuuucg    1440
acgcgggcgu cgcucggccuu ccugaugaug acgccggaga gcugcccgcg gccguggugg   1500
ugcucgaaca cggaaaaacu augaccgaga aggaaaucgu ggacuacgug gcgucacaag    1560
ucaccacugc caagaaacug cgcggcggag ucguguucgu ggacgagguug cccaagggcc    1620 ugaccggaaa gcuggacgcu agaaagauc gggagauccu gauuaagcc aagaagggag    1680 gaaaguccaa gcucuga                                                    1697
```

<210> SEQ ID NO 10
<211> LENGTH: 4945
<212> TYPE: DNA
<213> ORGANISM: Artificial Sequence
<220> FEATURE:
<223> OTHER INFORMATION: Substrate etc

<400> SEQUENCE: 10

```
ttaccaatgc ttaatcagtg aggcacctat ctcagcgatc tgtctatttc gttcatccat      60
agttgcctga ctccccgtcg tgtagataac tacgatacgg gagggcttac catctggccc     120
cagcgctgcg atgataccgc gagaaccacg ctcaccggct ccggatttat cagcaataaa     180
ccagccagcc ggaagggccg agcgcagaag tggtcctgca actttatccg cctccatcca     240
gtctattaat tgttgccggg aagctagagt aagtagttcg ccagttaata gtttgcgcaa     300
cgttgttgcc atcgctacag gcatcgtggt gtcacgctcg tcgtttggta tggcttcatt     360
cagctccggt tcccaacgat caaggcgagt tacatgatcc cccatgttgt gcaaaaaagc     420
ggttagctcc ttcggtcctc cgatcgttgt cagaagtaag ttggccgcag tgttatcact     480
catggttatg gcagcactgc ataattctct tactgtcatg ccatccgtaa gatgcttttc     540
tgtgactggt gagtactcaa ccaagtcatt ctgagaatag tgtatgcggc gaccgagttg     600
ctcttgcccg gcgtcaatac gggataatac cgcgccacat agcagaactt taaaagtgct     660
catcattgga aaacgttctt cggggcgaaa actctcaagg atcttaccgc tgttgagatc     720
cagttcgatg taacccactc gtgcacccaa ctgatcttca gcatctttta ctttcaccag     780
cgtttctggg tgagcaaaaa caggaaggca aaatgccgca aaaaagggaa taagggcgac     840
acggaaatgt tgaatactca tattcttcct ttttcaatat tattgaagca tttatcaggg     900
ttattgtctc atgagcggat acatatttga atgtatttag aaaaataaac aaataggggt     960
cagtgttaca accaattaac caattctgaa cattatcgcg agcccattta tacctgaata    1020
tggctcataa cacccttgt tgcctggcg gcagtagcgc ggtggtccca cctgaccccca    1080
tgccgaactc agaagtgaaa cgccgtagcg ccgatggtag tgtggggact ccccatgcga    1140
gagtagggaa ctgccaggca tcaaatataaa cgaaaggctc agtcgaaaga ctgggccttt    1200
cgccccgggct aattatgggg tgtcgccctt cgctgaaggg gtaatacgac tcactatagg    1260
gaaataagag agaaaagaag agtaagaaga aatataagag ccaccatgga agatgcgaag    1320
aacataaaga aaggtcccgc cccattttac ccactcgagg atggaacagc tggggagcaa    1380
ctgcacaagg ccatgaagcg ctatgcgttg gtgccgggaa ccatcgcgtt caccgacgca    1440
cacatcgaag tgaacatcac ttacgccgag tactttgaga tgagcgtcag gctggccgag    1500
gctatgaagc gatacggtct gaacaccaac caccggatcg tggtctgctc tgaaaacagc    1560
ctgcagttct tcatgccggt cctgggggcc tgttcatcg gcgtggccgt ggcacccgcc    1620
aacgatatct acaacgagag agaattgctg aactcgatga acatctccca gcctaccgtg    1680
gtgttcgtgt cgaagaaggg gttgcagaag atcctgaacg tgcagaagaa gctgcccatc    1740
attcaaaaga ttatcattat ggattccaaa accgactacc agggtttcca gtcaatgtat    1800
accttcgtga cctcccatct gccccctggc ttcaacgaat cgacttcgt gcctgaaagc    1860
ttcgaccgcg acaagacgat cgccctcatc atgaactcgt ccggctcgac cgggctgccc    1920
aaaggagtgg ccctgccaca ccggaccgct tgcgtgcggt tctcccacgc ccggaccct    1980
attttcggca atcagatcat tccggacact gccatcctga cgtggtccc cttccatcac    2040
gggtttggga tgtttaccac tctgggctac ctcatctgcg gattcagggt ggtgctgatg    2100
taccggttcg aggaagaact tttcctgcgg agcctgcagg attacaagat ccagtccgcc    2160
ctcctcgtgc caaccctctt ctcattcttc gctaagtcca ctctcatcga taagtacgac    2220
```

```
ctgtcgaatc tccacgaaat tgcgtccggt ggtgcaccgc tgtccaagga ggtcggcgaa    2280
gccgtggcca agcgcttcca cctcccggga attcgccagg gatacggcct gactgaaacg    2340
accagcgcga ttctgatcac cccggagggc gacgacaagc cgggtgccgt ggggaaagtg    2400
gtgccgttct tcgaagcaaa ggtcgtggat ctggataccg aaagactct gggcgtgaac     2460 cagagagggg aactttgtgt gcgcggaccg atgattatgt ccggatatgt caacaacccc    2520
gaggccacta tgccctgat cgacaaggac ggatggttgc atagcggcga catcgcatac     2580
tgggacgagg acgagcactt tttcattgtg gatcggctca agtccctgat caagtacaag    2640
ggataccagg tcgcccctgc cgaacttgag tccatcctgc tgcaacatcc gaacattttc    2700
gacgcgggcg tcgctggcct tcctgatgat gacgccggag agctgcccgc ggccgtggtg    2760
gtgctcgaac acgaaaaaac tatgaccgag aaggaaatcg tggactacgt ggcgtcacaa    2820
gtcaccactg ccaagaaact cgcgcggcgga gtcgtgttcg tggacgaggt gcccaagggc    2880
ctgaccggaa agctggacgc tagaaagatc cgggagatcc tgattaaggc caagaaggga    2940
ggaaagtcca agctctgaat ctgctgcctt ctgcggggct tgccttctgg ccatgccctt    3000
cttctctccc ttgcacctgt acctcttggt ctttgaataa agcctgagta ggaagtgagg    3060
gaaaaaaaaa aaaaaaaaaa aaaaaaaaaa aaaaaaaaaa aaaaaaaaaa aaaaaaaaaa    3120
aaaaaaaaaa aaaaaaaaaa aaaaaaaaaa aaaaaaaaaa aaaaaaagga agagcgctgc    3180
ctccttcaga gtctgctcac gagctcggtc tcggatcccc tatacgacat caccgatggg    3240
gaacacgaag cgatccagcc ccccttatta gcccgggcga aaggcccagt ctttcgactg    3300
agcctttcgt tttatttgat gcctggcagt tccctactct cgcatgggga gtccccacac    3360
taccatcggc gctacggcgt ttcacttctg agttcggcat ggggtcaggt gggaccaccg    3420
cgctactgcc gccaggcaaa caaggggtgt tatgagccat attcaggtat aaatgggctc    3480
gcgaaaacgt caaagggcg acacaaaatt tattctaaat gcataataaa tactgataac    3540
atcttatagt ttgtattata ttttgtatta tcgttgacat gtataatttt gatatcaaaa    3600
actgattttc cctttattat tttcgagatt tattttctta attctcttta acaaactaga    3660
aatattgtat atacaaaaaa tcataaataa tagatgaata gtttaattat aggtgttcat    3720
caatcgaaaa agcaacgtat cttatttaaa gtgcgttgct ttttctcat ttataaggtt     3780 aaataattct catatatcaa gcaaagtgac aggcgccctt aaatattctg acaaatgctc    3840
tttccctaaa ctcccccat aaaaaaccc gccgaagcgg ttttttacgt tatttgcgga     3900
ttaacgatta ctcgttatca gaaccgccca ggggcccga gcttaagact ggccgtcgtt      3960
ttacaacaca gaaagagttt gtagaaacgc aaaaaggcca tccgtcaggg gccttctgct    4020
tagtttgatg cctggcagtt ccctactctc gccttccgct tcctcgctca ctgactcgct    4080
gcgctcggtc gttcggctgc ggcgagcggt atcagctcac tcaaaggcgg taatacggtt    4140
atccacagaa tcaggggata acgcaggaaa gaacatgtga gcaaaaggcc agcaaaaggc    4200
caggaaccgt aaaaaggccg cgttgctggc gttttccat aggctccgcc cccctgacga     4260
gcatcacaaa aatcgacgct caagtcagag gtggcgaaac ccgacaggac tataaagata    4320
ccaggcgttt cccctggaa gctccctcgt gcgctctcct gttccgaccc tgccgcttac     4380
cggatacctg tccgccttc tccttcggg aagcgtggcg ctttctcata gctcacgctg       4440
taggtatctc agttcggtgt aggtcgttcg ctccaagctg ggctgtgtgc acgaaccccc    4500
cgttcagccc gaccgctgcg ccttatccgg taactatcgt cttgagtcca acccggtaag    4560
acacgactta tcgccactgg cagcagccac tggtaacagg attagcagag cgaggtatgt    4620
```

```
aggcggtgct acagagttct tgaagtggtg ggctaactac ggctacacta gaagaacagt    4680
atttggtatc tgcgctctgc tgaagccagt taccttcgga aaaagagttg gtagctcttg    4740
atccggcaaa caaaccaccg ctggtagcgg tggttttttt gtttgcaagc agcagattac    4800
gcgcagaaaa aaaggatctc aagaagatcc tttgatcttt tctacggggt ctgacgctca    4860
gtggaacgac gcgcgcgtaa ctcacgttaa gggattttgg tcatgagctt gcgccgtccc    4920
gtcaagtcag cgtaatgctc tgctt                                           4945
```

<210> SEQ ID NO 11
<211> LENGTH: 1955
<212> TYPE: RNA
<213> ORGANISM: Artificial Sequence
<220> FEATURE:
<223> OTHER INFORMATION: Substrate etc

<400> SEQUENCE: 11

```
gggaauaag agagaaaga agaguaagaa gaaauauaag agccaccaug gaagaugcga      60
agaacauaaa gaaaggcccc gccccauuuu acccacucga ggauggaaca gcuggggagc    120
aacugcacaa ggccaugaag cgcuaugcgu uggugccggg aaccaucgcg uucaccgacg    180
cacacaucga agugaacauc acuuacgccg aguacuuuga gaugagcguc aggcuggccg    240
aggcuaugaa gcgauacggu cugaacacca accaccggau cguggucugc ucugaaaaca    300
gccugcaguu cuucaugccg guccuggggg cccuguucau cggcguggcc guggcacccg    360
ccaacgauau cuacaacgag agagaauugc ugaacucgau gaacaucucc cagccuaccg    420 uggugucgu gucgaagaag ggguugcaga agauccugaa cgugcagaag aagcugccca    480
ucauucaaaa gauuaucauu auggauucca aaccgacua ccagguuuc cagucaaugu    540 auaccuucgu gaccucccau cugcccccug gcuucaacga uacgacuuc gugccugaaa    600 gcuucgaccg cgacaagacg aucgcccuca ucaugaacuc guccggcucg accgggcugc    660
ccaaaggagu ggcccugcca caccggaccg cuugcgugcg guucucccac gcccgggacc    720
cuauuuucgg caaucagauc auuccggaca cugccauccu gagcgugguc cccuuccauc    780 acgguuugg gaugguuacc acucuggcu accaucaucg cggauucagg gugugcuga    840 uguaccgguu cgaggaagaa cuuuuccugc ggagccugca ggauuacaag auccaguccg    900 cccuccugu gccaacccuc uucucauucu ucgcuaaguc cacucucauc gauaaguacg    960
accugucgaa ucuccacgaa auugcgucg gugugcacc gcugccaag gaggucggcg    1020 aagccguggc caagcgcuuc caccuccgg gaauucgcca gggauacggc cugacugaaa    1080
cgaccagcgc gauucugauc accccggagg gcgacgacaa gccgggugcc gugggaaag    1140 uggugccguu cuucgaagca aaggucgugg aucuggauac cggaaagacu cugggcguga    1200
accagagagg ggaacuuugu gugcgcggac cgaugauuau guccggauau gucaacaacc    1260
ccgaggccac uaaugcccug aucgacaag acggaugguu gcaugcggc gacaucgcau    1320 acugggacga ggacgagcac uuuuucauug uggaucggcu caagucccug aucaaguaca    1380
agggauacca ggucgcccu gccgaacuug aguccaucu gcugcaacau ccgaacauuu    1440
ucgacgcggg cgucgcuggc cuuccugaug augacgccgg agagcugccc gcggccgugg    1500
uggugcucga acacggaaaa acuaugaccg agaaggaaau cguggacuac guggcgucac    1560
aagucaccac ugccaagaaa cugcgcgcg gagucguguu cguggacgag gugccaagg    1620 gccugaccgg aaagcuggac gcuagaaaga uccgggagau ccugauuaag gccaagaagg    1680
```

| | | |
|---|---|---|
| gaggaaaguc caagcucuga aucugcugcc uucugcgggg cuugccuucu ggccaugccc | 1740 | |
| uucuucucuc ccuugcaccu guaccucuug gucuuugaau aaagccugag uaggaaguga | 1800 | |
| gggaaaaaaa aaaaaaaaaa aaaaaaaaaa aaaaaaaaaa aaaaaaaaaa aaaaaaaaaa | 1860 | |
| aaaaaaaaaa aaaaaaaaaa aaaaaaaaaa aaaaaaaaaa aaaaaaaaag gaagagcgcu | 1920 | |
| gccuccuuca gagucugcuc acgagcucgg ucucg | 1955 | |

```
<210> SEQ ID NO 12
<211> LENGTH: 57
<212> TYPE: DNA
<213> ORGANISM: Artificial Sequence
<220> FEATURE:
<223> OTHER INFORMATION: Substrate etc

<400> SEQUENCE: 12
```

| | |
|---|---|
| tctagaggcc agcctggcca taaggagata tacatcggta ctgttggtaa agccacc | 57 |

```
<210> SEQ ID NO 13
<211> LENGTH: 50
<212> TYPE: DNA
<213> ORGANISM: Artificial Sequence
<220> FEATURE:
<223> OTHER INFORMATION: Substrate etc

<400> SEQUENCE: 13
```

| | |
|---|---|
| taatgaggcc aaactggcca ccatcaccat cagagcttgg actttcctcc | 50 |

```
<210> SEQ ID NO 14
<211> LENGTH: 2673
<212> TYPE: DNA
<213> ORGANISM: Artificial Sequence
<220> FEATURE:
<223> OTHER INFORMATION: T7RNAP variant

<400> SEQUENCE: 14
```

| | |
|---|---|
| atgcaccatc accatcacca tatgaacacg attaacatcg ctaagaacga cttctctgac | 60 |
| atcgaactgg ctgctatccc gttcaacact ctggctgacc attacggtga gcgtttagct | 120 |
| cgcgaacagt tggcccttga gcatgagtct tacgagatgg gtgaagcacg cttccgcaag | 180 |
| atgtttgagc gtcaacttaa agctggtgag gttgcggata cgctgccgc caagcctctc | 240 |
| atcactaccc tactccctaa gatgattgca cgcatcaacg actggtttga ggaagtgaaa | 300 |
| gctaagcgcg gcaagcgccc gacagccttc cagttcctgc aagaaatcaa gccggaagcc | 360 |
| gtagcgtaca tcaccattaa gaccactctg gcttgcctaa ccagtgctga caatacaacc | 420 |
| gttcaggctg tagcaagcgc aatcggtcgg gccattgagg acgaggctcg cttcggtcgt | 480 |
| atccgtgacc ttgaagctaa gcacttcaag aaaaacgttg aggaacaact caacaagcgc | 540 |
| gtagggcacg tctacaagaa agcatttatg caagttgtcg aggctgacat gctctctaag | 600 |
| ggtctactcg gtggcgaggc gtggtcttcg tggcataagg aagactctat tcatgtagga | 660 |
| gtacgctgca tcgagatgct cattgagtca accggaatgg ttagcttaca ccgccaaaat | 720 |
| gctggcgtag taggtcaaga ctctgagact atcgaactcg cacctgaata cgctgaggct | 780 |
| atcgcaaccc gtgcaggtgc gctggctggc atctctccga tgttccaacc ttgcgtagtt | 840 |
| cctcctaagc cgtggactgg cattactggt ggtggctatt gggctaacgg tcgtcgtcct | 900 |
| ctggcgctgg tgcgtactca cagtaagaaa gcactgatgc gctacgaaga cgtttacatg | 960 |
| cctgaggtgt acaaagcgat taacattgcg caaacaccg catggaaaat caacaagaaa | 1020 |
| gtcctagcgg tcgccaacgt aatcaccaag tggaagcatt gtccggtcga ggacatccct | 1080 |

```
gcgattgagc gtgaagaact cccgatgaaa ccggaagaca tcgacatgaa tcctgaggct   1140
ctcaccgcgt ggaaacgtgc tgccgctgct gtgtaccgca aggacaaggc tcgcaagtct   1200
cgccgtatca gccttgagtt catgcttgag caagccaata agtttgctaa ccataaggcc   1260
atctggttcc cttacaacat ggactggcgc ggtcgtgttt acgctgtgtc aatgttcaac   1320
ccgcaaggta acgatatgac caaaggactg cttacgctgg cgaaaggtaa accaatcggt   1380
aaggaaggtt actactggct gaaaatccac ggtgcaaact gtgcgggtgt cgataaggtt   1440
ccgttccctg agcgcatcaa gttcattgag gaaaaccacg agaacatcat ggcttgcgct   1500
aagtctccac tggagaacac ttggtgggct gagcaagatt ctccgttctg cttccttgcg   1560
ttctgctttg agtacgctgg ggtacagcac cacggcctga gctataactg ctcccttccg   1620
ctggcgtttg acgggtcttg ctctggcatc cagcacttct ccgcgatgct ccgagatgag   1680
gtaggtggtc gcgcggttaa cttgcttcct agtgaaaccg ttcaggacat ctacgggatt   1740
gttgctaaga agtcaacga gattctacaa gcagacgcaa tcaatgggac cgataacgaa   1800
gtagttaccg tgaccgatga gaacactggt gaaatctctg agaaagtcaa gctgggcact   1860
aaggcactgg ctggtcaatg gctggcttac ggtgttactc gcagtgtgac taagcgttca   1920
gtcatgacgc tggcttacgg gtccaaagag ttcggcttcc gtcaacaagt gctggaagat   1980
accattcagt gggctattga ttccggcaag ggtctgatgt tcactcagcc gaatcaggct   2040
gctggataca tggctaagct gatttgggaa tctgtgagcg tgacggtggt agctgcggtt   2100
gaagcaatga actggcttaa gtctgctgct aagctgctgg ctgctgaggt caaagataag   2160
aagactggag agattcttcg caagcgttgc gctgtgcatt gggtaactcc tgatggtttc   2220
cctgtgtggc aggaatacaa gaagcctatt cagacgcgct tgaacctgat gttcctcggt   2280
cagttccgct acagcctac cattaacacc aacaaagata gcgagattga tgcacacaaa   2340
caggagtctg gtatcgctcc taactttgta cacagccaag acggtagcca ccttcgtaag   2400
actgtagtgt gggcacacga gaagtacgga atcgaatctt ttgcactgat tcacgactcc   2460
ttcggtacca ttccggctga cgctgcgaac ctgttcaaag cagtgcgcga aactatggtt   2520
gacacatatg agtcttgtga tgtactggct gatttctacg accagttcgc tgaccagttg   2580
cacgagtctc aattggacaa aatgccagca cttccggcta aaggtaactt gaacctccgt   2640
gacatcttag agtcggactt cgcgttcgcg taa                                2673
```

<210> SEQ ID NO 15
<211> LENGTH: 890
<212> TYPE: PRT
<213> ORGANISM: Artificial Sequence
<220> FEATURE:
<223> OTHER INFORMATION: T7RNAP variant

<400> SEQUENCE: 15

Met His His His His His His Met Asn Thr Ile Asn Ile Ala Lys Asn
1               5                   10                  15

Asp Phe Ser Asp Ile Glu Leu Ala Ala Ile Pro Phe Asn Thr Leu Ala
            20                  25                  30

Asp His Tyr Gly Glu Arg Leu Ala Arg Glu Gln Leu Ala Leu Glu His
        35                  40                  45

Glu Ser Tyr Glu Met Gly Glu Ala Arg Phe Arg Lys Met Phe Glu Arg
    50                  55                  60

Gln Leu Lys Ala Gly Glu Val Ala Asp Asn Ala Ala Ala Lys Pro Leu
65                  70                  75                  80

```
Ile Thr Thr Leu Leu Pro Lys Met Ile Ala Arg Ile Asn Asp Trp Phe
                85              90              95

Glu Glu Val Lys Ala Lys Arg Gly Lys Arg Pro Thr Ala Phe Gln Phe
            100             105             110

Leu Gln Glu Ile Lys Pro Glu Ala Val Ala Tyr Ile Thr Ile Lys Thr
            115             120             125

Thr Leu Ala Cys Leu Thr Ser Ala Asp Asn Thr Thr Val Gln Ala Val
130             135             140

Ala Ser Ala Ile Gly Arg Ala Ile Glu Asp Glu Ala Arg Phe Gly Arg
145                 150             155             160

Ile Arg Asp Leu Glu Ala Lys His Phe Lys Lys Asn Val Glu Glu Gln
                165             170             175

Leu Asn Lys Arg Val Gly His Val Tyr Lys Lys Ala Phe Met Gln Val
            180             185             190

Val Glu Ala Asp Met Leu Ser Lys Gly Leu Leu Gly Gly Glu Ala Trp
            195             200             205

Ser Ser Trp His Lys Glu Asp Ser Ile His Val Gly Val Arg Cys Ile
        210             215             220

Glu Met Leu Ile Glu Ser Thr Gly Met Val Ser Leu His Arg Gln Asn
225             230             235             240

Ala Gly Val Val Gly Gln Asp Ser Glu Thr Ile Glu Leu Ala Pro Glu
                245             250             255

Tyr Ala Glu Ala Ile Ala Thr Arg Ala Gly Ala Leu Ala Gly Ile Ser
                260             265             270

Pro Met Phe Gln Pro Cys Val Val Pro Lys Pro Trp Thr Gly Ile
                275             280             285

Thr Gly Gly Gly Tyr Trp Ala Asn Gly Arg Arg Pro Leu Ala Leu Val
            290             295             300

Arg Thr His Ser Lys Lys Ala Leu Met Arg Tyr Glu Asp Val Tyr Met
305             310             315             320

Pro Glu Val Tyr Lys Ala Ile Asn Ile Ala Gln Asn Thr Ala Trp Lys
                325             330             335

Ile Asn Lys Lys Val Leu Ala Val Ala Asn Val Ile Thr Lys Trp Lys
            340             345             350

His Cys Pro Val Glu Asp Ile Pro Ala Ile Glu Arg Glu Glu Leu Pro
        355             360             365

Met Lys Pro Glu Asp Ile Asp Met Asn Pro Glu Ala Leu Thr Ala Trp
    370             375             380

Lys Arg Ala Ala Ala Val Tyr Arg Lys Asp Lys Ala Arg Lys Ser
385             390             395             400

Arg Arg Ile Ser Leu Glu Phe Met Leu Glu Gln Ala Asn Lys Phe Ala
                405             410             415

Asn His Lys Ala Ile Trp Phe Pro Tyr Asn Met Asp Trp Arg Gly Arg
            420             425             430

Val Tyr Ala Val Ser Met Phe Asn Pro Gln Gly Asn Asp Met Thr Lys
            435             440             445

Gly Leu Leu Thr Leu Ala Lys Gly Lys Pro Ile Gly Lys Glu Gly Tyr
450             455             460

Tyr Trp Leu Lys Ile His Gly Ala Asn Cys Ala Gly Val Asp Lys Val
465             470             475             480

Pro Phe Pro Glu Arg Ile Lys Phe Ile Glu Glu Asn His Glu Asn Ile
                485             490             495
```

Met Ala Cys Ala Lys Ser Pro Leu Glu Asn Thr Trp Trp Ala Glu Gln
              500                 505                 510

Asp Ser Pro Phe Cys Phe Leu Ala Phe Cys Phe Glu Tyr Ala Gly Val
        515                 520                 525

Gln His His Gly Leu Ser Tyr Asn Cys Ser Leu Pro Leu Ala Phe Asp
    530                 535                 540

Gly Ser Cys Ser Gly Ile Gln His Phe Ser Ala Met Leu Arg Asp Glu
545                 550                 555                 560

Val Gly Gly Arg Ala Val Asn Leu Leu Pro Ser Glu Thr Val Gln Asp
                565                 570                 575

Ile Tyr Gly Ile Val Ala Lys Lys Val Asn Glu Ile Leu Gln Ala Asp
            580                 585                 590

Ala Ile Asn Gly Thr Asp Asn Glu Val Thr Val Thr Asp Glu Asn
        595                 600                 605

Thr Gly Glu Ile Ser Glu Lys Val Lys Leu Gly Thr Lys Ala Leu Ala
    610                 615                 620

Gly Gln Trp Leu Ala Tyr Gly Val Thr Arg Ser Val Thr Lys Arg Ser
625                 630                 635                 640

Val Met Thr Leu Ala Tyr Gly Ser Lys Glu Phe Gly Phe Arg Gln Gln
                645                 650                 655

Val Leu Glu Asp Thr Ile Gln Trp Ala Ile Asp Ser Gly Lys Gly Leu
            660                 665                 670

Met Phe Thr Gln Pro Asn Gln Ala Gly Tyr Met Ala Lys Leu Ile
        675                 680                 685

Trp Glu Ser Val Ser Val Thr Val Val Ala Ala Val Glu Ala Met Asn
690                 695                 700

Trp Leu Lys Ser Ala Ala Lys Leu Leu Ala Ala Glu Val Lys Asp Lys
705                 710                 715                 720

Lys Thr Gly Glu Ile Leu Arg Lys Arg Cys Ala Val His Trp Val Thr
                725                 730                 735

Pro Asp Gly Phe Pro Val Trp Gln Glu Tyr Lys Lys Pro Ile Gln Thr
            740                 745                 750

Arg Leu Asn Leu Met Phe Leu Gly Gln Phe Arg Leu Gln Pro Thr Ile
        755                 760                 765

Asn Thr Asn Lys Asp Ser Glu Ile Asp Ala His Lys Gln Glu Ser Gly
    770                 775                 780

Ile Ala Pro Asn Phe Val His Ser Gln Asp Gly Ser His Leu Arg Lys
785                 790                 795                 800

Thr Val Val Trp Ala His Glu Lys Tyr Gly Ile Glu Ser Phe Ala Leu
                805                 810                 815

Ile His Asp Ser Phe Gly Thr Ile Pro Ala Asp Ala Ala Asn Leu Phe
            820                 825                 830

Lys Ala Val Arg Glu Thr Met Val Asp Thr Tyr Glu Ser Cys Asp Val
        835                 840                 845

Leu Ala Asp Phe Tyr Asp Gln Phe Ala Asp Gln Leu His Glu Ser Gln
    850                 855                 860

Leu Asp Lys Met Pro Ala Leu Pro Ala Lys Gly Asn Leu Asn Leu Arg
865                 870                 875                 880

Asp Ile Leu Glu Ser Asp Phe Ala Phe Ala
                885                 890

<210> SEQ ID NO 16
<211> LENGTH: 2673
<212> TYPE: DNA

<213> ORGANISM: Artificial Sequence
<220> FEATURE:
<223> OTHER INFORMATION: T7RNAP variant

<400> SEQUENCE: 16

```
atgcaccatc accatcacca tatgaacacg attaacatcg ctaagaacga cttctctgac      60
atcgaactgg ctgctatccc gttcaacact ctggctgacc attacggtga gcgtttagct     120
cgcgaacagt tggcccttga gcatgagtct tacgagatgg gtgaagcacg cttccgcaag     180
atgtttgagc gtcaacttaa agctggtgag gttgcggata acgctgccgc caagcctctc     240
atcactaccc tactccctaa gatgattgca cgcatcaacg actggtttga ggaagtgaaa     300
gctaagcgcg gcaagcgccc gacagccttc cagttcctgc aagaaatcaa gccggaagcc     360
gtagcgtaca tcaccattaa gaccactctg gcttgcctaa ccagtgctga taatacaacc     420
gttcaggctg tagcaagcgc aatcggtcgg gccattgagg acgaggctcg cttcggtcgt     480
atccgtgacc ttgaagctaa gcacttcaag aaaaacgttg aggaacaact caacaagcgc     540
gtagggcacg tctacaagaa agcatttatg caagttgtcg aggctgacat gctctctaag     600
ggtctactcg gtggcgaggc gtggtcttcg tggcataagg aagactctat tcatgtagga     660
gtacgctgca tcgagatgct cattgagtca accggaatgg ttagcttaca ccgccaaaat     720
gctggcgtag taggtcaaga ctctgagact atcgaactcg cacctgaata cgctgaggct     780
atcgcaaccc gtgcaggtgc gctggctggc atctctccga tgttccaacc ttgcgtagtt     840
cctcctaagc cgtggactgg cattactggt ggtggctatt gggctaacgg tcgtcgtcct     900
ctggcgctgg tgcgtactca cagtaagaaa gcactgatgc gctacgaaga cgtttacatg     960
cctgaggtgt acaaagcgat taacattgcg caaacaccg catggaaaat caacaagaaa    1020
gtcctagcgg tcgccaacgt aatcaccaag tggaagcatt gtccggtcga ggacatccct    1080
gcgattgagc gtgaagaact cccgatgaaa ccggaagaca tcgacatgaa tcctgaggct    1140
ctcaccgcgt ggaaacgtgc tgccgctgct gtgtaccgca aggacaaggc tcgcaagtct    1200
agacgtatca gccttgagtt catgcttgag caagccaata gtttgctaa ccataaggcc    1260
atctggttcc cttacaacat ggactggcgc ggtcgtgttt acgctgtgtc aatgttcaac    1320
ccgcaaggta acgatatgac caaaggactg cttacgctgg cgaaaggtaa accaatcggt    1380
aaggaaggtt actactggct gaaaatccac ggtgcaaact gtgcgggtgt cgataaggtt    1440
ccgttccctg agcgcatcaa gttcattgag gaaaaccacg agaacatcat ggcttgcgct    1500
aagtctccac tggagaacac ttggtgggct gagcaagatt ctccgttctg cttccttgcg    1560
ttctgctttg agtacgctgg ggtacagcac cacggcctga gctataactg ctcccttccg    1620
ctggcgtttg acgggtcttg ctctggcatc cagcacttct ccgcgatgct ccgagatgag    1680
gtaggtggtc gcgcggttaa cttgcttcct agtgaaaccg ttcaggacat ctacgggatt    1740
gttgctaaga agtcaacga gattctacaa gcagacgcaa tcaatgggac cgataacgaa    1800
gtagttaccg tgaccgatga aaacactggt gaaatctctg agaaagtcaa gctgggcact    1860
aaggcactgg ctggtcaatg gctggcttac ggtgttactc gctgggtgac aaagcgttca    1920
gtcatgacgc tggcttacgg tccaaagag ttcggcttcc gtcaacaagt gctgaaaacc    1980
accattcagt gggctattga ttccggcaag gtctgatgt tcactcagcc gaatcaggct    2040
gctggataca tggctaagct gattgggaa tctgtgagcg tgacggtggt agctgcggtt    2100
gaagcaatga ctggcttaa gtctgctgct aagctgctgg ctgctgaggt caaagataag    2160
aagactggag agattcttcg caagcgttgc gctgtgcatt gggtaactcc tgatggtttc    2220
```

-continued

```
cctgtgtggc aggaatacaa gaagcctatt cagacgcgct tgaacctgat gttcctcggt    2280
cagttccgct tacagcctac cattaacacc aacaaagata gcgagattga tgcacacaaa    2340
caggagtctg gtatcgctcc taactttgta cacagccaag acggtagcca ccttcgtaag    2400
actgtagtgt gggcacacga gaagtacgga atcgaatctt ttgcactgat tcacgactcc    2460
ttcggtacca ttccggctga cgctgcgaac ctgttcaaag cagtgcgcga aactatggtt    2520
gacacatatg agtcttgtga tgtactggct gatttctacg accagttcgc tgaccagttg    2580
cacgagtctc aattggacaa aatgccagca cttccggcta aaggtaactt gaacctccgt    2640
gacatcttag agtcggactt cgcgttcgcg taa                                 2673
```

<210> SEQ ID NO 17
<211> LENGTH: 890
<212> TYPE: PRT
<213> ORGANISM: Artificial Sequence
<220> FEATURE:
<223> OTHER INFORMATION: T7RNAP variant

<400> SEQUENCE: 17

```
Met His His His His His Met Asn Thr Ile Asn Ile Ala Lys Asn
1               5                   10                  15

Asp Phe Ser Asp Ile Glu Leu Ala Ala Ile Pro Phe Asn Thr Leu Ala
            20                  25                  30

Asp His Tyr Gly Glu Arg Leu Ala Arg Glu Gln Leu Ala Leu Glu His
        35                  40                  45

Glu Ser Tyr Glu Met Gly Glu Ala Arg Phe Arg Lys Met Phe Glu Arg
    50                  55                  60

Gln Leu Lys Ala Gly Glu Val Ala Asp Asn Ala Ala Ala Lys Pro Leu
65                  70                  75                  80

Ile Thr Thr Leu Leu Pro Lys Met Ile Ala Arg Ile Asn Asp Trp Phe
                85                  90                  95

Glu Glu Val Lys Ala Lys Arg Gly Lys Arg Pro Thr Ala Phe Gln Phe
            100                 105                 110

Leu Gln Glu Ile Lys Pro Glu Ala Val Ala Tyr Ile Thr Ile Lys Thr
        115                 120                 125

Thr Leu Ala Cys Leu Thr Ser Ala Asp Asn Thr Thr Val Gln Ala Val
    130                 135                 140

Ala Ser Ala Ile Gly Arg Ala Ile Glu Asp Glu Ala Arg Phe Gly Arg
145                 150                 155                 160

Ile Arg Asp Leu Glu Ala Lys His Phe Lys Lys Asn Val Glu Glu Gln
                165                 170                 175

Leu Asn Lys Arg Val Gly His Val Tyr Lys Lys Ala Phe Met Gln Val
            180                 185                 190

Val Glu Ala Asp Met Leu Ser Lys Gly Leu Leu Gly Gly Glu Ala Trp
        195                 200                 205

Ser Ser Trp His Lys Glu Asp Ser Ile His Val Gly Val Arg Cys Ile
    210                 215                 220

Glu Met Leu Ile Glu Ser Thr Gly Met Val Ser Leu His Arg Gln Asn
225                 230                 235                 240

Ala Gly Val Val Gly Gln Asp Ser Glu Thr Ile Glu Leu Ala Pro Glu
                245                 250                 255

Tyr Ala Glu Ala Ile Ala Thr Arg Ala Gly Ala Leu Ala Gly Ile Ser
            260                 265                 270

Pro Met Phe Gln Pro Cys Val Val Pro Pro Lys Pro Trp Thr Gly Ile
```

```
              275                 280                 285
Thr Gly Gly Tyr Trp Ala Asn Gly Arg Pro Leu Ala Leu Val
290                 295                 300

Arg Thr His Ser Lys Lys Ala Leu Met Arg Tyr Glu Asp Val Tyr Met
305                 310                 315                 320

Pro Glu Val Tyr Lys Ala Ile Asn Ile Ala Gln Asn Thr Ala Trp Lys
                325                 330                 335

Ile Asn Lys Lys Val Leu Ala Val Ala Asn Val Ile Thr Lys Trp Lys
                340                 345                 350

His Cys Pro Val Glu Asp Ile Pro Ala Ile Glu Arg Glu Glu Leu Pro
                355                 360                 365

Met Lys Pro Glu Asp Ile Asp Met Asn Pro Glu Ala Leu Thr Ala Trp
370                 375                 380

Lys Arg Ala Ala Ala Val Tyr Arg Lys Asp Lys Ala Arg Lys Ser
385                 390                 395                 400

Arg Arg Ile Ser Leu Glu Phe Met Leu Glu Gln Ala Asn Lys Phe Ala
                405                 410                 415

Asn His Lys Ala Ile Trp Phe Pro Tyr Asn Met Asp Trp Arg Gly Arg
                420                 425                 430

Val Tyr Ala Val Ser Met Phe Asn Pro Gln Gly Asn Asp Met Thr Lys
                435                 440                 445

Gly Leu Leu Thr Leu Ala Lys Gly Lys Pro Ile Gly Lys Glu Gly Tyr
450                 455                 460

Tyr Trp Leu Lys Ile His Gly Ala Asn Cys Ala Gly Val Asp Lys Val
465                 470                 475                 480

Pro Phe Pro Glu Arg Ile Lys Phe Ile Glu Glu Asn His Glu Asn Ile
                485                 490                 495

Met Ala Cys Ala Lys Ser Pro Leu Glu Asn Thr Trp Trp Ala Glu Gln
                500                 505                 510

Asp Ser Pro Phe Cys Phe Leu Ala Phe Cys Phe Glu Tyr Ala Gly Val
                515                 520                 525

Gln His His Gly Leu Ser Tyr Asn Cys Ser Leu Pro Leu Ala Phe Asp
                530                 535                 540

Gly Ser Cys Ser Gly Ile Gln His Phe Ser Ala Met Leu Arg Asp Glu
545                 550                 555                 560

Val Gly Gly Arg Ala Val Asn Leu Leu Pro Ser Glu Thr Val Gln Asp
                565                 570                 575

Ile Tyr Gly Ile Val Ala Lys Lys Val Asn Glu Ile Leu Gln Ala Asp
                580                 585                 590

Ala Ile Asn Gly Thr Asp Asn Glu Val Val Thr Val Thr Asp Glu Asn
                595                 600                 605

Thr Gly Glu Ile Ser Glu Lys Val Lys Leu Gly Thr Lys Ala Leu Ala
                610                 615                 620

Gly Gln Trp Leu Ala Tyr Gly Val Thr Arg Val Thr Lys Arg Ser
625                 630                 635                 640

Val Met Thr Leu Ala Tyr Gly Ser Lys Glu Phe Gly Phe Arg Gln Gln
                645                 650                 655

Val Leu Glu Thr Thr Ile Gln Trp Ala Ile Asp Ser Gly Lys Gly Leu
                660                 665                 670

Met Phe Thr Gln Pro Asn Gln Ala Ala Gly Tyr Met Ala Lys Leu Ile
                675                 680                 685

Trp Glu Ser Val Ser Val Thr Val Val Ala Ala Val Glu Ala Met Asn
690                 695                 700
```

```
Trp Leu Lys Ser Ala Ala Lys Leu Leu Ala Glu Val Lys Asp Lys
705                 710                 715                 720

Lys Thr Gly Glu Ile Leu Arg Lys Arg Cys Ala Val His Trp Val Thr
            725                 730                 735

Pro Asp Gly Phe Pro Val Trp Gln Glu Tyr Lys Lys Pro Ile Gln Thr
        740                 745                 750

Arg Leu Asn Leu Met Phe Leu Gly Gln Phe Arg Leu Gln Pro Thr Ile
    755                 760                 765

Asn Thr Asn Lys Asp Ser Glu Ile Asp Ala His Lys Gln Glu Ser Gly
770                 775                 780

Ile Ala Pro Asn Phe Val His Ser Gln Asp Gly Ser His Leu Arg Lys
785                 790                 795                 800

Thr Val Val Trp Ala His Glu Lys Tyr Gly Ile Glu Ser Phe Ala Leu
                805                 810                 815

Ile His Asp Ser Phe Gly Thr Ile Pro Ala Asp Ala Ala Asn Leu Phe
            820                 825                 830

Lys Ala Val Arg Glu Thr Met Val Asp Thr Tyr Glu Ser Cys Asp Val
        835                 840                 845

Leu Ala Asp Phe Tyr Asp Gln Phe Ala Asp Gln Leu His Glu Ser Gln
    850                 855                 860

Leu Asp Lys Met Pro Ala Leu Pro Ala Lys Gly Asn Leu Asn Leu Arg
865                 870                 875                 880

Asp Ile Leu Glu Ser Asp Phe Ala Phe Ala
                885                 890

<210> SEQ ID NO 18
<211> LENGTH: 2673
<212> TYPE: DNA
<213> ORGANISM: Artificial Sequence
<220> FEATURE:
<223> OTHER INFORMATION: T7RNAP variant

<400> SEQUENCE: 18
atgcaccatc accatcacca tatgaacacg attaacatcg ctaagaacga cttctctgac      60
atcgaactgg ctgctatccc gttcaacact ctggctgacc attacggtga gcgtttagct     120
cgcgaacagt tggcccttga gcatgagtct tacgagatgg gtgaagcacg cttccgcaag     180
atgtttgagc gtcaacttaa agctggtgag gttgcggata cgctgccgc caagcctctc     240 atcactaccc tactccctaa gatgattgca cgcatcaacg actggtttga ggaagtgaaa     300
gctaagcgcg gcaagcgccc gacagccttc cagttcctgc aagaaatcaa gccggaagcc     360
gtagcgtaca tcaccattaa gaccactctg gcttgcctaa ccagtgctga taatacaacc     420
gttcaggctg tagcaagcgc aatcggtcgg gccattgagg acgaggctcg cttcggtcgt     480
atccgtgacc ttgaagctaa gcacttcaag aaaaacgttg aggaacaact caacaagcgc     540
gtagggcacg tctacaagaa agcatttatg caagttgtcg aggctgacat gctctctaag     600
ggtctactcg gtggcgaggc gtggtcttcg tggcataagg aagactctat tcatgtagga     660
gtacgctgca tcgagatgct cattgagtca accggaatgg ttagcttaca ccgccaaaat     720
gctggcgtag taggtcaaga ctctgagact atcgaactcg cacctgaata cgctgaggct     780
atcgcaaccc gtgcaggtgc gctggctggc atctctccga tgttccaacc ttgcgtagtt     840
cctcctaagc gtggactgg cattactggt ggtggctatt gggctaacgg tcgtcgtcct     900
ctggcgctgg tgcgtactca cagtaagaaa gcactgatgc gctacgaaga cgtttacatg     960
```

```
cctgaggtgt acaaagcgat taacattgcg caaaacaccg catggaaaat caacaagaaa    1020
gtcctagcgg tcgccaacgt aatcaccaag tggaagcatt gtccggtcga ggacatccct    1080
gcgattgagc gtgaagaact cccgatgaaa ccggaagaca tcgacatgaa tcctgaggct    1140
ctcaccgcgt ggaaacgtgc tgccgctgct gtgtaccgca aggacaaggc tcgcaagtct    1200
cgccgtatca gccttgagtt catgcttgag caagccaata agtttgctaa ccataaggcc    1260
atctggttcc cttacaacat ggactggcgc ggtcgtgttt acgctgtgtc aatgttcaac    1320
ccgcaaggta acgatatgac caaaggactg cttacgctgg cgaaaggtaa accaatcggt    1380
aaggaaggtt actactggct gaaaatccac ggtgcaaact gtgcgggtgt cgataaggtt    1440
ccgttccctg agcgcatcaa gttcattgag gaaaaccacg agaacatcat ggcttgcgct    1500
aagtctccac tggagaacac ttggtgggct gagcaattgt ctccgttctg cttccttgcg    1560
ttctgctttg agtacgctgg ggtacagcac cacggcctga gctataactg ctcccttccg    1620
ctggcgtttg acgggtcttg ctctggcatc cagcacttct ccgcgatgct ccgagatgag    1680
gtaggtggtc gcgcggttaa cttgcttcct agtgaaaccg ttcaggacat ctacgggatt    1740
gttgctaaga agtcaacga gattctacaa gcagacgcaa tcaatgggac cgataacgaa    1800
gtagttaccg tgaccgatga aacactggt gaaatctctg agaaagtcaa gctgggcact    1860
aaggcactgg ctggtcaatg gctggcttac ggtgttactc gcagtgtgac taagcgttca    1920
gtcatgacgc tggcttacgg tccaaagag ttcggcttcc gtcaacaagt gctggaatgg    1980
accattcagt gggctattga ttccggcaag ggtctgatgt tcactcagcc gaatcaggct    2040
gctggataca tggctaagct gatttgggaa tctgtgagcg tgacggtggt agctgcggtt    2100
gaagcaatga actggcttaa gtctgctgct aagctgctgg ctgctgaggt caaagataag    2160
aagactggag agattcttcg caagcgttgc gctgtgcatt gggtaactcc tgatggtttc    2220
cctgtgtggc aggaatacaa gaagcctatt cagacgcgct tgaacctgat gttcctcggt    2280
cagttccgct tacagcctac cattaacacc aacaaagata gcgagattga tgcacacaaa    2340
caggagtctg gtatcgctcc taactttgta cacagccaag acggtagcca ccttcgtaag    2400
actgtagtgt gggcacacga gaagtacgga atcgaatctt ttgcactgat tcacgactcc    2460
ttcggtacca ttccggctga cgctgcgaac ctgttcaaag cagtgcgcga aactatggtt    2520
gacacatatg agtcttgtga tgtactggct gatttctacg accagttcgc tgaccagttg    2580
cacgagtctc aattggacaa aatgccagca cttccggcta aaggtaactt gaacctccgt    2640
gacatcttag agtcggactt cgcgttcgcg taa                                 2673
```

```
<210> SEQ ID NO 19
<211> LENGTH: 890
<212> TYPE: PRT
<213> ORGANISM: Artificial Sequence
<220> FEATURE:
<223> OTHER INFORMATION: T7RNAP variant

<400> SEQUENCE: 19

Met His His His His His Met Asn Thr Ile Asn Ile Ala Lys Asn
1               5                   10                  15

Asp Phe Ser Asp Ile Glu Leu Ala Ala Ile Pro Phe Asn Thr Leu Ala
            20                  25                  30

Asp His Tyr Gly Glu Arg Leu Ala Arg Glu Gln Leu Ala Leu Glu His
        35                  40                  45

Glu Ser Tyr Glu Met Gly Glu Ala Arg Phe Arg Lys Met Phe Glu Arg
    50                  55                  60
```

```
Gln Leu Lys Ala Gly Glu Val Ala Asp Asn Ala Ala Lys Pro Leu
 65                  70                  75                  80

Ile Thr Thr Leu Leu Pro Lys Met Ile Ala Arg Ile Asn Asp Trp Phe
                 85                  90                  95

Glu Glu Val Lys Ala Lys Arg Gly Lys Arg Pro Thr Ala Phe Gln Phe
                100                 105                 110

Leu Gln Glu Ile Lys Pro Glu Ala Val Ala Tyr Ile Thr Ile Lys Thr
            115                 120                 125

Thr Leu Ala Cys Leu Thr Ser Ala Asp Asn Thr Thr Val Gln Ala Val
        130                 135                 140

Ala Ser Ala Ile Gly Arg Ala Ile Glu Asp Ala Arg Phe Gly Arg
145                 150                 155                 160

Ile Arg Asp Leu Glu Ala Lys His Phe Lys Lys Asn Val Glu Glu Gln
                165                 170                 175

Leu Asn Lys Arg Val Gly His Val Tyr Lys Lys Ala Phe Met Gln Val
                180                 185                 190

Val Glu Ala Asp Met Leu Ser Lys Gly Leu Leu Gly Glu Ala Trp
        195                 200                 205

Ser Ser Trp His Lys Glu Asp Ser Ile His Val Gly Val Arg Cys Ile
210                 215                 220

Glu Met Leu Ile Glu Ser Thr Gly Met Val Ser Leu His Arg Gln Asn
225                 230                 235                 240

Ala Gly Val Val Gly Gln Asp Ser Glu Thr Ile Glu Leu Ala Pro Glu
                245                 250                 255

Tyr Ala Glu Ala Ile Ala Thr Arg Ala Gly Ala Leu Ala Gly Ile Ser
                260                 265                 270

Pro Met Phe Gln Pro Cys Val Val Pro Pro Lys Pro Trp Thr Gly Ile
            275                 280                 285

Thr Gly Gly Gly Tyr Trp Ala Asn Gly Arg Arg Pro Leu Ala Leu Val
        290                 295                 300

Arg Thr His Ser Lys Lys Ala Leu Met Arg Tyr Glu Asp Val Tyr Met
305                 310                 315                 320

Pro Glu Val Tyr Lys Ala Ile Asn Ile Ala Gln Asn Thr Ala Trp Lys
                325                 330                 335

Ile Asn Lys Lys Val Leu Ala Val Ala Asn Val Ile Thr Lys Trp Lys
            340                 345                 350

His Cys Pro Val Glu Asp Ile Pro Ala Ile Glu Arg Glu Glu Leu Pro
        355                 360                 365

Met Lys Pro Glu Asp Ile Asp Met Asn Pro Glu Ala Leu Thr Ala Trp
    370                 375                 380

Lys Arg Ala Ala Ala Val Tyr Arg Lys Asp Lys Ala Arg Lys Ser
385                 390                 395                 400

Arg Arg Ile Ser Leu Glu Phe Met Leu Glu Gln Ala Asn Lys Phe Ala
                405                 410                 415

Asn His Lys Ala Ile Trp Phe Pro Tyr Asn Met Asp Trp Arg Gly Arg
                420                 425                 430

Val Tyr Ala Val Ser Met Phe Asn Pro Gln Gly Asn Asp Met Thr Lys
                435                 440                 445

Gly Leu Leu Thr Leu Ala Lys Gly Lys Pro Ile Gly Lys Glu Gly Tyr
            450                 455                 460

Tyr Trp Leu Lys Ile His Gly Ala Asn Cys Ala Gly Val Asp Lys Val
465                 470                 475                 480
```

```
Pro Phe Pro Glu Arg Ile Lys Phe Ile Glu Glu Asn His Glu Asn Ile
                485                 490                 495
Met Ala Cys Ala Lys Ser Pro Leu Glu Asn Thr Trp Trp Ala Glu Gln
            500                 505                 510
Leu Ser Pro Phe Cys Phe Leu Ala Phe Cys Phe Glu Tyr Ala Gly Val
            515                 520                 525
Gln His His Gly Leu Ser Tyr Asn Cys Ser Leu Pro Leu Ala Phe Asp
            530                 535                 540
Gly Ser Cys Ser Gly Ile Gln His Phe Ser Ala Met Leu Arg Asp Glu
545                 550                 555                 560
Val Gly Gly Arg Ala Val Asn Leu Leu Pro Ser Glu Thr Val Gln Asp
                565                 570                 575
Ile Tyr Gly Ile Val Ala Lys Lys Val Asn Glu Ile Leu Gln Ala Asp
                580                 585                 590
Ala Ile Asn Gly Thr Asp Asn Glu Val Val Thr Val Thr Asp Glu Asn
                595                 600                 605
Thr Gly Glu Ile Ser Glu Lys Val Lys Leu Gly Thr Lys Ala Leu Ala
            610                 615                 620
Gly Gln Trp Leu Ala Tyr Gly Val Thr Arg Ser Val Thr Lys Arg Ser
625                 630                 635                 640
Val Met Thr Leu Ala Tyr Gly Ser Lys Glu Phe Gly Phe Arg Gln Gln
                645                 650                 655
Val Leu Glu Trp Thr Ile Gln Trp Ala Ile Asp Ser Gly Lys Gly Leu
                660                 665                 670
Met Phe Thr Gln Pro Asn Gln Ala Ala Gly Tyr Met Ala Lys Leu Ile
            675                 680                 685
Trp Glu Ser Val Ser Val Thr Val Val Ala Ala Val Glu Ala Met Asn
690                 695                 700
Trp Leu Lys Ser Ala Ala Lys Leu Leu Ala Ala Glu Val Lys Asp Lys
705                 710                 715                 720
Lys Thr Gly Glu Ile Leu Arg Lys Arg Cys Ala Val His Trp Val Thr
                725                 730                 735
Pro Asp Gly Phe Pro Val Trp Gln Glu Tyr Lys Lys Pro Ile Gln Thr
            740                 745                 750
Arg Leu Asn Leu Met Phe Leu Gly Gln Phe Arg Leu Gln Pro Thr Ile
            755                 760                 765
Asn Thr Asn Lys Asp Ser Glu Ile Asp Ala His Lys Gln Glu Ser Gly
            770                 775                 780
Ile Ala Pro Asn Phe Val His Ser Gln Asp Gly Ser His Leu Arg Lys
785                 790                 795                 800
Thr Val Val Trp Ala His Glu Lys Tyr Gly Ile Glu Ser Phe Ala Leu
                805                 810                 815
Ile His Asp Ser Phe Gly Thr Ile Pro Ala Asp Ala Ala Asn Leu Phe
                820                 825                 830
Lys Ala Val Arg Glu Thr Met Val Asp Thr Tyr Glu Ser Cys Asp Val
                835                 840                 845
Leu Ala Asp Phe Tyr Asp Gln Phe Ala Asp Gln Leu His Glu Ser Gln
850                 855                 860
Leu Asp Lys Met Pro Ala Leu Pro Ala Lys Gly Asn Leu Asn Leu Arg
865                 870                 875                 880
Asp Ile Leu Glu Ser Asp Phe Ala Phe Ala
                885                 890
```

```
<210> SEQ ID NO 20
<211> LENGTH: 2673
<212> TYPE: DNA
<213> ORGANISM: Artificial Sequence
<220> FEATURE:
<223> OTHER INFORMATION: T7RNAP variant

<400> SEQUENCE: 20
atgcaccatc accatcacca tatgaacacg attaacatcg ctaagaacga cttctctgac      60
atcgaactgg ctgctatccc gttcaacact ctggctgacc attacggtga gcgtttagct     120
cgcgaacagt tggcccttga gcatgagtct tacgagatgg gtgaagcacg cttccgcaag     180
atgtttgagc gtcaacttaa agctggtgag gttgcggata cgctgccgc caagcctctc     240 atcactaccc tactccctaa gatgattgca cgcatcaacg actggtttga ggaagtgaaa     300
gctaagcgcg gcaagcgccc gacagccttc cagttcctgc aagaaatcaa gccggaagcc     360
gtagcgtaca tcaccattaa gaccactctg gcttgcctaa ccagtgcttg aatacaacc      420 gttcaggctg tagcaagcgc aatcggtcgg gccattgagg acgaggctcg cttcggtcgt     480
atccgtgacc ttgaagctaa gcacttcaag aaaaacgttg aggaacaact caacaagcgc     540
gtagggcacg tctacaagaa agcatttatg caagttgtcg aggctgacat gctctctaag     600
ggtctactcg gtggcgaggc gtggtcttcg tggcataagg aagactctat tcatgtagga     660
gtacgctgca tcgagatgct cattgagtca accggaatgg ttagcttaca ccgccaaaat     720
gctggcgtag taggtcaaga ctctgagact atcgaactcg cacctgaata cgctgaggct     780
atcgcaaccc gtgcaggtgc gctggctggc atctctccga tgttccaacc ttgcgtagtt     840
cctcctaagc cgtggactgg cattactggt ggtggctatt gggctaacgg tcgtcgtcct     900
ctggcgctgg tgcgtactca cagtaagaaa gcactgatgc gctacgaaga cgtttacatg     960
cctgaggtgt acaaagcgat taacattgcg caaacaccg catggaaaat caacaagaaa    1020
gtcctagcgg tcgccaacgt aatcaccaag tggaagcatt gtccggtcga ggacatccct    1080
gcgattgagc gtgaagaact cccgatgaaa ccggaagaca tcgacatgaa tcctgaggct    1140
ctcaccgcgt ggaaacgtgc tgccgctgct gtgtaccgca aggacaaggc tcgcaagtct    1200
agtcgtatca gccttgagtt catgcttgag caagccaata gtttgctaa ccataaggcc     1260 atctggttcc cttacaacat ggactggcgc ggtcgtgttt acgctgtgtc aatgttcaac    1320
ccgcaaggta acgatatgac caaaggactg cttacgctgg cgaaaggtaa accaatcggt    1380
aaggaaggtt actactggct gaaaatccac ggtgcaaact gtgcgggtgt cgataaggtt    1440
ccgttccctg agcgcatcaa gttcattgag gaaaccacg agaacatcat ggcttgcgct    1500
aagtctccac tggagaacac ttggtgggct gagcaacggt ctccgttctg cttccttgcg    1560
ttctgctttg agtacgctgg ggtacagcac acggcctga gctataactg ctcccttccg    1620
ctggcgtttg acgggtcttg ctctggcatc cagcacttct ccgcgatgct ccgagatgag    1680
gtaggtggtc gcgcggttaa cttgcttcct agtgaaaccg ttcaggacat ctacgggatt    1740
gttgctaaga aagtcaacga gattctacaa gcagacgcaa tcaatgggac cgataacgaa    1800
gtagttaccg tgaccgatga gaacactggt gaaatctctg agaaagtcaa gctgggcact    1860
aaggcactgg ctggtcaatg gctggcttac ggtgttactc gcagtgtgac taagcgttca    1920
gtcatgacgc tggcttacgg gtccaaagag ttcggcttcc gtcaacaagt gctggaagat    1980
accattcagt gggctattga ttccggcaag ggtctgatgt tcactcagcc gaatcaggct    2040
gctggataca tggctaagct gatttgggaa tctgtgagcg tgacggtggt agctgcggtt    2100
```

```
gaagcaatga actggcttaa gtctgctgct aagctgctgg ctgctgaggt caaagataag    2160
aagactggag agattcttcg caagcgttgc gctgtgcatt gggtaactcc tgatggtttc    2220
cctgtgtggc aggaatacaa gaagcctatt cagacgcgct tgaacctgat gttcctcggt    2280
cagttccgct tacagcctac cattaacacc aacaaagata gcgagattga tgcacacaaa    2340
caggagtctg gtatcgctcc taactttgta cacagccaag acggtagcca ccttcgtaag    2400
actgtagtgt gggcacacga gaagtacgga atcgaatctt ttgcactgat tcacgactcc    2460
ttcggtacca ttccggctga cgctgcgaac ctgttcaaag cagtgcgcga aactatggtt    2520
gacacatatg agtcttgtga tgtactggct gatttctacg accagttcgc tgaccagttg    2580
cacgagtctc aattggacaa aatgccagca cttccggcta aaggtaactt gaacctccgt    2640
gacatcttag agtcggactt cgcgttcgcg taa                                 2673
```

<210> SEQ ID NO 21
<211> LENGTH: 890
<212> TYPE: PRT
<213> ORGANISM: Artificial Sequence
<220> FEATURE:
<223> OTHER INFORMATION: T7RNAP variant

<400> SEQUENCE: 21

```
Met His His His His His His Met Asn Thr Ile Asn Ile Ala Lys Asn
1               5                   10                  15

Asp Phe Ser Asp Ile Glu Leu Ala Ala Ile Pro Phe Asn Thr Leu Ala
            20                  25                  30

Asp His Tyr Gly Glu Arg Leu Ala Arg Glu Gln Leu Ala Leu Glu His
        35                  40                  45

Glu Ser Tyr Glu Met Gly Glu Ala Arg Phe Arg Lys Met Phe Glu Arg
    50                  55                  60

Gln Leu Lys Ala Gly Glu Val Ala Asp Asn Ala Ala Ala Lys Pro Leu
65                  70                  75                  80

Ile Thr Thr Leu Leu Pro Lys Met Ile Ala Arg Ile Asn Asp Trp Phe
                85                  90                  95

Glu Glu Val Lys Ala Lys Arg Gly Lys Arg Pro Thr Ala Phe Gln Phe
            100                 105                 110

Leu Gln Glu Ile Lys Pro Glu Ala Val Ala Tyr Ile Thr Ile Lys Thr
        115                 120                 125

Thr Leu Ala Cys Leu Thr Ser Ala Trp Asn Thr Thr Val Gln Ala Val
    130                 135                 140

Ala Ser Ala Ile Gly Arg Ala Ile Glu Asp Glu Ala Arg Phe Gly Arg
145                 150                 155                 160

Ile Arg Asp Leu Glu Ala Lys His Phe Lys Lys Asn Val Glu Glu Gln
                165                 170                 175

Leu Asn Lys Arg Val Gly His Val Tyr Lys Lys Ala Phe Met Gln Val
            180                 185                 190

Val Glu Ala Asp Met Leu Ser Lys Gly Leu Leu Gly Gly Glu Ala Trp
        195                 200                 205

Ser Ser Trp His Lys Glu Asp Ser Ile His Val Gly Val Arg Cys Ile
    210                 215                 220

Glu Met Leu Ile Glu Ser Thr Gly Met Val Ser Leu His Arg Gln Asn
225                 230                 235                 240

Ala Gly Val Val Gly Gln Asp Ser Glu Thr Ile Glu Leu Ala Pro Glu
                245                 250                 255

Tyr Ala Glu Ala Ile Ala Thr Arg Ala Gly Ala Leu Ala Gly Ile Ser
```

```
            260                 265                 270
Pro Met Phe Gln Pro Cys Val Val Pro Pro Lys Pro Trp Thr Gly Ile
        275                 280                 285

Thr Gly Gly Gly Tyr Trp Ala Asn Gly Arg Arg Pro Leu Ala Leu Val
    290                 295                 300

Arg Thr His Ser Lys Lys Ala Leu Met Arg Tyr Glu Asp Val Tyr Met
305                 310                 315                 320

Pro Glu Val Tyr Lys Ala Ile Asn Ile Ala Gln Asn Thr Ala Trp Lys
                325                 330                 335

Ile Asn Lys Lys Val Leu Ala Val Ala Asn Val Ile Thr Lys Trp Lys
                340                 345                 350

His Cys Pro Val Glu Asp Ile Pro Ala Ile Glu Arg Glu Glu Leu Pro
            355                 360                 365

Met Lys Pro Glu Asp Ile Asp Met Asn Pro Glu Ala Leu Thr Ala Trp
        370                 375                 380

Lys Arg Ala Ala Ala Val Tyr Arg Lys Asp Lys Ala Arg Lys Ser
385                 390                 395                 400

Ser Arg Ile Ser Leu Glu Phe Met Leu Glu Gln Ala Asn Lys Phe Ala
                405                 410                 415

Asn His Lys Ala Ile Trp Phe Pro Tyr Asn Met Asp Trp Arg Gly Arg
                420                 425                 430

Val Tyr Ala Val Ser Met Phe Asn Pro Gln Gly Asn Asp Met Thr Lys
            435                 440                 445

Gly Leu Leu Thr Leu Ala Lys Gly Lys Pro Ile Gly Lys Glu Gly Tyr
        450                 455                 460

Tyr Trp Leu Lys Ile His Gly Ala Asn Cys Ala Gly Val Asp Lys Val
465                 470                 475                 480

Pro Phe Pro Glu Arg Ile Lys Phe Ile Glu Glu Asn His Glu Asn Ile
                485                 490                 495

Met Ala Cys Ala Lys Ser Pro Leu Glu Asn Thr Trp Trp Ala Glu Gln
            500                 505                 510

Arg Ser Pro Phe Cys Phe Leu Ala Phe Cys Phe Glu Tyr Ala Gly Val
        515                 520                 525

Gln His His Gly Leu Ser Tyr Asn Cys Ser Leu Pro Leu Ala Phe Asp
        530                 535                 540

Gly Ser Cys Ser Gly Ile Gln His Phe Ser Ala Met Leu Arg Asp Glu
545                 550                 555                 560

Val Gly Gly Arg Ala Val Asn Leu Leu Pro Ser Glu Thr Val Gln Asp
                565                 570                 575

Ile Tyr Gly Ile Val Ala Lys Lys Val Asn Glu Ile Leu Gln Ala Asp
                580                 585                 590

Ala Ile Asn Gly Thr Asp Asn Glu Val Val Thr Val Thr Asp Glu Asn
            595                 600                 605

Thr Gly Glu Ile Ser Glu Lys Val Lys Leu Gly Thr Lys Ala Leu Ala
        610                 615                 620

Gly Gln Trp Leu Ala Tyr Gly Val Thr Arg Ser Val Thr Lys Arg Ser
625                 630                 635                 640

Val Met Thr Leu Ala Tyr Gly Ser Lys Glu Phe Gly Phe Arg Gln Gln
                645                 650                 655

Val Leu Glu Asp Thr Ile Gln Trp Ala Ile Asp Ser Gly Lys Gly Leu
                660                 665                 670

Met Phe Thr Gln Pro Asn Gln Ala Ala Gly Tyr Met Ala Lys Leu Ile
            675                 680                 685
```

```
Trp Glu Ser Val Ser Val Thr Val Ala Ala Val Glu Ala Met Asn
    690             695                 700

Trp Leu Lys Ser Ala Ala Lys Leu Leu Ala Ala Glu Val Lys Asp Lys
705             710             715                 720

Lys Thr Gly Glu Ile Leu Arg Lys Arg Cys Ala Val His Trp Val Thr
                725             730                 735

Pro Asp Gly Phe Pro Val Trp Gln Glu Tyr Lys Lys Pro Ile Gln Thr
            740             745             750

Arg Leu Asn Leu Met Phe Leu Gly Gln Phe Arg Leu Gln Pro Thr Ile
        755             760             765

Asn Thr Asn Lys Asp Ser Glu Ile Asp Ala His Lys Gln Glu Ser Gly
        770             775             780

Ile Ala Pro Asn Phe Val His Ser Gln Asp Gly Ser His Leu Arg Lys
785             790             795                 800

Thr Val Val Trp Ala His Glu Lys Tyr Gly Ile Glu Ser Phe Ala Leu
                805             810             815

Ile His Asp Ser Phe Gly Thr Ile Pro Ala Asp Ala Ala Asn Leu Phe
            820             825             830

Lys Ala Val Arg Glu Thr Met Val Asp Thr Tyr Glu Ser Cys Asp Val
            835             840             845

Leu Ala Asp Phe Tyr Asp Gln Phe Ala Asp Gln Leu His Glu Ser Gln
850             855             860

Leu Asp Lys Met Pro Ala Leu Pro Ala Lys Gly Asn Leu Asn Leu Arg
865             870             875             880

Asp Ile Leu Glu Ser Asp Phe Ala Phe Ala
            885             890

<210> SEQ ID NO 22
<211> LENGTH: 2673
<212> TYPE: DNA
<213> ORGANISM: Artificial Sequence
<220> FEATURE:
<223> OTHER INFORMATION: T7RNAP variant

<400> SEQUENCE: 22
atgcaccatc accatcacca tatgaacacg attaacatcg ctaagaacga cttctctgac      60
atcgaactgg ctgctatccc gttcaacact ctggctgacc attacggtga gcgtttagct     120
cgcgaacagt tggcccttga gcatgagtct tacgagatgg gtgaagcacg cttccgcaag     180
atgtttgagc gtcaacttaa agctggtgag gttgcggata cgctgccgc caagcctctc     240 atcactaccc tactccctaa gatgattgca cgcatcaacg actggtttga ggaagtgaaa     300
gctaagcgcg gcaagcgccc gacagccttc cagttcctgc aagaaatcaa gccggaagcc     360
gtagcgtaca tcaccattaa gaccactctg gcttgcctaa ccagtgcttg aatacaacc      420 gttcaggctg tagcaagcgc aatcggtcgg gccattgagg acgaggctcg cttcggtcgt     480
atccgtgacc ttgaagctaa gcacttcaag aaaaacgttg aggaacaact caacaagcgc     540
gtagggcacg tctacaagaa agcatttatg caagttgtcg aggctgacat gctctctaag     600
ggtctactcg gtggcgaggc gtggtcttcg tggcataagg aagactctat tcatgtagga     660
gtacgctgca tcgagatgct cattgagtca accggaatgg ttagcttaca ccgccaaaat     720
gctggcgtag taggtcaaga ctctgagact atcgaactcg cacctgaata cgctgaggct     780
atcgcaaccc gtgcaggtgc gctggctggc atctctccga tgttccaacc ttgcgtagtt     840
cctcctaagc gtggactgg cattactggt ggtggctatt gggctaacgg tcgtcgtcct     900
```

```
ctggcgctgg tgcgtactca cagtaagaaa gcactgatgc gctacgaaga cgtttacatg   960
cctgaggtgt acaaagcgat taacattgcg caaaacaccg catggaaaat caacaagaaa  1020
gtcctagcgg tcgccaacgt aatcaccaag tggaagcatt gtccggtcga ggacatccct  1080
gcgattgagc gtgaagaact cccgatgaaa ccggaagaca tcgacatgaa tcctgaggct  1140
ctcaccgcgt ggaaacgtgc tgccgctgct gtgtaccgca aggacaaggc tcgcaagtct  1200
agacgtatca gccttgagtt catgcttgag caagccaata gtttgctaa ccataaggcc   1260
atctggttcc cttacaacat ggactggcgc ggtcgtgttt acgctgtgtc aatgttcaac  1320
ccgcaaggta acgatatgac caaaggactg cttacgctgg cgaaaggtaa accaatcggt  1380
aaggaaggtt actactggct gaaaatccac ggtgcaaact gtgcgggtgt cgataaggtt  1440
ccgttccctg agcgcatcaa gttcattgag gaaaaccacg agaacatcat ggcttgcgct  1500
aagtctccac tggagaacac ttggtgggct gagcaatggt ctccgttctg cttccttgcg  1560
ttctgctttg agtacgctgg ggtacagcac acggcctga gctataactg ctcccttccg    1620
ctggcgtttg acgggtcttg ctctggcatc cagcacttct ccgcgatgct ccgagatgag  1680
gtaggtggtc gcgcggttaa cttgcttcct agtgaaaccg ttcaggacat ctacgggatt  1740
gttgctaaga aagtcaacga gattctacaa gcagacgcaa tcaatgggac cgataacgaa  1800
gtagttaccg tgaccgatga aaacactggt gaaatctctg agaaagtcaa gctgggcact  1860
aaggcactgg ctggtcaatg gctggcttac ggtgttactc gcagtgtgac taagcgttca  1920
gtcatgacgc tggcttacgg gtccaaagag ttcggcttcc gtcaacaagt gctggaagat  1980
accattcagt gggctattga ttccggcaag ggtctgatgt tcactcagcc gaatcaggct  2040
gctggataca tggctaagct gatttgggaa tctgtgagcg tgacggtggt agctgcggtt  2100
gaagcaatga actggcttaa gtctgctgct aagctgctgg ctgctgaggt caaagataag  2160
aagactggag agattcttcg caagcgttgc gctgtgcatt gggtaactcc tgatggtttc  2220
cctgtgtggc aggaatacaa gaagcctatt cagacgcgct tgaacctgat gttcctcggt  2280
cagttccgct acagcctac cattaacacc aacaaagata gcgagattga tgcacacaaa  2340
caggagtctg gtatcgctcc taactttgta cacagccaag acgtagcca ccttcgtaag   2400
actgtagtgt gggcacacga agtacggga tcgaatctt ttgcactgat tcacgactcc    2460
ttcggtacca ttccggctga cgctgcgaac ctgttcaaag cagtgcgcga aactatggtt  2520
gacacatatg agtcttgtga tgtactggct gatttctacg accagttcgc tgaccagttg  2580
cacgagtctc aattggacaa aatgccagca cttccggcta aggtaactt gaaccctcgt   2640
gacatcttag agtcggactt cgcgttcgcg taa                               2673
```

<210> SEQ ID NO 23
<211> LENGTH: 890
<212> TYPE: PRT
<213> ORGANISM: Artificial Sequence
<220> FEATURE:
<223> OTHER INFORMATION: T7RNAP variant

<400> SEQUENCE: 23

Met His His His His His His Met Asn Thr Ile Asn Ile Ala Lys Asn
1               5                   10                  15

Asp Phe Ser Asp Ile Glu Leu Ala Ala Ile Pro Phe Asn Thr Leu Ala
            20                  25                  30

Asp His Tyr Gly Glu Arg Leu Ala Arg Glu Gln Leu Ala Leu Glu His
        35                  40                  45

```
Glu Ser Tyr Glu Met Gly Glu Ala Arg Phe Arg Lys Met Phe Glu Arg
     50                  55                  60

Gln Leu Lys Ala Gly Glu Val Ala Asp Asn Ala Ala Lys Pro Leu
 65              70                  75                  80

Ile Thr Thr Leu Leu Pro Lys Met Ile Ala Arg Ile Asn Asp Trp Phe
                 85                  90                  95

Glu Glu Val Lys Ala Lys Arg Gly Lys Arg Pro Thr Ala Phe Gln Phe
            100                 105                 110

Leu Gln Glu Ile Lys Pro Glu Ala Val Ala Tyr Ile Thr Ile Lys Thr
            115                 120                 125

Thr Leu Ala Cys Leu Thr Ser Ala Trp Asn Thr Thr Val Gln Ala Val
            130                 135                 140

Ala Ser Ala Ile Gly Arg Ala Ile Glu Asp Glu Ala Arg Phe Gly Arg
145                 150                 155                 160

Ile Arg Asp Leu Glu Ala Lys His Phe Lys Lys Asn Val Glu Glu Gln
                165                 170                 175

Leu Asn Lys Arg Val Gly His Val Tyr Lys Lys Ala Phe Met Gln Val
                180                 185                 190

Val Glu Ala Asp Met Leu Ser Lys Gly Leu Leu Gly Gly Glu Ala Trp
            195                 200                 205

Ser Ser Trp His Lys Glu Asp Ser Ile His Val Gly Val Arg Cys Ile
210                 215                 220

Glu Met Leu Ile Glu Ser Thr Gly Met Val Ser Leu His Arg Gln Asn
225                 230                 235                 240

Ala Gly Val Val Gly Gln Asp Ser Glu Thr Ile Glu Leu Ala Pro Glu
                245                 250                 255

Tyr Ala Glu Ala Ile Ala Thr Arg Ala Gly Ala Leu Ala Gly Ile Ser
                260                 265                 270

Pro Met Phe Gln Pro Cys Val Val Pro Pro Lys Pro Trp Thr Gly Ile
            275                 280                 285

Thr Gly Gly Gly Tyr Trp Ala Asn Gly Arg Arg Pro Leu Ala Leu Val
            290                 295                 300

Arg Thr His Ser Lys Lys Ala Leu Met Arg Tyr Glu Asp Val Tyr Met
305                 310                 315                 320

Pro Glu Val Tyr Lys Ala Ile Asn Ile Ala Gln Asn Thr Ala Trp Lys
                325                 330                 335

Ile Asn Lys Lys Val Leu Ala Val Ala Asn Val Ile Thr Lys Trp Lys
                340                 345                 350

His Cys Pro Val Glu Asp Ile Pro Ala Ile Glu Arg Glu Leu Pro
            355                 360                 365

Met Lys Pro Glu Asp Ile Asp Met Asn Pro Glu Ala Leu Thr Ala Trp
     370                 375                 380

Lys Arg Ala Ala Ala Val Tyr Arg Lys Asp Lys Ala Arg Lys Ser
385                 390                 395                 400

Arg Arg Ile Ser Leu Glu Phe Met Leu Glu Gln Ala Asn Lys Phe Ala
                405                 410                 415

Asn His Lys Ala Ile Trp Phe Pro Tyr Asn Met Asp Trp Arg Gly Arg
            420                 425                 430

Val Tyr Ala Val Ser Met Phe Asn Pro Gln Gly Asn Asp Met Thr Lys
            435                 440                 445

Gly Leu Leu Thr Leu Ala Lys Gly Lys Pro Ile Gly Lys Glu Gly Tyr
450                 455                 460
```

```
Tyr Trp Leu Lys Ile His Gly Ala Asn Cys Ala Gly Val Asp Lys Val
465                 470                 475                 480

Pro Phe Pro Glu Arg Ile Lys Phe Ile Glu Glu Asn His Glu Asn Ile
                485                 490                 495

Met Ala Cys Ala Lys Ser Pro Leu Glu Asn Thr Trp Trp Ala Glu Gln
            500                 505                 510

Trp Ser Pro Phe Cys Phe Leu Ala Phe Cys Phe Glu Tyr Ala Gly Val
        515                 520                 525

Gln His His Gly Leu Ser Tyr Asn Cys Ser Leu Pro Leu Ala Phe Asp
    530                 535                 540

Gly Ser Cys Ser Gly Ile Gln His Phe Ser Ala Met Leu Arg Asp Glu
545                 550                 555                 560

Val Gly Gly Arg Ala Val Asn Leu Leu Pro Ser Glu Thr Val Gln Asp
                565                 570                 575

Ile Tyr Gly Ile Val Ala Lys Lys Val Asn Glu Ile Leu Gln Ala Asp
            580                 585                 590

Ala Ile Asn Gly Thr Asp Asn Glu Val Val Thr Val Thr Asp Glu Asn
        595                 600                 605

Thr Gly Glu Ile Ser Glu Lys Val Lys Leu Gly Thr Lys Ala Leu Ala
    610                 615                 620

Gly Gln Trp Leu Ala Tyr Gly Val Thr Arg Ser Val Thr Lys Arg Ser
625                 630                 635                 640

Val Met Thr Leu Ala Tyr Gly Ser Lys Glu Phe Gly Phe Arg Gln Gln
                645                 650                 655

Val Leu Glu Asp Thr Ile Gln Trp Ala Ile Asp Ser Gly Lys Gly Leu
            660                 665                 670

Met Phe Thr Gln Pro Asn Gln Ala Ala Gly Tyr Met Ala Lys Leu Ile
        675                 680                 685

Trp Glu Ser Val Ser Val Thr Val Ala Ala Val Glu Ala Met Asn
    690                 695                 700

Trp Leu Lys Ser Ala Ala Lys Leu Leu Ala Ala Glu Val Lys Asp Lys
705                 710                 715                 720

Lys Thr Gly Glu Ile Leu Arg Lys Arg Cys Ala Val His Trp Val Thr
                725                 730                 735

Pro Asp Gly Phe Pro Val Trp Gln Glu Tyr Lys Lys Pro Ile Gln Thr
            740                 745                 750

Arg Leu Asn Leu Met Phe Leu Gly Gln Phe Arg Leu Gln Pro Thr Ile
        755                 760                 765

Asn Thr Asn Lys Asp Ser Glu Ile Asp Ala His Lys Gln Glu Ser Gly
    770                 775                 780

Ile Ala Pro Asn Phe Val His Ser Gln Asp Gly Ser His Leu Arg Lys
785                 790                 795                 800

Thr Val Val Trp Ala His Glu Lys Tyr Gly Ile Glu Ser Phe Ala Leu
                805                 810                 815

Ile His Asp Ser Phe Gly Thr Ile Pro Ala Asp Ala Ala Asn Leu Phe
            820                 825                 830

Lys Ala Val Arg Glu Thr Met Val Asp Thr Tyr Glu Ser Cys Asp Val
        835                 840                 845

Leu Ala Asp Phe Tyr Asp Gln Phe Ala Asp Gln Leu His Glu Ser Gln
    850                 855                 860

Leu Asp Lys Met Pro Ala Leu Pro Ala Lys Gly Asn Leu Asn Leu Arg
865                 870                 875                 880

Asp Ile Leu Glu Ser Asp Phe Ala Phe Ala
```

<210> SEQ ID NO 24
<211> LENGTH: 2673
<212> TYPE: DNA
<213> ORGANISM: Artificial Sequence
<220> FEATURE:
<223> OTHER INFORMATION: T7RNAP variant

<400> SEQUENCE: 24

| | | | | | | |
|---|---|---|---|---|---|---|
| atgcaccatc | accatcacca | tatgaacacg | attaacatcg | ctaagaacga | cttctctgac | 60 |
| atcgaactgg | ctgctatccc | gttcaacact | ctggctgacc | attacggtga | gcgtttagct | 120 |
| cgcgaacagt | tggcccttga | gcatgagtct | tacgagatgg | gtgaagcacg | cttccgcaag | 180 |
| atgtttgagc | gtcaacttaa | agctggtgag | gttgcggata | cgctgccgc | caagcctctc | 240 |
| atcactaccc | tactccctaa | gatgattgca | cgcatcaacg | actggtttga | ggaagtgaaa | 300 |
| gctaagcgcg | gcaagcgccc | gacagccttc | cagttcctgc | aagaaatcaa | gccggaagcc | 360 |
| gtagcgtaca | tcaccattaa | gaccactctg | gcttgcctaa | ccagtgcttg | gaatacaacc | 420 |
| gttcaggctg | tagcaagcgc | aatcggtcgg | gccattgagg | acgaggctcg | cttcggtcgt | 480 |
| atccgtgacc | ttgaagctaa | gcacttcaag | aaaaacgttg | aggaacaact | caacaagcgc | 540 |
| gtagggcacg | tctacaagaa | agcatttatg | caagttgtcg | aggctgacat | gctctctaag | 600 |
| ggtctactcg | gtggcgaggc | gtggtcttcg | tggcataagg | aagactctat | tcatgtagga | 660 |
| gtacgctgca | tcgagatgct | cattgagtca | accggaatgg | ttagcttaca | ccgccaaaat | 720 |
| gctggcgtag | taggtcaaga | ctctgagact | atcgaactcg | cacctgaata | cgctgaggct | 780 |
| atcgcaaccc | gtgcaggtgc | gctggctggc | atctctccga | tgttccaacc | ttgcgtagtt | 840 |
| cctcctaagc | cgtggactgg | cattactggt | ggtggctatt | gggctaacgg | tcgtcgtcct | 900 |
| ctggcgctgg | tgcgtactca | cagtaagaaa | gcactgatgc | gctacgaaga | cgtttacatg | 960 |
| cctgaggtgt | acaaagcgat | taacattgcg | caaaacaccg | catggaaaat | caacaagaaa | 1020 |
| gtcctagcgg | tcgccaacgt | aatcaccaag | tggaagcatt | gtccggtcga | ggacatccct | 1080 |
| gcgattgagc | gtgaagaact | cccgatgaaa | ccggaagaca | tcgacatgaa | tcctgaggct | 1140 |
| ctcaccgcgt | ggaaacgtgc | tgccgctgct | gtgtaccgca | aggacaaggc | tcgcaagtct | 1200 |
| agtcgtatca | gccttgagtt | catgcttgag | caagccaata | gtttgctaa | ccataaggcc | 1260 |
| atctggttcc | cttacaacat | ggactggcgc | ggtcgtgttt | acgctgtgtc | aatgttcaac | 1320 |
| ccgcaaggta | acgatatgac | caaaggactg | cttacgctgg | cgaaaggtaa | accaatcggt | 1380 |
| aaggaaggtt | actactggct | gaaaatccac | ggtgcaaact | gtgcgggtgt | cgataaggtt | 1440 |
| ccgttccctg | agcgcatcaa | gttcattgag | gaaaaccacg | agaacatcat | ggcttgcgct | 1500 |
| aagtctccac | tggagaacac | ttggtgggct | gagcaatggt | ctccgttctg | cttccttgcg | 1560 |
| ttctgctttg | agtacgctgg | ggtacagcac | cacggcctga | gctataactg | ctcccttccg | 1620 |
| ctggcgtttg | acgggtcttg | ctctggcatc | cagcacttct | ccgcgatgct | ccgagatgag | 1680 |
| gtaggtggtc | gcgcggttaa | cttgcttcct | agtgaaaccg | ttcaggacat | ctacgggatt | 1740 |
| gttgctaaga | agtcaacga | gattctacaa | gcagacgcaa | tcaatgggac | cgataacgaa | 1800 |
| gtagttaccg | tgaccgatga | gaacactggt | gaaatctctg | agaaagtcaa | gctgggcact | 1860 |
| aaggcactgg | ctggtcaatg | gctggcttac | ggtgttactc | gcagtgtgac | taagcgttca | 1920 |
| gtcatgacgc | tggcttacgg | gtccaaagag | ttcggcttcc | gtcaacaagt | gctggaagat | 1980 |
| accattcagt | gggctattga | ttccggcaag | ggtctgatgt | tcactcagcc | gaatcaggct | 2040 |

```
gctggataca tggctaagct gatttgggaa tctgtgagcg tgacggtggt agctgcggtt    2100
gaagcaatga actggcttaa gtctgctgct aagctgctgg ctgctgaggt caaagataag    2160
aagactggag agattcttcg caagcgttgc gctgtgcatt gggtaactcc tgatggtttc    2220
cctgtgtggc aggaatacaa gaagcctatt cagacgcgct tgaacctgat gttcctcggt    2280
cagttccgct acagcctac cattaacacc aacaaagata gcgagattga tgcacacaaa    2340
caggagtctg gtatcgctcc taactttgta cacagccaag acggtagcca ccttcgtaag    2400
actgtagtgt gggcacacga agtacggga atcgaatctt ttgcactgat tcacgactcc    2460
ttcggtacca ttccggctga cgctgcgaac ctgttcaaag cagtgcgcga aactatggtt    2520
gacacatatg agtcttgtga tgtactggct gatttctacg accagttcgc tgaccagttg    2580
cacgagtctc aattggacaa aatgccagca cttccggcta aaggtaactt gaacctccgt    2640
gacatcttag agtcggactt cgcgttcgcg taa                                 2673
```

<210> SEQ ID NO 25
<211> LENGTH: 890
<212> TYPE: PRT
<213> ORGANISM: Artificial Sequence
<220> FEATURE:
<223> OTHER INFORMATION: T7RNAP variant

<400> SEQUENCE: 25

```
Met His His His His His His Met Asn Thr Ile Asn Ile Ala Lys Asn
1               5                   10                  15

Asp Phe Ser Asp Ile Glu Leu Ala Ala Ile Pro Phe Asn Thr Leu Ala
            20                  25                  30

Asp His Tyr Gly Glu Arg Leu Ala Arg Glu Gln Leu Ala Leu Glu His
        35                  40                  45

Glu Ser Tyr Glu Met Gly Glu Ala Arg Phe Arg Lys Met Phe Glu Arg
    50                  55                  60

Gln Leu Lys Ala Gly Glu Val Ala Asp Asn Ala Ala Lys Pro Leu
65                  70                  75                  80

Ile Thr Thr Leu Leu Pro Lys Met Ile Ala Arg Ile Asn Asp Trp Phe
                85                  90                  95

Glu Glu Val Lys Ala Lys Arg Gly Lys Arg Pro Thr Ala Phe Gln Phe
            100                 105                 110

Leu Gln Glu Ile Lys Pro Glu Ala Val Ala Tyr Ile Thr Ile Lys Thr
        115                 120                 125

Thr Leu Ala Cys Leu Thr Ser Ala Trp Asn Thr Thr Val Gln Ala Val
    130                 135                 140

Ala Ser Ala Ile Gly Arg Ala Ile Glu Asp Glu Ala Arg Phe Gly Arg
145                 150                 155                 160

Ile Arg Asp Leu Glu Ala Lys His Phe Lys Lys Asn Val Glu Glu Gln
                165                 170                 175

Leu Asn Lys Arg Val Gly His Val Tyr Lys Lys Ala Phe Met Gln Val
            180                 185                 190

Val Glu Ala Asp Met Leu Ser Lys Gly Leu Leu Gly Gly Glu Ala Trp
        195                 200                 205

Ser Ser Trp His Lys Glu Asp Ser Ile His Val Gly Val Arg Cys Ile
    210                 215                 220

Glu Met Leu Ile Glu Ser Thr Gly Met Val Ser Leu His Arg Gln Asn
225                 230                 235                 240

Ala Gly Val Val Gly Gln Asp Ser Glu Thr Ile Glu Leu Ala Pro Glu
```

-continued

```
                        245                 250                 255
Tyr Ala Glu Ala Ile Ala Thr Arg Ala Gly Ala Leu Ala Gly Ile Ser
                260                 265                 270

Pro Met Phe Gln Pro Cys Val Val Pro Lys Pro Trp Thr Gly Ile
            275                 280                 285

Thr Gly Gly Tyr Trp Ala Asn Gly Arg Arg Pro Leu Ala Leu Val
        290                 295                 300

Arg Thr His Ser Lys Lys Ala Leu Met Arg Tyr Glu Asp Val Tyr Met
305                 310                 315                 320

Pro Glu Val Tyr Lys Ala Ile Asn Ile Ala Gln Asn Thr Ala Trp Lys
                325                 330                 335

Ile Asn Lys Lys Val Leu Ala Val Ala Asn Val Ile Thr Lys Trp Lys
                340                 345                 350

His Cys Pro Val Glu Asp Ile Pro Ala Ile Glu Arg Glu Glu Leu Pro
            355                 360                 365

Met Lys Pro Glu Asp Ile Asp Met Asn Pro Glu Ala Leu Thr Ala Trp
        370                 375                 380

Lys Arg Ala Ala Ala Val Tyr Arg Lys Asp Lys Ala Arg Lys Ser
385                 390                 395                 400

Ser Arg Ile Ser Leu Glu Phe Met Leu Glu Gln Ala Asn Lys Phe Ala
                405                 410                 415

Asn His Lys Ala Ile Trp Phe Pro Tyr Asn Met Asp Trp Arg Gly Arg
                420                 425                 430

Val Tyr Ala Val Ser Met Phe Asn Pro Gln Gly Asn Asp Met Thr Lys
            435                 440                 445

Gly Leu Leu Thr Leu Ala Lys Gly Lys Pro Ile Gly Lys Glu Gly Tyr
450                 455                 460

Tyr Trp Leu Lys Ile His Gly Ala Asn Cys Ala Gly Val Asp Lys Val
465                 470                 475                 480

Pro Phe Pro Glu Arg Ile Lys Phe Ile Glu Glu Asn His Glu Asn Ile
                485                 490                 495

Met Ala Cys Ala Lys Ser Pro Leu Glu Asn Thr Trp Trp Ala Glu Gln
            500                 505                 510

Trp Ser Pro Phe Cys Phe Leu Ala Phe Cys Phe Glu Tyr Ala Gly Val
        515                 520                 525

Gln His His Gly Leu Ser Tyr Asn Cys Ser Leu Pro Leu Ala Phe Asp
            530                 535                 540

Gly Ser Cys Ser Gly Ile Gln His Phe Ser Ala Met Leu Arg Asp Glu
545                 550                 555                 560

Val Gly Gly Arg Ala Val Asn Leu Leu Pro Ser Glu Thr Val Gln Asp
                565                 570                 575

Ile Tyr Gly Ile Val Ala Lys Lys Val Asn Glu Ile Leu Gln Ala Asp
                580                 585                 590

Ala Ile Asn Gly Thr Asp Asn Glu Val Val Thr Val Thr Asp Glu Asn
            595                 600                 605

Thr Gly Glu Ile Ser Glu Lys Val Lys Leu Gly Thr Lys Ala Leu Ala
        610                 615                 620

Gly Gln Trp Leu Ala Tyr Gly Val Thr Arg Ser Val Thr Lys Arg Ser
625                 630                 635                 640

Val Met Thr Leu Ala Tyr Gly Ser Lys Glu Phe Gly Phe Arg Gln Gln
                645                 650                 655

Val Leu Glu Asp Thr Ile Gln Trp Ala Ile Asp Ser Gly Lys Gly Leu
                660                 665                 670
```

```
Met Phe Thr Gln Pro Asn Gln Ala Ala Gly Tyr Met Ala Lys Leu Ile
            675                 680                 685

Trp Glu Ser Val Ser Val Thr Val Ala Ala Val Glu Ala Met Asn
690                 695                 700

Trp Leu Lys Ser Ala Ala Lys Leu Leu Ala Ala Glu Val Lys Asp Lys
705                 710                 715                 720

Lys Thr Gly Glu Ile Leu Arg Lys Arg Cys Ala Val His Trp Val Thr
                725                 730                 735

Pro Asp Gly Phe Pro Val Trp Gln Glu Tyr Lys Lys Pro Ile Gln Thr
            740                 745                 750

Arg Leu Asn Leu Met Phe Leu Gly Gln Phe Arg Leu Gln Pro Thr Ile
                755                 760                 765

Asn Thr Asn Lys Asp Ser Glu Ile Asp Ala His Lys Gln Glu Ser Gly
770                 775                 780

Ile Ala Pro Asn Phe Val His Ser Gln Asp Gly Ser His Leu Arg Lys
785                 790                 795                 800

Thr Val Val Trp Ala His Glu Lys Tyr Gly Ile Glu Ser Phe Ala Leu
                805                 810                 815

Ile His Asp Ser Phe Gly Thr Ile Pro Ala Asp Ala Ala Asn Leu Phe
            820                 825                 830

Lys Ala Val Arg Glu Thr Met Val Asp Thr Tyr Glu Ser Cys Asp Val
            835                 840                 845

Leu Ala Asp Phe Tyr Asp Gln Phe Ala Asp Gln Leu His Glu Ser Gln
850                 855                 860

Leu Asp Lys Met Pro Ala Leu Pro Ala Lys Gly Asn Leu Asn Leu Arg
865                 870                 875                 880

Asp Ile Leu Glu Ser Asp Phe Ala Phe Ala
                885                 890

<210> SEQ ID NO 26
<211> LENGTH: 2673
<212> TYPE: DNA
<213> ORGANISM: Artificial Sequence
<220> FEATURE:
<223> OTHER INFORMATION: T7RNAP variant

<400> SEQUENCE: 26
atgcaccatc accatcacca tatgaacacg attaacatcg ctaagaacga cttctctgac      60
atcgaactgg ctgctatccc gttcaacact ctggctgacc attacggtga gcgtttagct     120
cgcgaacagt tggcccttga gcatgagtct tacgagatgg gtgaagcacg cttccgcaag     180
atgtttgagc gtcaacttaa agctggtgag gttgcggata cgctgccgc caagcctctc     240 atcactaccc tactccctaa gatgattgca cgcatcaacg actggtttga ggaagtgaaa     300
gctaagcgcg gcaagcgccc gacagccttc cagttcctgc aagaaatcaa gccggaagcc     360
gtagcgtaca tcaccattaa gaccactctg gcttgcctaa ccagtgcttg gaatacaacc     420
gttcaggctg tagcaagcgc aatcggtcgg gccattgagg acgaggctcg cttcggtcgt     480
atccgtgacc ttgaagctaa gcacttcaag aaaaacgttg aggaacaact caacaagcgc     540
gtagggcacg tctacaagaa agcatttatg caagttgtcg aggctgacat gctctctaag     600
ggtctactcg gtggcgaggc gtggtcttcg tggcataagg aagactctat tcatgtagga     660
gtacgctgca tcgagatgct cattgagtca accggaatgg ttagcttaca ccgccaaaat     720
gctggcgtag taggtcaaga ctctgagact atcgaactcg cacctgaata cgctgaggct     780
```

| | |
|---|---|
| atcgcaaccc gtgcaggtgc gctggctggc atctctccga tgttccaacc ttgcgtagtt | 840 |
| cctcctaagc cgtggactgg cattactggt ggtggctatt gggctaacgg tcgtcgtcct | 900 |
| ctggcgctgg tgcgtactca cagtaagaaa gcactgatgc gctacgaaga cgtttacatg | 960 |
| cctgaggtgt acaaagcgat taacattgcg caaaacaccg catggaaaat caacaagaaa | 1020 |
| gtcctagcgg tcgccaacgt aatcaccaag tggaagcatt gtccggtcga ggacatccct | 1080 |
| gcgattgagc gtgaagaact cccgatgaaa ccggaagaca tcgacatgaa tcctgaggct | 1140 |
| ctcaccgcgt ggaaacgtgc tgccgctgct gtgtaccgca aggacaaggc tcgcaagtct | 1200 |
| atacgtatca gccttgagtt catgcttgag caagccaata agtttgctaa ccataaggcc | 1260 |
| atctggttcc cttacaacat ggactggcgc ggtcgtgttt acgctgtgtc aatgttcaac | 1320 |
| ccgcaaggta acgatatgac caaaggactg cttacgctgg cgaaaggtaa accaatcggt | 1380 |
| aaggaaggtt actactggct gaaaatccac ggtgcaaact gtgcgggtgt cgataaggtt | 1440 |
| ccgttccctg agcgcatcaa gttcattgag gaaaaccacg agaacatcat ggcttgcgct | 1500 |
| aagtctccac tggagaacac ttggtgggct gagcaagatt ctccgttctg cttccttgcg | 1560 |
| ttctgctttg agtacgctgg ggtacagcac cacggcctga gctataactg ctcccttccg | 1620 |
| ctggcgtttg acgggtcttg ctctggcatc cagcacttct ccgcgatgct ccgagatgag | 1680 |
| gtaggtggtc gcgcggttaa cttgcttcct agtgaaaccg ttcaggacat ctacgggatt | 1740 |
| gttgctaaga aagtcaacga gattctacaa gcagacgcaa tcaatgggac cgataacgaa | 1800 |
| gtagttaccg tgaccgatga aacactggt gaaatctctg agaaagtcaa gctgggcact | 1860 |
| aaggcactgg ctggtcaatg gctggcttac ggtgttactc gcagtgtgac taagcgttca | 1920 |
| gtcatgacgc tggcttacgg gtccaaagag ttcggcttcc gtcaacaagt gctggaagat | 1980 |
| accattcagt gggctattga ttccggcaag ggtctgatgt tcactcagcc gaatcaggct | 2040 |
| gctggataca tggctaagct gatttgggaa tctgtgagcg tgacggtggt agctgcggtt | 2100 |
| gaagcaatga cttggcttaa gtctgctgct aagctgctgg ctgctgaggt caaagataag | 2160 |
| aagactggag agattcttcg caagcgttgc gctgtgcatt gggtaactcc tgatggtttc | 2220 |
| cctgtgtggc aggaatacaa gaagcctatt cagacgcgct tgaacctgat gttcctcggt | 2280 |
| cagttccgct tacagcctac cattaacacc aacaaagata gcgagattga tgcacacaaa | 2340 |
| caggagtctg gtatcgctcc taactttgta cacagccaag acggtagcca ccttcgtaag | 2400 |
| actgtagtgt gggcacacga gaagtacgga atcgaatctt ttgcactgat tcacgactcc | 2460 |
| ttcggtacca ttccggctga cgctgcgaac ctgttcaaag cagtgcgcga aactatggtt | 2520 |
| gacacatatg agtcttgtga tgtactggct gatttctacg accagttcgc tgaccagttg | 2580 |
| cacgagtctc aattggacaa aatgccagca cttccggcta aggtaacttg aacctccgt | 2640 |
| gacatcttag agtcggactt cgcgttcgcg taa | 2673 |

<210> SEQ ID NO 27
<211> LENGTH: 890
<212> TYPE: PRT
<213> ORGANISM: Artificial Sequence
<220> FEATURE:
<223> OTHER INFORMATION: T7RNAP variant

<400> SEQUENCE: 27

Met His His His His His His Met Asn Thr Ile Asn Ile Ala Lys Asn
1               5                   10                  15

Asp Phe Ser Asp Ile Glu Leu Ala Ala Ile Pro Phe Asn Thr Leu Ala
            20                  25                  30

```
Asp His Tyr Gly Glu Arg Leu Ala Arg Glu Gln Leu Ala Leu Glu His
        35                  40                  45
Glu Ser Tyr Glu Met Gly Glu Ala Arg Phe Arg Lys Met Phe Glu Arg
    50                  55                  60
Gln Leu Lys Ala Gly Glu Val Ala Asp Asn Ala Ala Lys Pro Leu
65                  70                  75                  80
Ile Thr Thr Leu Leu Pro Lys Met Ile Ala Arg Ile Asn Asp Trp Phe
                85                  90                  95
Glu Glu Val Lys Ala Lys Arg Gly Lys Arg Pro Thr Ala Phe Gln Phe
                100                 105                 110
Leu Gln Glu Ile Lys Pro Glu Ala Val Ala Tyr Ile Thr Ile Lys Thr
                115                 120                 125
Thr Leu Ala Cys Leu Thr Ser Ala Trp Asn Thr Thr Val Gln Ala Val
130                 135                 140
Ala Ser Ala Ile Gly Arg Ala Ile Glu Asp Glu Ala Arg Phe Gly Arg
145                 150                 155                 160
Ile Arg Asp Leu Glu Ala Lys His Phe Lys Lys Asn Val Glu Glu Gln
                165                 170                 175
Leu Asn Lys Arg Val Gly His Val Tyr Lys Lys Ala Phe Met Gln Val
                180                 185                 190
Val Glu Ala Asp Met Leu Ser Lys Gly Leu Leu Gly Gly Glu Ala Trp
                195                 200                 205
Ser Ser Trp His Lys Glu Asp Ser Ile His Val Gly Val Arg Cys Ile
        210                 215                 220
Glu Met Leu Ile Glu Ser Thr Gly Met Val Ser Leu His Arg Gln Asn
225                 230                 235                 240
Ala Gly Val Val Gly Gln Asp Ser Glu Thr Ile Glu Leu Ala Pro Glu
                245                 250                 255
Tyr Ala Glu Ala Ile Ala Thr Arg Ala Gly Ala Leu Ala Gly Ile Ser
                260                 265                 270
Pro Met Phe Gln Pro Cys Val Val Pro Pro Lys Pro Trp Thr Gly Ile
            275                 280                 285
Thr Gly Gly Gly Tyr Trp Ala Asn Gly Arg Arg Pro Leu Ala Leu Val
        290                 295                 300
Arg Thr His Ser Lys Lys Ala Leu Met Arg Tyr Glu Asp Val Tyr Met
305                 310                 315                 320
Pro Glu Val Tyr Lys Ala Ile Asn Ile Ala Gln Asn Thr Ala Trp Lys
                325                 330                 335
Ile Asn Lys Lys Val Leu Ala Val Ala Asn Val Ile Thr Lys Trp Lys
                340                 345                 350
His Cys Pro Val Glu Asp Ile Pro Ala Ile Glu Arg Glu Glu Leu Pro
            355                 360                 365
Met Lys Pro Glu Asp Ile Asp Met Asn Pro Glu Ala Leu Thr Ala Trp
        370                 375                 380
Lys Arg Ala Ala Ala Val Tyr Arg Lys Asp Lys Ala Arg Lys Ser
385                 390                 395                 400
Ile Arg Ile Ser Leu Glu Phe Met Leu Glu Gln Ala Asn Lys Phe Ala
                405                 410                 415
Asn His Lys Ala Ile Trp Phe Pro Tyr Asn Met Asp Trp Arg Gly Arg
            420                 425                 430
Val Tyr Ala Val Ser Met Phe Asn Pro Gln Gly Asn Asp Met Thr Lys
        435                 440                 445
```

```
Gly Leu Leu Thr Leu Ala Lys Gly Lys Pro Ile Gly Lys Glu Gly Tyr
    450                 455                 460
Tyr Trp Leu Lys Ile His Gly Asn Cys Ala Gly Val Asp Lys Val
465                 470                 475                 480
Pro Phe Pro Glu Arg Ile Lys Phe Ile Glu Glu Asn His Glu Asn Ile
                485                 490                 495
Met Ala Cys Ala Lys Ser Pro Leu Glu Asn Thr Trp Trp Ala Glu Gln
                500                 505                 510
Asp Ser Pro Phe Cys Phe Leu Ala Phe Cys Phe Glu Tyr Ala Gly Val
            515                 520                 525
Gln His His Gly Leu Ser Tyr Asn Cys Ser Leu Pro Leu Ala Phe Asp
    530                 535                 540
Gly Ser Cys Ser Gly Ile Gln His Phe Ser Ala Met Leu Arg Asp Glu
545                 550                 555                 560
Val Gly Gly Arg Ala Val Asn Leu Leu Pro Ser Glu Thr Val Gln Asp
                565                 570                 575
Ile Tyr Gly Ile Val Ala Lys Lys Val Asn Glu Ile Leu Gln Ala Asp
                580                 585                 590
Ala Ile Asn Gly Thr Asp Asn Glu Val Val Thr Val Thr Asp Glu Asn
            595                 600                 605
Thr Gly Glu Ile Ser Glu Lys Val Lys Leu Gly Thr Lys Ala Leu Ala
    610                 615                 620
Gly Gln Trp Leu Ala Tyr Gly Val Thr Arg Ser Val Thr Lys Arg Ser
625                 630                 635                 640
Val Met Thr Leu Ala Tyr Gly Ser Lys Glu Phe Gly Phe Arg Gln Gln
                645                 650                 655
Val Leu Glu Asp Thr Ile Gln Trp Ala Ile Asp Ser Gly Lys Gly Leu
            660                 665                 670
Met Phe Thr Gln Pro Asn Gln Ala Ala Gly Tyr Met Ala Lys Leu Ile
    675                 680                 685
Trp Glu Ser Val Ser Val Thr Val Val Ala Ala Val Glu Ala Met Asn
690                 695                 700
Trp Leu Lys Ser Ala Ala Lys Leu Leu Ala Ala Glu Val Lys Asp Lys
705                 710                 715                 720
Lys Thr Gly Glu Ile Leu Arg Lys Arg Cys Ala Val His Trp Val Thr
                725                 730                 735
Pro Asp Gly Phe Pro Val Trp Gln Glu Tyr Lys Lys Pro Ile Gln Thr
            740                 745                 750
Arg Leu Asn Leu Met Phe Leu Gly Gln Phe Arg Leu Gln Pro Thr Ile
    755                 760                 765
Asn Thr Asn Lys Asp Ser Glu Ile Asp Ala His Lys Gln Glu Ser Gly
770                 775                 780
Ile Ala Pro Asn Phe Val His Ser Gln Asp Gly Ser His Leu Arg Lys
785                 790                 795                 800
Thr Val Val Trp Ala His Glu Lys Tyr Gly Ile Glu Ser Phe Ala Leu
                805                 810                 815
Ile His Asp Ser Phe Gly Thr Ile Pro Ala Asp Ala Ala Asn Leu Phe
            820                 825                 830
Lys Ala Val Arg Glu Thr Met Val Asp Thr Tyr Glu Ser Cys Asp Val
    835                 840                 845
Leu Ala Asp Phe Tyr Asp Gln Phe Ala Asp Gln Leu His Glu Ser Gln
850                 855                 860
Leu Asp Lys Met Pro Ala Leu Pro Ala Lys Gly Asn Leu Asn Leu Arg
```

```
                865                 870                 875                 880
Asp Ile Leu Glu Ser Asp Phe Ala Phe Ala
                    885                 890

<210> SEQ ID NO 28
<211> LENGTH: 2673
<212> TYPE: DNA
<213> ORGANISM: Artificial Sequence
<220> FEATURE:
<223> OTHER INFORMATION: T7RNAP variant

<400> SEQUENCE: 28
atgcaccatc accatcacca tatgaacacg attaacatcg ctaagaacga cttctctgac        60
atcgaactgg ctgctatccc gttcaacact ctggctgacc attacggtga gcgtttagct       120
cgcgaacagt tgcccttga gcatgagtct tacgagatgg gtgaagcacg cttccgcaag        180
atgtttgagc gtcaacttaa agctggtgag gttgcggata cgctgccgc caagcctctc       240 atcactaccc tactccctaa gatgattgca cgcatcaacg actggtttga ggaagtgaaa       300
gctaagcgcg gcaagcgccc gacagccttc cagttcctgc aagaaatcaa gccggaagcc       360
gtagcgtaca tcaccattaa gaccactctg gcttgcctaa ccagtataga caatacaacc       420
gttcaggctg tagcaagcgc aatcggtcgg gccattgagg acgaggctcg cttcggtcgt       480
atccgtgacc ttgaagctaa gcacttcaag aaaaacgttg aggaacaact caacaagcgc       540
gtagggcacg tctacaagaa agcatttatg caagttgtcg aggctgacat gctctctaag       600
ggtctactcg gtggcgaggc gtggtcttcg tggcataagg aagactctat tcatgtagga       660
gtacgctgca tcgagatgct cattgagtca accggaatgg ttagcttaca ccgccaaaat       720
gctggcgtag taggtcaaga ctctgagact atcgaactcg cacctgaata cgctgaggct       780
atcgcaaccc gtgcaggtgc gctggctggc atctctccga tgttccaacc ttgcgtagtt       840
cctcctaagc cgtggactgg cattactggt ggtggctatt gggctaacgg tcgtcgtcct       900
ctggcgctgg tgcgtactca cagtaagaaa gcactgatgc gctacgaaga cgtttacatg       960
cctgaggtgt acaaagcgat taacattgcg caaaacaccg catggaaaat caacaagaaa      1020
gtcctagcgg tcgccaacgt aatcaccaag tggaagcatt gtccggtcga agacatccct      1080
gcgattgagc gtgaagaact cccgatgaaa ccggaagaca tcgacatgaa tcctgaggct      1140
ctcaccgcgt ggaaacgtgc tgccgctgct gtgtaccgca gagacaaggc tcgcaagtct      1200
cgccgtatct atcttgagtt catgcttgag caagccaata gtttgctaa ccataaggcc       1260 atctggttcc cttacaacat ggactggcgc ggtcgtgttt acgctgtgtc aatgttcaac      1320
ccgcaaggta cgattggac caaaggactg cttacgctgg cgaaaggtaa accaatcggt      1380
aaggaaggtt actactggct gaaaatccac ggtgcaaact gtgcgggtgt cgataaggtt      1440
ccgttccctg agcgcatcaa gttcattgag aaaaccacg agaacatcat ggcttgcgct      1500
aagtctccac tggagaacac ttggtgggct gagcaagatt ccccgttctg cttccttgcg      1560
ttctgctttg agtacgctgg ggtacagcac cacggcctga gctataactg ctcccttccg      1620
ctggcgtttg acgggtcttg ctctggcatc cagcacttct ccgcgatgct ccgagatgag      1680
gtaggtggtc gcgcggttaa cttgcttcct agtgaaaccg ttcaggacat ctacgggatt      1740
gttgctaaga agtcaacga gattctacaa gcagacgcaa tcaatgggac cgataacgaa      1800
gtagttaccg tgaccgatga aacactggt gaaatctctg agaaagtcaa gctgggcact      1860
aaggcactgg ctggtcaatg gctggcttac ggtgttactc gcagtgtgac taagcgttca      1920
```

-continued

```
gtcatgacgc tggcttacgg gtccaaagag ttcggcttcc gtcaacaagt gctggaagat    1980
accattcagt gggctattga ttccggcaag ggtctgatgt tcactcagcc gaatcaggct    2040
gctggataca tggctaagct gatttgggaa tctgtgagcg tgacggtggt agctgcggtt    2100
gaagcaatga actggcttaa gtctgctgct aagctgctgg ctgctgaggt caaagataag    2160
aagactggag agattcttcg caagcgttgc gctgtgcatt gggtaactcc tgatggtttc    2220
cctgtgtggc aggaatacaa gaagcctatt cagacgcgct tgaacctgat gttcctcggt    2280
cagttccgct acagcctacc cattaacacc aacaaagata gcgagattga tgcacacaaa    2340
caggagtctg gtatcgctcc taactttgta cacagccaag acggtagcca ccttcgtaag    2400
actgtagtgt gggcacacga gaagtacgga atcgaatctt ttgcactgat tcacgactcc    2460
ttcggtacca ttccggctga cgctgcgaac ctgttcaaag cagtgcgcga aactatggtt    2520
gacacatatg agtcttgtga tgtactggct gatttctacg accagttcgc tgaccagttg    2580
cacgagtctc aattggacaa aatgccagca cttccggcta aggtaactt gaacctccgt    2640 gacatcttag agtcggactt cgcgttcgcg taa                                  2673
```

<210> SEQ ID NO 29
<211> LENGTH: 890
<212> TYPE: PRT
<213> ORGANISM: Artificial Sequence
<220> FEATURE:
<223> OTHER INFORMATION: T7RNAP variant

<400> SEQUENCE: 29

```
Met His His His His His His Met Asn Thr Ile Asn Ile Ala Lys Asn
1               5                   10                  15

Asp Phe Ser Asp Ile Glu Leu Ala Ala Ile Pro Phe Asn Thr Leu Ala
                20                  25                  30

Asp His Tyr Gly Glu Arg Leu Ala Arg Glu Gln Leu Ala Leu Glu His
            35                  40                  45

Glu Ser Tyr Glu Met Gly Glu Ala Arg Phe Arg Lys Met Phe Glu Arg
        50                  55                  60

Gln Leu Lys Ala Gly Glu Val Ala Asp Asn Ala Ala Lys Pro Leu
65                  70                  75                  80

Ile Thr Thr Leu Leu Pro Lys Met Ile Ala Arg Ile Asn Asp Trp Phe
                85                  90                  95

Glu Glu Val Lys Ala Lys Arg Gly Lys Arg Pro Thr Ala Phe Gln Phe
            100                 105                 110

Leu Gln Glu Ile Lys Pro Glu Ala Val Ala Tyr Ile Thr Ile Lys Thr
        115                 120                 125

Thr Leu Ala Cys Leu Thr Ser Ile Asp Asn Thr Thr Val Gln Ala Val
    130                 135                 140

Ala Ser Ala Ile Gly Arg Ala Ile Glu Asp Glu Ala Arg Phe Gly Arg
145                 150                 155                 160

Ile Arg Asp Leu Glu Ala Lys His Phe Lys Lys Asn Val Glu Glu Gln
                165                 170                 175

Leu Asn Lys Arg Val Gly His Val Tyr Lys Lys Ala Phe Met Gln Val
            180                 185                 190

Val Glu Ala Asp Met Leu Ser Lys Gly Leu Leu Gly Gly Glu Ala Trp
        195                 200                 205

Ser Ser Trp His Lys Glu Asp Ser Ile His Val Gly Val Arg Cys Ile
    210                 215                 220

Glu Met Leu Ile Glu Ser Thr Gly Met Val Ser Leu His Arg Gln Asn
```

```
              225                 230                 235                 240
Ala Gly Val Val Gly Gln Asp Ser Glu Thr Ile Glu Leu Ala Pro Glu
                    245                 250                 255
Tyr Ala Glu Ala Ile Ala Thr Arg Ala Gly Ala Leu Ala Gly Ile Ser
                    260                 265                 270
Pro Met Phe Gln Pro Cys Val Pro Pro Lys Pro Trp Thr Gly Ile
            275                 280                 285
Thr Gly Gly Gly Tyr Trp Ala Asn Gly Arg Arg Pro Leu Ala Leu Val
        290                 295                 300
Arg Thr His Ser Lys Lys Ala Leu Met Arg Tyr Glu Asp Val Tyr Met
305                 310                 315                 320
Pro Glu Val Tyr Lys Ala Ile Asn Ile Ala Gln Asn Thr Ala Trp Lys
                325                 330                 335
Ile Asn Lys Lys Val Leu Ala Val Ala Asn Val Ile Thr Lys Trp Lys
                340                 345                 350
His Cys Pro Val Glu Asp Ile Pro Ala Ile Glu Arg Glu Glu Leu Pro
            355                 360                 365
Met Lys Pro Glu Asp Ile Asp Met Asn Pro Glu Ala Leu Thr Ala Trp
        370                 375                 380
Lys Arg Ala Ala Ala Val Tyr Arg Arg Asp Lys Ala Arg Lys Ser
385                 390                 395                 400
Arg Arg Ile Tyr Leu Glu Phe Met Leu Glu Gln Ala Asn Lys Phe Ala
                405                 410                 415
Asn His Lys Ala Ile Trp Phe Pro Tyr Asn Met Asp Trp Arg Gly Arg
                420                 425                 430
Val Tyr Ala Val Ser Met Phe Asn Pro Gln Gly Asn Asp Trp Thr Lys
                435                 440                 445
Gly Leu Leu Thr Leu Ala Lys Gly Lys Pro Ile Gly Lys Glu Gly Tyr
        450                 455                 460
Tyr Trp Leu Lys Ile His Gly Ala Asn Cys Ala Gly Val Asp Lys Val
465                 470                 475                 480
Pro Phe Pro Glu Arg Ile Lys Phe Ile Glu Glu Asn His Glu Asn Ile
                485                 490                 495
Met Ala Cys Ala Lys Ser Pro Leu Glu Asn Thr Trp Trp Ala Glu Gln
                500                 505                 510
Asp Ser Pro Phe Cys Phe Leu Ala Phe Cys Phe Glu Tyr Ala Gly Val
            515                 520                 525
Gln His His Gly Leu Ser Tyr Asn Cys Ser Leu Pro Leu Ala Phe Asp
        530                 535                 540
Gly Ser Cys Ser Gly Ile Gln His Phe Ser Ala Met Leu Arg Asp Glu
545                 550                 555                 560
Val Gly Gly Arg Ala Val Asn Leu Leu Pro Ser Glu Thr Val Gln Asp
                565                 570                 575
Ile Tyr Gly Ile Val Ala Lys Lys Val Asn Glu Ile Leu Gln Ala Asp
                580                 585                 590
Ala Ile Asn Gly Thr Asp Asn Glu Val Val Thr Val Thr Asp Glu Asn
            595                 600                 605
Thr Gly Glu Ile Ser Glu Lys Val Lys Leu Gly Thr Lys Ala Leu Ala
        610                 615                 620
Gly Gln Trp Leu Ala Tyr Gly Val Thr Arg Ser Val Thr Lys Arg Ser
625                 630                 635                 640
Val Met Thr Leu Ala Tyr Gly Ser Lys Glu Phe Gly Phe Arg Gln Gln
                645                 650                 655
```

```
Val Leu Glu Asp Thr Ile Gln Trp Ala Ile Asp Ser Gly Lys Gly Leu
            660                 665                 670
Met Phe Thr Gln Pro Asn Gln Ala Ala Gly Tyr Met Ala Lys Leu Ile
        675                 680                 685
Trp Glu Ser Val Ser Val Thr Val Val Ala Ala Val Glu Ala Met Asn
    690                 695                 700
Trp Leu Lys Ser Ala Ala Lys Leu Leu Ala Ala Glu Val Lys Asp Lys
705                 710                 715                 720
Lys Thr Gly Glu Ile Leu Arg Lys Arg Cys Ala Val His Trp Val Thr
                725                 730                 735
Pro Asp Gly Phe Pro Val Trp Gln Glu Tyr Lys Lys Pro Ile Gln Thr
            740                 745                 750
Arg Leu Asn Leu Met Phe Leu Gly Gln Phe Arg Leu Gln Pro Thr Ile
        755                 760                 765
Asn Thr Asn Lys Asp Ser Glu Ile Asp Ala His Lys Gln Glu Ser Gly
    770                 775                 780
Ile Ala Pro Asn Phe Val His Ser Gln Asp Gly Ser His Leu Arg Lys
785                 790                 795                 800
Thr Val Val Trp Ala His Glu Lys Tyr Gly Ile Glu Ser Phe Ala Leu
                805                 810                 815
Ile His Asp Ser Phe Gly Thr Ile Pro Ala Asp Ala Ala Asn Leu Phe
            820                 825                 830
Lys Ala Val Arg Glu Thr Met Val Asp Thr Tyr Glu Ser Cys Asp Val
        835                 840                 845
Leu Ala Asp Phe Tyr Asp Gln Phe Ala Asp Gln Leu His Glu Ser Gln
    850                 855                 860
Leu Asp Lys Met Pro Ala Leu Pro Ala Lys Gly Asn Leu Asn Leu Arg
865                 870                 875                 880
Asp Ile Leu Glu Ser Asp Phe Ala Phe Ala
                885                 890

<210> SEQ ID NO 30
<211> LENGTH: 2673
<212> TYPE: DNA
<213> ORGANISM: Artificial Sequence
<220> FEATURE:
<223> OTHER INFORMATION: T7RNAP variant

<400> SEQUENCE: 30
atgcaccatc accatcacca tatgaacacg attaacatcg ctaagaacga cttctctgac    60
atcgaactgg ctgctatccc gttcaacact ctggctgacc attacggtga gcgtttagct   120
cgcgaacagt tggcccttga gcatgagtct tacgagatgg gtgaagcacg cttccgcaag   180
atgtttgagc gtcaacttaa agctggtgag gttgcggata cgctgccgc caagcctctc    240 atcactaccc tactccctaa gatgattgca cgcatcaacg actggtttga ggaagtgaaa   300
gctaagcgcg gcaagcgccc gacagccttc cagttcctgc aagaaatcaa gccggaagcc   360
gtagcgtaca tcaccattaa gaccactctg gcttgcctaa ccagtgctga caatacaacc   420
gttcaggctg tagcaagcgc aatcggtcgg gccattgagg acgaggctcg cttcggtcgt   480
atccgtgacc ttgaagctaa gcacttcaag aaaaacgttg aggaacaact caacaagcgc   540
gtagggcacg tctacaagaa agcatttatg caagttgtcg aggctgacat gctctctaag   600
ggtctactcg gtggcgaggc gtggtcttcg tggcataagg aagactctat tcatgtagga   660
gtacgctgca tcgagatgct cattgagtca accggaatgg ttagcttaca ccgccaaaat   720
```

```
gctggcgtag taggtcaaga ctctgagact atcgaactcg cacctgaata cgctgaggct    780
atcgcaaccc gtgcaggtgc gctggctggc atctctccga tgttccaacc ttgcgtagtt    840
cctcctaagc cgtggactgg cattactggt ggtggctatt gggctaacgg tcgtcgtcct    900
ctggcgctgg tgcgtactca cagtaagaaa gcactgatgc gctacgaaga cgtttacatg    960
cctgaggtgt acaaagcgat taacattgcg caaaacaccg catggaaaat caacaagaaa   1020
gtcctagcgg tcgccaacgt aatcaccaag tggaagcatt gtccggtcga ggacatccct   1080
gcgattgagc gtgaagaact cccgatgaaa ccggaagaca tcgacatgaa tcctgaggct   1140
ctcaccgcgt ggaaacgtgc tgccgctgct gtgtaccgca aggacaaggc gcgcaagtct   1200
cgccgtatca gccttgagtt catgcttgag caagccaata gtttgctaa ccataaggcc    1260 atctggttcc cttacaacat ggactggcgc ggtcgtgttt acgctgtgtc aatgttcaac   1320
ccgcaaggta acgatatgac caaaggactg cttacgctgg cgaaaggtaa accaatcggt   1380
aaggaaggtt actactggct gaaaatccac ggtgcaaact gtgcgggtgt cgataaggtt   1440
ccgttccctg agcgcatcaa gttcattgag aaaaccacg agaacatcat ggcttgcgct    1500
aagtctccac tggagaacac ttggtgggct gagcaatggt ctccgttctg cttccttgcg   1560
ttctgctttg agtacgctgg ggtacagcac cacggcctga gctataactg ctcccttccg   1620
ctggcgtttg acgggtcttg ctctggcatc cagcacttct ccgcgatgct ccgagatgag   1680
gtaggtggtc gcgcggttaa cttgcttcct agtgaaaccg ttcaggacat ctacgggatt   1740
gttgctaaga aagtcaacga gattctacaa gcagacgcaa tcaatgggac cgataacgaa   1800
gtagttaccg tgaccgatga gaacactggt gaaatctctg agaaagtcaa gctgggcact   1860
aaggcactgg ctggtcaatg gctggcttac ggtgttactc gctgggtgac taagcgttca   1920
gtcatgacgc tggcttacgg gtccaaagag ttcggcttcc gtcaacaagt gctggaattc   1980
accattcagc tgctattga ttccggcaag ggtctgatgt tcactcagcc gaatcaggct    2040
gctggataca tggctaagct gatttgggaa tctgtgagcg tgacggtggt agctgcggtt   2100
gaagcaatga actggcttaa gtctgctgct aagctgctgg ctgctgaggt caaagataag   2160
aagactggag agattcttcg caagcgttgc gctgtgcatt gggtaactcc tgatggtttc   2220
cctgtgtggc aggaatacaa gaagcctatt cagacgcgct tgaacctgat gttcctcggt   2280
cagttccgct tacagcctac cattaacacc aacaaagata gcgagattga tgcacacaaa   2340
caggagtctg gtatcgctcc taactttgta cacagccaag acggtagcca ccttcgtaag   2400
actgtagtgt gggcacacga gaagtacgga atcgaatctt tgcactgat tcacgactcc    2460 ttcggtacca ttccggctga cgctgcgaac ctgttcaaag cagtgcgcga actatggtt    2520 gacacatatg agtcttgtga tgtactggct gatttctacg accagttcgc tgaccagttg   2580
cacgagtctc aattggacaa aatgccagca cttccggcta aggtaactt gaacctccgt    2640 gacatcttag agtcggactt cgcgttcgcg taa                                2673
```

<210> SEQ ID NO 31
<211> LENGTH: 890
<212> TYPE: PRT
<213> ORGANISM: Artificial Sequence
<220> FEATURE:
<223> OTHER INFORMATION: T7RNAP variant

<400> SEQUENCE: 31

```
Met His His His His His His Met Asn Thr Ile Asn Ile Ala Lys Asn
1               5                   10                  15
```

```
Asp Phe Ser Asp Ile Glu Leu Ala Ala Ile Pro Phe Asn Thr Leu Ala
             20                  25                  30

Asp His Tyr Gly Glu Arg Leu Ala Arg Glu Gln Leu Ala Leu Glu His
             35                  40                  45

Glu Ser Tyr Glu Met Gly Glu Ala Arg Phe Arg Lys Met Phe Glu Arg
 50                  55                  60

Gln Leu Lys Ala Gly Glu Val Ala Asp Asn Ala Ala Lys Pro Leu
 65                  70                  75                  80

Ile Thr Thr Leu Leu Pro Lys Met Ile Ala Arg Ile Asn Asp Trp Phe
             85                  90                  95

Glu Glu Val Lys Ala Lys Arg Gly Lys Arg Pro Thr Ala Phe Gln Phe
            100                 105                 110

Leu Gln Glu Ile Lys Pro Glu Ala Val Ala Tyr Ile Thr Ile Lys Thr
            115                 120                 125

Thr Leu Ala Cys Leu Thr Ser Ala Asp Asn Thr Thr Val Gln Ala Val
130                 135                 140

Ala Ser Ala Ile Gly Arg Ala Ile Glu Asp Glu Ala Arg Phe Gly Arg
145                 150                 155                 160

Ile Arg Asp Leu Glu Ala Lys His Phe Lys Lys Asn Val Glu Glu Gln
            165                 170                 175

Leu Asn Lys Arg Val Gly His Val Tyr Lys Lys Ala Phe Met Gln Val
            180                 185                 190

Val Glu Ala Asp Met Leu Ser Lys Gly Leu Leu Gly Gly Glu Ala Trp
            195                 200                 205

Ser Ser Trp His Lys Glu Asp Ser Ile His Val Gly Val Arg Cys Ile
            210                 215                 220

Glu Met Leu Ile Glu Ser Thr Gly Met Val Ser Leu His Arg Gln Asn
225                 230                 235                 240

Ala Gly Val Val Gly Gln Asp Ser Glu Thr Ile Glu Leu Ala Pro Glu
            245                 250                 255

Tyr Ala Glu Ala Ile Ala Thr Arg Ala Gly Ala Leu Ala Gly Ile Ser
            260                 265                 270

Pro Met Phe Gln Pro Cys Val Val Pro Pro Lys Pro Trp Thr Gly Ile
            275                 280                 285

Thr Gly Gly Gly Tyr Trp Ala Asn Gly Arg Arg Pro Leu Ala Leu Val
            290                 295                 300

Arg Thr His Ser Lys Lys Ala Leu Met Arg Tyr Glu Asp Val Tyr Met
305                 310                 315                 320

Pro Glu Val Tyr Lys Ala Ile Asn Ile Ala Gln Asn Thr Ala Trp Lys
            325                 330                 335

Ile Asn Lys Lys Val Leu Ala Val Ala Asn Val Ile Thr Lys Trp Lys
            340                 345                 350

His Cys Pro Val Glu Asp Ile Pro Ala Ile Glu Arg Glu Glu Leu Pro
            355                 360                 365

Met Lys Pro Glu Asp Ile Asp Met Asn Pro Glu Ala Leu Thr Ala Trp
            370                 375                 380

Lys Arg Ala Ala Ala Val Tyr Arg Lys Asp Lys Ala Arg Lys Ser
385                 390                 395                 400

Arg Arg Ile Ser Leu Glu Phe Met Leu Glu Gln Ala Asn Lys Phe Ala
            405                 410                 415

Asn His Lys Ala Ile Trp Phe Pro Tyr Asn Met Asp Trp Arg Gly Arg
            420                 425                 430
```

```
Val Tyr Ala Val Ser Met Phe Asn Pro Gln Gly Asn Asp Met Thr Lys
            435                 440                 445

Gly Leu Leu Thr Leu Ala Lys Gly Lys Pro Ile Gly Lys Glu Gly Tyr
450                 455                 460

Tyr Trp Leu Lys Ile His Gly Ala Asn Cys Ala Gly Val Asp Lys Val
465                 470                 475                 480

Pro Phe Pro Glu Arg Ile Lys Phe Ile Glu Glu Asn His Glu Asn Ile
                485                 490                 495

Met Ala Cys Ala Lys Ser Pro Leu Glu Asn Thr Trp Trp Ala Glu Gln
                500                 505                 510

Trp Ser Pro Phe Cys Phe Leu Ala Phe Cys Phe Glu Tyr Ala Gly Val
            515                 520                 525

Gln His His Gly Leu Ser Tyr Asn Cys Ser Leu Pro Leu Ala Phe Asp
            530                 535                 540

Gly Ser Cys Ser Gly Ile Gln His Phe Ser Ala Met Leu Arg Asp Glu
545                 550                 555                 560

Val Gly Gly Arg Ala Val Asn Leu Leu Pro Ser Glu Thr Val Gln Asp
                565                 570                 575

Ile Tyr Gly Ile Val Ala Lys Lys Val Asn Glu Ile Leu Gln Ala Asp
                580                 585                 590

Ala Ile Asn Gly Thr Asp Asn Glu Val Val Thr Val Thr Asp Glu Asn
            595                 600                 605

Thr Gly Glu Ile Ser Glu Lys Val Lys Leu Gly Thr Lys Ala Leu Ala
            610                 615                 620

Gly Gln Trp Leu Ala Tyr Gly Val Thr Arg Trp Val Thr Lys Arg Ser
625                 630                 635                 640

Val Met Thr Leu Ala Tyr Gly Ser Lys Glu Phe Gly Phe Arg Gln Gln
                645                 650                 655

Val Leu Glu Phe Thr Ile Gln Pro Ala Ile Asp Ser Gly Lys Gly Leu
                660                 665                 670

Met Phe Thr Gln Pro Asn Gln Ala Ala Gly Tyr Met Ala Lys Leu Ile
            675                 680                 685

Trp Glu Ser Val Ser Val Thr Val Val Ala Ala Val Glu Ala Met Asn
690                 695                 700

Trp Leu Lys Ser Ala Ala Lys Leu Leu Ala Ala Glu Val Lys Asp Lys
705                 710                 715                 720

Lys Thr Gly Glu Ile Leu Arg Lys Arg Cys Ala Val His Trp Val Thr
                725                 730                 735

Pro Asp Gly Phe Pro Val Trp Gln Glu Tyr Lys Lys Pro Ile Gln Thr
            740                 745                 750

Arg Leu Asn Leu Met Phe Leu Gly Gln Phe Arg Leu Gln Pro Thr Ile
            755                 760                 765

Asn Thr Asn Lys Asp Ser Glu Ile Asp Ala His Lys Gln Glu Ser Gly
770                 775                 780

Ile Ala Pro Asn Phe Val His Ser Gln Asp Gly Ser His Leu Arg Lys
785                 790                 795                 800

Thr Val Val Trp Ala His Glu Lys Tyr Gly Ile Glu Ser Phe Ala Leu
                805                 810                 815

Ile His Asp Ser Phe Gly Thr Ile Pro Ala Asp Ala Ala Asn Leu Phe
                820                 825                 830

Lys Ala Val Arg Glu Thr Met Val Asp Thr Tyr Glu Ser Cys Asp Val
            835                 840                 845

Leu Ala Asp Phe Tyr Asp Gln Phe Ala Asp Gln Leu His Glu Ser Gln
```

```
                850               855                860
Leu Asp Lys Met Pro Ala Leu Pro Ala Lys Gly Asn Leu Asn Leu Arg
865                 870                 875                 880
Asp Ile Leu Glu Ser Asp Phe Ala Phe Ala
                885                 890

<210> SEQ ID NO 32
<211> LENGTH: 2673
<212> TYPE: DNA
<213> ORGANISM: Artificial Sequence
<220> FEATURE:
<223> OTHER INFORMATION: T7RNAP variant

<400> SEQUENCE: 32
atgcaccatc accatcacca tatgaacacg attaacatcg ctaagaacga cttctctgac      60
atcgaactgg ctgctatccc gttcaacact ctggctgacc attacggtga gcgtttagct     120
cgcgaacagt tggcccttga gcatgagtct tacgagatgg gtgaagcacg cttccgcaag     180
atgtttgagc gtcaacttaa agctggtgag gttgcggata cgctgccgc caagcctctc     240
atcactaccc tactccctaa gatgattgca cgcatcaacg actggtttga ggaagtgaaa     300
gctaagcgcg gcaagcgccc gacagccttc cagttcctgc aagaaatcaa gccggaagcc     360
gtagcgtaca tcaccattaa gaccactctg gcttgcctaa ccagtgctga caatacaacc     420
gttcaggctg tagcaagcgc aatcggtcgg ccattgagg acgaggctcg cttcggtcgt     480
atccgtgacc ttgaagctaa gcacttcaag aaaaacgttg aggaacaact caacaagcgc     540
gtagggcacg tctacaagaa agcatttatg caagttgtcg aggctgacat gctctctaag     600
ggtctactcg gtggcgaggc gtggtcttcg tggcataagg aagactctat tcatgtagga     660
gtacgctgca tcgagatgct cattgagtca accggaatgg ttagcttaca ccgccaaaat     720
gctggcgtag taggtcaaga ctctgagact atcgaactcg cacctgaata cgctgaggct     780
atcgcaaccc gtgcaggtgc gctggctggc atctctccga tgttccaacc ttgcgtagtt     840
cctcctaagc cgtggactgg cattactggt ggtggctatt gggctaacgg tcgtcgtcct     900
ctggcgctgt gcgtactca cagtaagaaa gcactgatgc gctacgaaga cgtttacatg     960
cctgaggtgt acaaagcgat taacattgcg caaaacaccg catggaaaat caacaagaaa    1020
gtcctagcga tcgccaacgt aatcaccaag tggaagcatt gtccggtcga ggacatccct    1080
gcgattgagc gtgaagaact cccgatgaaa ccggaagaca tcgacatgaa tcctgaggct    1140
ctcaccgcgt ggaaacgtgc tgccgctgct gtgtaccgca aggacaaggc gcgcaagtct    1200
cgccgtatca gccttgagtt catgcttgag caagccaata gtttgctaa ccataaggcc    1260
atctggttcc cttacaacat ggactggcgc ggtcgtgttt acgctgtgtc aatgttcaac    1320
ccgcaaggta acgatatgac caaaggactg cttacgctgg cgaaaggtaa accaatcggt    1380
aaggaaggtt actactggct gaaaatccac ggtgcaaact gtgcgggtgt cgataaggtt    1440
ccgttccctg agcgcatcaa gttcattgag gaaaaccacg agaacatcat ggcttgcgct    1500
aagtctccac tggagaacac ttggtgggct gagcaatatt ctccgttctg cttccttgcg    1560
ttctgctttg agtacgctgg ggtacagcac acggcctga ctataactg ctcccttccg    1620
ctggcgtttg acgggtcttg ctctggcatc cagcacttct ccgcgatgct ccgagatgag    1680
gtaggtggtc gcgcggttaa cttgcttcct agtgaaaccg ttcaggacat ctacgggatt    1740
gttgctaaga aagtcaacga gattctacaa gcagacgcaa tcaatgggac cgataacgaa    1800
gtagttaccg tgaccgatga aacactggt gaaatctctg agaaagtcaa gctgggcact    1860
```

```
aaggcactgg ctggtcaatg gctggcttac ggtgttactc gctgggtgac taagcgttca   1920
gtcatgacgc tggcttacgg gtccaaagag ttcggcttcc gtcaacaagt gctggaatac   1980
accattcagc ctgctattga ttccggcaag ggtctgatgt tcactcagcc gaatcaggct   2040
gctggataca tggctaagct gatttgggaa tctgtgagcg tgacggtggt agctgcggtt   2100
gaagcaatga actggcttaa gtctgctgct aagctgctgg ctgctgaggt caaagataag   2160
aagactggag agattcttcg caagcgttgc gctgtgcatt gggtaactcc tgatggtttc   2220
cctgtgtggc aggaatacaa gaagcctatt cagacgcgct tgaacctgat gttcctcggt   2280
cagttccgct tacagcctac cattaacacc aacaaagata gcgagattga tgcacacaaa   2340
caggagtctg gtatcgctcc taactttgta cacagccaag acggtagcca ccttcgtaag   2400
actgtagtgt gggcacacga gaagtacgga atcgaatctt ttgcactgat tcacgactcc   2460
ttcggtacca ttccggctga cgctgcgaac ctgttcaaag cagtgcgcga aactatggtt   2520
gacacatatg agtcttgtga tgtactggct gatttctacg accagttcgc tgaccagttg   2580
cacgagtctc aattggacaa aatgccagca cttccggcta aaggtaactt gaacctccgt   2640
gacatcttag agtcggactt cgcgttcgcg taa                                2673
```

<210> SEQ ID NO 33
<211> LENGTH: 890
<212> TYPE: PRT
<213> ORGANISM: Artificial Sequence
<220> FEATURE:
<223> OTHER INFORMATION: T7RNAP variant

<400> SEQUENCE: 33

```
Met His His His His His Met Asn Thr Ile Asn Ile Ala Lys Asn
1               5                   10                  15

Asp Phe Ser Asp Ile Glu Leu Ala Ala Ile Pro Phe Asn Thr Leu Ala
            20                  25                  30

Asp His Tyr Gly Glu Arg Leu Ala Arg Glu Gln Leu Ala Leu Glu His
        35                  40                  45

Glu Ser Tyr Glu Met Gly Glu Ala Arg Phe Arg Lys Met Phe Glu Arg
    50                  55                  60

Gln Leu Lys Ala Gly Glu Val Ala Asp Asn Ala Ala Ala Lys Pro Leu
65                  70                  75                  80

Ile Thr Thr Leu Leu Pro Lys Met Ile Ala Arg Ile Asn Asp Trp Phe
                85                  90                  95

Glu Glu Val Lys Ala Lys Arg Gly Lys Arg Pro Thr Ala Phe Gln Phe
            100                 105                 110

Leu Gln Glu Ile Lys Pro Glu Ala Val Ala Tyr Ile Thr Ile Lys Thr
        115                 120                 125

Thr Leu Ala Cys Leu Thr Ser Ala Asp Asn Thr Thr Val Gln Ala Val
    130                 135                 140

Ala Ser Ala Ile Gly Arg Ala Ile Glu Asp Glu Ala Arg Phe Gly Arg
145                 150                 155                 160

Ile Arg Asp Leu Glu Ala Lys His Phe Lys Lys Asn Val Glu Glu Gln
                165                 170                 175

Leu Asn Lys Arg Val Gly His Val Tyr Lys Lys Ala Phe Met Gln Val
            180                 185                 190

Val Glu Ala Asp Met Leu Ser Lys Gly Leu Leu Gly Gly Glu Ala Trp
        195                 200                 205

Ser Ser Trp His Lys Glu Asp Ser Ile His Val Gly Val Arg Cys Ile
```

-continued

```
            210                 215                 220
Glu Met Leu Ile Glu Ser Thr Gly Met Val Ser Leu His Arg Gln Asn
225                 230                 235                 240

Ala Gly Val Val Gly Gln Asp Ser Glu Thr Ile Glu Leu Ala Pro Glu
                245                 250                 255

Tyr Ala Glu Ala Ile Ala Thr Arg Ala Gly Ala Leu Ala Gly Ile Ser
                260                 265                 270

Pro Met Phe Gln Pro Cys Val Val Pro Pro Lys Pro Trp Thr Gly Ile
            275                 280                 285

Thr Gly Gly Gly Tyr Trp Ala Asn Gly Arg Arg Pro Leu Ala Leu Val
        290                 295                 300

Arg Thr His Ser Lys Lys Ala Leu Met Arg Tyr Glu Asp Val Tyr Met
305                 310                 315                 320

Pro Glu Val Tyr Lys Ala Ile Asn Ile Ala Gln Asn Thr Ala Trp Lys
                325                 330                 335

Ile Asn Lys Lys Val Leu Ala Val Ala Asn Val Ile Thr Lys Trp Lys
                340                 345                 350

His Cys Pro Val Glu Asp Ile Pro Ala Ile Glu Arg Glu Glu Leu Pro
            355                 360                 365

Met Lys Pro Glu Asp Ile Asp Met Asn Pro Glu Ala Leu Thr Ala Trp
        370                 375                 380

Lys Arg Ala Ala Ala Val Tyr Arg Lys Asp Lys Ala Arg Lys Ser
385                 390                 395                 400

Arg Arg Ile Ser Leu Glu Phe Met Leu Glu Gln Ala Asn Lys Phe Ala
                405                 410                 415

Asn His Lys Ala Ile Trp Phe Pro Tyr Asn Met Asp Trp Arg Gly Arg
                420                 425                 430

Val Tyr Ala Val Ser Met Phe Asn Pro Gln Gly Asn Asp Met Thr Lys
                435                 440                 445

Gly Leu Leu Thr Leu Ala Lys Gly Lys Pro Ile Gly Lys Glu Gly Tyr
        450                 455                 460

Tyr Trp Leu Lys Ile His Gly Ala Asn Cys Ala Gly Val Asp Lys Val
465                 470                 475                 480

Pro Phe Pro Glu Arg Ile Lys Phe Ile Glu Glu Asn His Glu Asn Ile
                485                 490                 495

Met Ala Cys Ala Lys Ser Pro Leu Glu Asn Thr Trp Trp Ala Glu Gln
                500                 505                 510

Tyr Ser Pro Phe Cys Phe Leu Ala Phe Cys Phe Glu Tyr Ala Gly Val
            515                 520                 525

Gln His His Gly Leu Ser Tyr Asn Cys Ser Leu Pro Leu Ala Phe Asp
        530                 535                 540

Gly Ser Cys Ser Gly Ile Gln His Phe Ser Ala Met Leu Arg Asp Glu
545                 550                 555                 560

Val Gly Gly Arg Ala Val Asn Leu Leu Pro Ser Glu Thr Val Gln Asp
                565                 570                 575

Ile Tyr Gly Ile Val Ala Lys Lys Val Asn Glu Ile Leu Gln Ala Asp
                580                 585                 590

Ala Ile Asn Gly Thr Asp Asn Glu Val Val Thr Val Thr Asp Glu Asn
            595                 600                 605

Thr Gly Glu Ile Ser Glu Lys Val Lys Leu Gly Thr Lys Ala Leu Ala
        610                 615                 620

Gly Gln Trp Leu Ala Tyr Gly Val Thr Arg Trp Val Thr Lys Arg Ser
625                 630                 635                 640
```

Val Met Thr Leu Ala Tyr Gly Ser Lys Glu Phe Gly Phe Arg Gln Gln
            645                 650                 655

Val Leu Glu Tyr Thr Ile Gln Pro Ala Ile Asp Ser Gly Lys Gly Leu
            660                 665                 670

Met Phe Thr Gln Pro Asn Gln Ala Ala Gly Tyr Met Ala Lys Leu Ile
            675                 680                 685

Trp Glu Ser Val Ser Val Thr Val Ala Ala Val Glu Ala Met Asn
            690                 695                 700

Trp Leu Lys Ser Ala Ala Lys Leu Leu Ala Ala Glu Val Lys Asp Lys
705                 710                 715                 720

Lys Thr Gly Glu Ile Leu Arg Lys Arg Cys Ala Val His Trp Val Thr
            725                 730                 735

Pro Asp Gly Phe Pro Val Trp Gln Glu Tyr Lys Lys Pro Ile Gln Thr
            740                 745                 750

Arg Leu Asn Leu Met Phe Leu Gly Gln Phe Arg Leu Gln Pro Thr Ile
            755                 760                 765

Asn Thr Asn Lys Asp Ser Glu Ile Asp Ala His Lys Gln Glu Ser Gly
            770                 775                 780

Ile Ala Pro Asn Phe Val His Ser Gln Asp Gly Ser His Leu Arg Lys
785                 790                 795                 800

Thr Val Val Trp Ala His Glu Lys Tyr Gly Ile Glu Ser Phe Ala Leu
            805                 810                 815

Ile His Asp Ser Phe Gly Thr Ile Pro Ala Asp Ala Ala Asn Leu Phe
            820                 825                 830

Lys Ala Val Arg Glu Thr Met Val Asp Thr Tyr Glu Ser Cys Asp Val
            835                 840                 845

Leu Ala Asp Phe Tyr Asp Gln Phe Ala Asp Gln Leu His Glu Ser Gln
            850                 855                 860

Leu Asp Lys Met Pro Ala Leu Pro Ala Lys Gly Asn Leu Asn Leu Arg
865                 870                 875                 880

Asp Ile Leu Glu Ser Asp Phe Ala Phe Ala
            885                 890

<210> SEQ ID NO 34
<211> LENGTH: 2673
<212> TYPE: DNA
<213> ORGANISM: Artificial Sequence
<220> FEATURE:
<223> OTHER INFORMATION: T7RNAP variant

<400> SEQUENCE: 34
atgcaccatc accatcacca tatgaacacg attaacatcg ctaagaacga cttctctgac     60
atcgaactgg ctgctatccc gttcaacact ctggctgacc attacggtga gcgtttagct    120
cgcgaacagt tggcccttga gcatgagtct tacgagatgg gtgaagcacg cttccgcaag    180
atgtttgagc gtcaacttaa agctggtgag gttgcggata cgctgccgc caagcctctc    240 atcactaccc tactccctaa gatgattgca cgcatcaacg actggtttga ggaagtgaaa    300
gctaagcgcg gcaagcgccc gacagccttc cagttcctgc aagaaatcaa gccggaagcc    360
gtagcgtaca tcaccattaa gaccactctg gcttgcctaa ccagtgcgga caatacaacc    420
gttcaggctg tagcaagcgc aatcggtcgg gccattgagg acgaggctcg cttcggtcgt    480
atccgtgacc ttgaagctaa gcacttcaag aaaaacgttg aggaacaact caacaagcgc    540
gtagggcacg tctacaagaa agcatttatg caagttgtcg aggctgacat gctctctaag    600

```
ggtctactcg gtggcgaggc gtggtcttcg tggcataagg aagactctat tcatgtagga    660
gtacgctgca tcgagatgct cattgagtca accggaatgg ttagcttaca ccgccaaaat    720
gctggcgtag taggtcaaga ctctgagact atcgaactcg cacctgaata cgctgaggct    780
atcgcaaccc gtgcaggtgc gctggctggc atctctccga tgttccaacc ttgcgtagtt    840
cctcctaagc cgtggactgg cattactggt ggtggctatt gggctaacgg tcgtcgtcct    900
ctggcgctgg tgcgtactca cagtaagaaa gcactgatgc gctacgaaga cgtttacatg    960
cctgaggtgt acaaagcgat taacattgcg caaaacaccg catggaaaat caacaagaaa   1020
gtcctagcgg tcgccaacgt aatcaccaag tggaagcatt gtccggtcga ggacatccct   1080
gcgattgagc gtgaagaact cccgatgaaa ccggaagaca tcgacatgaa tcctgaggct   1140
ctcaccgcgt ggaaacgtgc tgccgctgct gtgtaccgca aggacaaggc tcgcaagtct   1200
gttcgtatct atcttgagtt catgcttgag caagccaata agtttgctaa ccataaggcc   1260
atctggttcc cttacaacat ggactggcgc ggtcgtgttt acgctgtgtc aatgttcaac   1320
ccgcaaggta acgatatgac caaaggactg cttacgctgg cgaaaggtaa accaatcggt   1380
aaggaaggtt actactggct gaaaatccac ggtgcaaact gtgcgggtgt cgataaggtt   1440
ccgttccctg agcgcatcaa gttcattgag aaaaccacg agaacatcat ggcttgcgct   1500
aagtctccac tggagaacac ttggtgggct gagcaagatc tcccgttctg cttccttgcg   1560
ttctgctttg agtacgctgg ggtacagcac cacggcctga gctataactg ctcccttccg   1620
ctggcgtttg acgggtcttg ctctggcatc cagcacttct ccgcgatgct ccgagatgag   1680
gtaggtggtc gcgcggttaa cttgcttcct agtgaaaccg ttcaggacat ctacgggatt   1740
gttgctaaga aagtcaacga gattctacaa gcagacgcaa tcaatgggac cgataacgaa   1800
gtagttaccg tgaccgatga aacactggt gaaatctctg agaaagtcaa gctgggcact   1860
aaggcactgg ctggtcaatg gctggcttac ggtgttactc gcagtgtgac taagcgttca   1920
gtcatgacgc tggcttacgg gtccaaagag ttcggcttcc gtcaacaagt gctggaagac   1980
accattcagt gggctattga ttccggcaag ggtctgatgt tcactcagcc gaatcaggct   2040
gctggataca tggctaagct gatttgggaa tctgtgagcg tgacggtggt agctgcggtt   2100
gaagcaatga actggcttaa gtctgctgct aagctgctgg ctgctgaggt caaagataag   2160
aagactggag agattcttcg caagcgttgc gctgtgcatt gggtaactcc tgatggtttc   2220
cctgtgtggc aggaatacaa gaagcctatt cagacgcgct tgaacctgat gttcctcggt   2280
cagttccgct tacagcctac cattaacacc aacaaagata gcgagattga tgcacacaaa   2340
caggagtctg gtatcgctcc taactttgta cacagccaag acggtagcca ccttcgtaag   2400
actgtagtgt gggcacacga gaagtacgga atcgaatctt ttgcactgat tcacgactcc   2460
ttcggtacca ttccggctga cgctgcgaac ctgttcaaag cagtgcgcga aactatggtt   2520
gacacatatg agtcttgtga tgtactggct gatttctacg accagttcgc tgaccagttg   2580
cacgagtctc aattggacaa aatgccagca cttccggcta aggtaacttg aacctccgt   2640
gacatcttag agtcggactt cgcgttcgcg taa                                2673
```

<210> SEQ ID NO 35
<211> LENGTH: 890
<212> TYPE: PRT
<213> ORGANISM: Artificial Sequence
<220> FEATURE:
<223> OTHER INFORMATION: T7RNAP variant

<400> SEQUENCE: 35

```
Met His His His His His Met Asn Thr Ile Asn Ile Ala Lys Asn
1               5                   10                  15

Asp Phe Ser Asp Ile Glu Leu Ala Ala Ile Pro Phe Asn Thr Leu Ala
                20                  25                  30

Asp His Tyr Gly Glu Arg Leu Ala Arg Glu Gln Leu Ala Leu Glu His
            35                  40                  45

Glu Ser Tyr Glu Met Gly Glu Ala Arg Phe Arg Lys Met Phe Glu Arg
        50                  55                  60

Gln Leu Lys Ala Gly Glu Val Ala Asp Asn Ala Ala Lys Pro Leu
65                  70                  75                  80

Ile Thr Thr Leu Leu Pro Lys Met Ile Ala Arg Ile Asn Asp Trp Phe
                85                  90                  95

Glu Glu Val Lys Ala Lys Arg Gly Lys Arg Pro Thr Ala Phe Gln Phe
            100                 105                 110

Leu Gln Glu Ile Lys Pro Glu Ala Val Ala Tyr Ile Thr Ile Lys Thr
        115                 120                 125

Thr Leu Ala Cys Leu Thr Ser Ala Asp Asn Thr Thr Val Gln Ala Val
    130                 135                 140

Ala Ser Ala Ile Gly Arg Ala Ile Glu Asp Glu Ala Arg Phe Gly Arg
145                 150                 155                 160

Ile Arg Asp Leu Glu Ala Lys His Phe Lys Lys Asn Val Glu Glu Gln
                165                 170                 175

Leu Asn Lys Arg Val Gly His Val Tyr Lys Lys Ala Phe Met Gln Val
            180                 185                 190

Val Glu Ala Asp Met Leu Ser Lys Gly Leu Leu Gly Gly Glu Ala Trp
        195                 200                 205

Ser Ser Trp His Lys Glu Asp Ser Ile His Val Gly Val Arg Cys Ile
    210                 215                 220

Glu Met Leu Ile Glu Ser Thr Gly Met Val Ser Leu His Arg Gln Asn
225                 230                 235                 240

Ala Gly Val Val Gly Gln Asp Ser Glu Thr Ile Glu Leu Ala Pro Glu
                245                 250                 255

Tyr Ala Glu Ala Ile Ala Thr Arg Ala Gly Ala Leu Ala Gly Ile Ser
            260                 265                 270

Pro Met Phe Gln Pro Cys Val Val Pro Pro Lys Pro Trp Thr Gly Ile
        275                 280                 285

Thr Gly Gly Gly Tyr Trp Ala Asn Gly Arg Arg Pro Leu Ala Leu Val
    290                 295                 300

Arg Thr His Ser Lys Lys Ala Leu Met Arg Tyr Glu Asp Val Tyr Met
305                 310                 315                 320

Pro Glu Val Tyr Lys Ala Ile Asn Ile Ala Gln Asn Thr Ala Trp Lys
                325                 330                 335

Ile Asn Lys Lys Val Leu Ala Val Ala Asn Val Ile Thr Lys Trp Lys
            340                 345                 350

His Cys Pro Val Glu Asp Ile Pro Ala Ile Glu Arg Glu Glu Leu Pro
        355                 360                 365

Met Lys Pro Glu Asp Ile Asp Met Asn Pro Glu Ala Leu Thr Ala Trp
    370                 375                 380

Lys Arg Ala Ala Ala Val Tyr Arg Lys Asp Lys Ala Arg Lys Ser
385                 390                 395                 400

Val Arg Ile Tyr Leu Glu Phe Met Leu Glu Gln Ala Asn Lys Phe Ala
                405                 410                 415
```

```
Asn His Lys Ala Ile Trp Phe Pro Tyr Asn Met Asp Trp Arg Gly Arg
                420                 425                 430

Val Tyr Ala Val Ser Met Phe Asn Pro Gln Gly Asn Asp Met Thr Lys
            435                 440                 445

Gly Leu Leu Thr Leu Ala Lys Gly Lys Pro Ile Gly Lys Glu Gly Tyr
        450                 455                 460

Tyr Trp Leu Lys Ile His Gly Ala Asn Cys Ala Gly Val Asp Lys Val
465                 470                 475                 480

Pro Phe Pro Glu Arg Ile Lys Phe Ile Glu Glu Asn His Glu Asn Ile
                485                 490                 495

Met Ala Cys Ala Lys Ser Pro Leu Glu Asn Thr Trp Trp Ala Glu Gln
            500                 505                 510

Asp Leu Pro Phe Cys Phe Leu Ala Phe Cys Phe Glu Tyr Ala Gly Val
        515                 520                 525

Gln His His Gly Leu Ser Tyr Asn Cys Ser Leu Pro Leu Ala Phe Asp
    530                 535                 540

Gly Ser Cys Ser Gly Ile Gln His Phe Ser Ala Met Leu Arg Asp Glu
545                 550                 555                 560

Val Gly Gly Arg Ala Val Asn Leu Leu Pro Ser Glu Thr Val Gln Asp
                565                 570                 575

Ile Tyr Gly Ile Val Ala Lys Lys Val Asn Glu Ile Leu Gln Ala Asp
            580                 585                 590

Ala Ile Asn Gly Thr Asp Asn Glu Val Val Thr Val Thr Asp Glu Asn
        595                 600                 605

Thr Gly Glu Ile Ser Glu Lys Val Lys Leu Gly Thr Lys Ala Leu Ala
    610                 615                 620

Gly Gln Trp Leu Ala Tyr Gly Val Thr Arg Ser Val Thr Lys Arg Ser
625                 630                 635                 640

Val Met Thr Leu Ala Tyr Gly Ser Lys Glu Phe Gly Phe Arg Gln Gln
                645                 650                 655

Val Leu Glu Asp Thr Ile Gln Trp Ala Ile Asp Ser Gly Lys Gly Leu
            660                 665                 670

Met Phe Thr Gln Pro Asn Gln Ala Ala Gly Tyr Met Ala Lys Leu Ile
        675                 680                 685

Trp Glu Ser Val Ser Val Thr Val Val Ala Ala Val Glu Ala Met Asn
    690                 695                 700

Trp Leu Lys Ser Ala Ala Lys Leu Leu Ala Ala Glu Val Lys Asp Lys
705                 710                 715                 720

Lys Thr Gly Glu Ile Leu Arg Lys Arg Cys Ala Val His Trp Val Thr
                725                 730                 735

Pro Asp Gly Phe Pro Val Trp Gln Glu Tyr Lys Lys Pro Ile Gln Thr
            740                 745                 750

Arg Leu Asn Leu Met Phe Leu Gly Gln Phe Arg Leu Gln Pro Thr Ile
        755                 760                 765

Asn Thr Asn Lys Asp Ser Glu Ile Asp Ala His Lys Gln Glu Ser Gly
    770                 775                 780

Ile Ala Pro Asn Phe Val His Ser Gln Asp Gly Ser His Leu Arg Lys
785                 790                 795                 800

Thr Val Val Trp Ala His Glu Lys Tyr Gly Ile Glu Ser Phe Ala Leu
                805                 810                 815

Ile His Asp Ser Phe Gly Thr Ile Pro Ala Asp Ala Ala Asn Leu Phe
            820                 825                 830

Lys Ala Val Arg Glu Thr Met Val Asp Thr Tyr Glu Ser Cys Asp Val
```

```
                 835                 840                 845
Leu Ala Asp Phe Tyr Asp Gln Phe Ala Asp Gln Leu His Glu Ser Gln
        850                 855                 860

Leu Asp Lys Met Pro Ala Leu Pro Ala Lys Gly Asn Leu Asn Leu Arg
865                 870                 875                 880

Asp Ile Leu Glu Ser Asp Phe Ala Phe Ala
                885                 890

<210> SEQ ID NO 36
<211> LENGTH: 2673
<212> TYPE: DNA
<213> ORGANISM: Artificial Sequence
<220> FEATURE:
<223> OTHER INFORMATION: T7RNAP variant

<400> SEQUENCE: 36
atgcaccatc accatcacca tatgaacacg attaacatcg ctaagaacga cttctctgac      60
atcgaactgg ctgctatccc gttcaacact ctggctgacc attacggtga gcgtttagct     120
cgcgaacagt tggcccttga gcatgagtct acgagatggg tgaagcacg cttccgcaag     180 atgtttgagc gtcaacttaa agctggtgag gttgcggata cgctgccgc caagcctctc     240 atcactaccc tactccctaa gatgattgca cgcatcaacg actggtttga ggaagtgaaa     300
gctaagcgcg gcaagcgccc gacagccttc cagttcctgc aagaaatcaa gccggaagcc     360
gtagcgtaca tcaccattaa gaccactctg gcttgcctaa ccagtgcgga caatacaacc     420
gttcaggctg tagcaagcgc aatcggtcgg gccattgagg acgaggctcg cttcggtcgt     480
atccgtgacc ttgaagctaa gcacttcaag aaaaacgttg aggaacaact caacaagcgc     540
gtagggcacg tctacaagaa agcatttatg caagttgtcg aggctgacat gctctctaag     600
ggtctactcg gtggcgaggc gtggtcttcg tggcataagg aagactctat tcatgtagga     660
gtacgctgca tcgagatgct cattgagtca accggaatgg ttagcttaca ccgccaaaat     720
gctggcgtag taggtcaaga ctctgagact atcgaactcg cacctgaata cgctgaggct     780
atcgcaaccc gtgcaggtgc gctggctggc atctctccga tgttccaacc ttgcgtagtt     840
cctcctaagc cgtggactgg cattactggt ggtggctatt gggctaacgg tcgtcgtcct     900
ctggcgctgg tgcgtactca cagtaagaaa gcactgatgc gctacgaaga cgtttacatg     960
cctgaggtgt acaaagcgat taacattgcg caaacaccg catggaaaat caacaagaaa    1020
gtcctagcgg tcgccaacgt aatcaccaag tggaagcatt gtccggtccg ggacatccct    1080
gcgattgagc gtgaagaact cccgatgaaa ccggaagaca tcgacatgaa tcctgaggct    1140
ctcaccgcgt ggaaacgtgc tgccgctgct gtgtaccgca gagacaaggc tcgcaagtct    1200
gttcgtatct atcttgagtt catgcttgag caagccaata gtttgctaa ccataaggcc    1260 atctggttcc cttacaacat ggactggcgc ggtcgtgttt acgctgtgtc aatgttcaac    1320
ccgcaaggta cgatatgac caaaggactg cttacgctgg cgaaaggtaa accaatcggt    1380
aaggaaggtt actactggct gaaaatccac ggtgcaaact gtgcgggtgt cgataaggtt    1440
ccgttccctg agcgcatcaa gttcattgag gaaaaccacg agaacatcat ggcttgcgct    1500
aagtctccac tggagaacac ttggtgggct gagcaagatc tcccgttctg cttccttgcg    1560
ttctgctttg agtacgctgg ggtacagcac cacggcctga gctataactg ctcccttccg    1620
ctggcgtttg acgggtcttg ctctggcatc cagcacttct ccgcgatgct ccgagatgag    1680
gtaggtggtc gcgcggttaa cttgcttcct agtgaaaccg ttcaggacat ctacgggatt    1740
```

```
gttgctaaga aagtcaacga gattctacaa gcagacgcaa tcaatgggac cgataacgaa    1800
gtagttaccg tgaccgatga gaacactggt gaaatctctg agaaagtcaa gctgggcact    1860
aaggcactgg ctggtcaatg gctggcttac ggtgttactc gcagtgtgac taagcgttca    1920
gtcatgacgc tggcttacgg gtccaaagag ttcggcttcc gtcaacaagt gctggaagat    1980
actattcagt gggctattga ttccggcaag ggtctgatgt tcactcagcc gaatcaggct    2040
gctggataca tggctaagct gatttgggaa tctgtgagcg tgacggtggt agctgcggtt    2100
gaagcaatga actggcttaa gtctgctgct aagctgctgg ctgctgaggt caaagataag    2160
aagactggag agattcttcg caagcgttgc gctgtgcatt gggtaactcc tgatggtttc    2220
cctgtgtggc aggaatacaa gaagcctatt cagacgcgct tgaacctgat gttcctcggt    2280
cagttccgct tacagcctac cattaacacc aacaaagata gcgagattga tgcacacaaa    2340
caggagtctg gtatcgctcc taactttgta cacagccaag acggtagcca ccttcgtaag    2400
actgtagtgt gggcacacga gaagtacgga atcgaatctt ttgcactgat tcacgactcc    2460
ttcggtacca ttccggctga cgctgcgaac ctgttcaaag cagtgcgcga aactatggtt    2520
gacacatatg agtcttgtga tgtactggct gatttctacg accagttcgc tgaccagttg    2580
cacgagtctc aattggacaa aatgccagca cttccggcta aaggtaactt gaacctccgt    2640
gacatcttag agtcggactt cgcgttcgcg taa                                  2673
```

```
<210> SEQ ID NO 37
<211> LENGTH: 890
<212> TYPE: PRT
<213> ORGANISM: Artificial Sequence
<220> FEATURE:
<223> OTHER INFORMATION: T7RNAP variant

<400> SEQUENCE: 37

Met His His His His His His Met Asn Thr Ile Asn Ile Ala Lys Asn
1               5                   10                  15

Asp Phe Ser Asp Ile Glu Leu Ala Ala Ile Pro Phe Asn Thr Leu Ala
            20                  25                  30

Asp His Tyr Gly Glu Arg Leu Ala Arg Glu Gln Leu Ala Leu Glu His
        35                  40                  45

Glu Ser Tyr Glu Met Gly Glu Ala Arg Phe Arg Lys Met Phe Glu Arg
    50                  55                  60

Gln Leu Lys Ala Gly Glu Val Ala Asp Asn Ala Ala Lys Pro Leu
65                  70                  75                  80

Ile Thr Thr Leu Leu Pro Lys Met Ile Ala Arg Ile Asn Asp Trp Phe
                85                  90                  95

Glu Glu Val Lys Ala Lys Arg Gly Lys Arg Pro Thr Ala Phe Gln Phe
            100                 105                 110

Leu Gln Glu Ile Lys Pro Glu Ala Val Ala Tyr Ile Thr Ile Lys Thr
        115                 120                 125

Thr Leu Ala Cys Leu Thr Ser Ala Asp Asn Thr Thr Val Gln Ala Val
    130                 135                 140

Ala Ser Ala Ile Gly Arg Ala Ile Glu Asp Glu Ala Arg Phe Gly Arg
145                 150                 155                 160

Ile Arg Asp Leu Glu Ala Lys His Phe Lys Lys Asn Val Glu Glu Gln
                165                 170                 175

Leu Asn Lys Arg Val Gly His Val Tyr Lys Lys Ala Phe Met Gln Val
            180                 185                 190

Val Glu Ala Asp Met Leu Ser Lys Gly Leu Leu Gly Gly Glu Ala Trp
```

```
                195                 200                 205
Ser Ser Trp His Lys Glu Asp Ser Ile His Val Gly Val Arg Cys Ile
210                 215                 220

Glu Met Leu Ile Glu Ser Thr Gly Met Val Ser Leu His Arg Gln Asn
225                 230                 235                 240

Ala Gly Val Val Gly Gln Asp Ser Glu Thr Ile Glu Leu Ala Pro Glu
                245                 250                 255

Tyr Ala Glu Ala Ile Ala Thr Arg Ala Gly Ala Leu Ala Gly Ile Ser
                260                 265                 270

Pro Met Phe Gln Pro Cys Val Val Pro Pro Lys Pro Trp Thr Gly Ile
                275                 280                 285

Thr Gly Gly Gly Tyr Trp Ala Asn Gly Arg Arg Pro Leu Ala Leu Val
                290                 295                 300

Arg Thr His Ser Lys Lys Ala Leu Met Arg Tyr Glu Asp Val Tyr Met
305                 310                 315                 320

Pro Glu Val Tyr Lys Ala Ile Asn Ile Ala Gln Asn Thr Ala Trp Lys
                325                 330                 335

Ile Asn Lys Lys Val Leu Ala Val Ala Asn Val Ile Thr Lys Trp Lys
                340                 345                 350

His Cys Pro Val Arg Asp Ile Pro Ala Ile Glu Arg Glu Glu Leu Pro
                355                 360                 365

Met Lys Pro Glu Asp Ile Asp Met Asn Pro Gly Ala Leu Thr Ala Trp
370                 375                 380

Lys Arg Ala Ala Ala Val Tyr Arg Arg Asp Lys Ala Arg Lys Ser
385                 390                 395                 400

Val Arg Ile Tyr Leu Glu Phe Met Leu Glu Gln Ala Asn Lys Phe Ala
                405                 410                 415

Asn His Lys Ala Ile Trp Phe Pro Tyr Asn Met Asp Trp Arg Gly Arg
                420                 425                 430

Val Tyr Ala Val Ser Met Phe Asn Pro Gln Gly Asn Asp Met Thr Lys
                435                 440                 445

Gly Leu Leu Thr Leu Ala Lys Gly Lys Pro Ile Gly Lys Glu Gly Tyr
450                 455                 460

Tyr Trp Leu Lys Ile His Gly Ala Asn Cys Ala Gly Val Asp Lys Val
465                 470                 475                 480

Pro Phe Pro Glu Arg Ile Lys Phe Ile Glu Glu Asn His Glu Asn Ile
                485                 490                 495

Met Ala Cys Ala Lys Ser Pro Leu Glu Asn Thr Trp Trp Ala Glu Gln
                500                 505                 510

Asp Leu Pro Phe Cys Phe Leu Ala Phe Cys Phe Glu Tyr Ala Gly Val
                515                 520                 525

Gln His His Gly Leu Ser Tyr Asn Cys Ser Leu Pro Leu Ala Phe Asp
                530                 535                 540

Gly Ser Cys Ser Gly Ile Gln His Phe Ser Ala Met Leu Arg Asp Glu
545                 550                 555                 560

Val Gly Gly Arg Ala Val Asn Leu Leu Pro Ser Glu Thr Val Gln Asp
                565                 570                 575

Ile Tyr Gly Ile Val Ala Lys Lys Val Asn Glu Ile Leu Gln Ala Asp
                580                 585                 590

Ala Ile Asn Gly Thr Asp Asn Glu Val Val Thr Val Thr Asp Glu Asn
                595                 600                 605

Thr Gly Glu Ile Ser Glu Lys Val Lys Leu Gly Thr Lys Ala Leu Ala
610                 615                 620
```

```
Gly Gln Trp Leu Ala Tyr Gly Val Thr Arg Ser Val Thr Lys Arg Ser
625                 630                 635                 640

Val Met Thr Leu Ala Tyr Gly Ser Lys Glu Phe Gly Phe Arg Gln Gln
                645                 650                 655

Val Leu Glu Asp Thr Ile Gln Trp Ala Ile Asp Ser Gly Lys Gly Leu
            660                 665                 670

Met Phe Thr Gln Pro Asn Gln Ala Ala Gly Tyr Met Ala Lys Leu Ile
        675                 680                 685

Trp Glu Ser Val Ser Val Thr Val Ala Ala Val Glu Ala Met Asn
    690                 695                 700

Trp Leu Lys Ser Ala Ala Lys Leu Leu Ala Ala Glu Val Lys Asp Lys
705                 710                 715                 720

Lys Thr Gly Glu Ile Leu Arg Lys Arg Cys Ala Val His Trp Val Thr
                725                 730                 735

Pro Asp Gly Phe Pro Val Trp Gln Glu Tyr Lys Lys Pro Ile Gln Thr
            740                 745                 750

Arg Leu Asn Leu Met Phe Leu Gly Gln Phe Arg Leu Gln Pro Thr Ile
        755                 760                 765

Asn Thr Asn Lys Asp Ser Glu Ile Asp Ala His Lys Gln Glu Ser Gly
    770                 775                 780

Ile Ala Pro Asn Phe Val His Ser Gln Asp Gly Ser His Leu Arg Lys
785                 790                 795                 800

Thr Val Val Trp Ala His Glu Lys Tyr Gly Ile Glu Ser Phe Ala Leu
                805                 810                 815

Ile His Asp Ser Phe Gly Thr Ile Pro Ala Asp Ala Ala Asn Leu Phe
            820                 825                 830

Lys Ala Val Arg Glu Thr Met Val Asp Thr Tyr Glu Ser Cys Asp Val
        835                 840                 845

Leu Ala Asp Phe Tyr Asp Gln Phe Ala Asp Gln Leu His Glu Ser Gln
    850                 855                 860

Leu Asp Lys Met Pro Ala Leu Pro Ala Lys Gly Asn Leu Asn Leu Arg
865                 870                 875                 880

Asp Ile Leu Glu Ser Asp Phe Ala Phe Ala
                885                 890

<210> SEQ ID NO 38
<211> LENGTH: 2673
<212> TYPE: DNA
<213> ORGANISM: Artificial Sequence
<220> FEATURE:
<223> OTHER INFORMATION: T7RNAP variant

<400> SEQUENCE: 38
atgcaccatc accatcacca tatgaacacg attaacatcg ctaagaacga cttctctgac      60
atcgaactgg ctgctatccc gttcaacact ctggctgacc attacggtga gcgtttagct     120
cgcgaacagt tggcccttga gcatgagtct tacgagatgg gtgaagcacg cttccgcaag     180
atgtttgagc gtcaacttaa agctggtgag gttgcggata cgctgccgc caagcctctc     240 atcactaccc tactccctaa gatgattgca cgcatcaacg actggtttga ggaagtgaaa     300
gctaagcgcg gcaagcgccc gacagccttc cagttcctgc aagaaatcaa gccggaagcc     360
gtagcgtaca tcaccattaa gaccactctg gcttgcctaa ccagtgctga caatacaacc     420
gttcaggctg tagcaagcgc aatcggtcgg gccattgagg acgaggctcg cttcggtcgt     480
atccgtgacc ttgaagctaa gcacttcaag aaaaacgttg aggaacaact caacaagcgc     540
```

```
gtagggcacg tctacaagaa agcatttatg caagttgtcg aggctgacat gctctctaag      600
ggtctactcg gtggcgaggc gtggtcttcg tggcataagg aagactctat tcatgtagga      660
gtacgctgca tcgagatgct cattgagtca accggaatgg ttagcttaca ccgccaaaat      720
gctggcgtag taggtcaaga ctctgagact atcgaactcg cacctgaata cgctgaggct      780
atcgcaaccc gtgcaggtgc gctggctggc atctctccga tgttccaacc ttgcgtagtt      840
cctcctaagc cgtggactgg cattactggt ggtggctatt gggctaacgg tcgtcgtcct      900
ctggcgctgg tgcgtactca cagtaagaaa gcactgatgc gctacgaaga cgtttacatg      960
cctgaggtgt acaaagcgat taacattgcg caaaacaccg catggaaaat caacaagaaa     1020
gtcctagcgg tcgccaacgt aatcaccaag tggaagcatt gtccggtcga ggacatccct     1080
gcgattgagc gtgaagaact cccgatgaaa ccggaagaca tcgacatgaa tcctgaggct     1140
ctcaccgcgt ggaaacgtgc tgccgctgct gtgtaccgca aggacaaggc gcgcaagtct     1200
cgccgtatca gccttgagtt catgcttgag caagccaata agtttgctaa ccataaggcc     1260
atctggttcc cttacaacat ggactggcgc ggtcgtgttt acgctgtgtc aatgttcaac     1320
ccgcaaggta acgatatgac caaaggactg cttacgctgg cgaaaggtaa accaatcggt     1380
aaggaaggtt actactggct gaaaatccac ggtgcaaact gtgcgggtgt cgataaggtt     1440
ccgttccctg agcgcatcaa gttcattgag gaaaaccacg agaacatcat ggcttgcgct     1500
aagtctccac tggagaacac ttggtgggct gagcaatatt ctccgttctg cttccttgcg     1560
ttctgctttg agtacgctgg ggtacagcac cacggcctga gctataactg ctcccttccg     1620
ctggcgtttg acgggtcttg ctctggcatc cagcacttct ccgcgatgct ccgagatgag     1680
gtaggtggtc gcgcggttaa cttgcttcct agtgaaaccg ttcaggacat ctacgggatt     1740
gttgctaaga aagtcaacga gattctacaa gcagacgcaa tcaatgggac cgataacgaa     1800
gtagttaccg tgaccgatga gaacactggt gaaatctctg agaaagtcaa gctgggcact     1860
aaggcactgg ctggtcaatg gctggcttac ggtgttactc gctgggtgac taagcgttca     1920
gtcatgacgc tggcttacgg gtccaaagag ttcggcttcc gtcaacaagt gctggaattc     1980
accattcagc ctgctattga ttccggcaag ggtctgatgt tcactcagcc gaatcaggct     2040
gctggataca tggctaagct gatttgggaa tctgtgagcg tgacggtggt agctgcggtt     2100
gaagcaatga actggcttaa gtctgctgct aagctgctgg ctgctgaggt caaagataag     2160
aagactggag agattcttcg caagcgttgc gctgtgcatt gggtaactcc tgatggtttc     2220
cctgtgtggc aggaatacaa gaagcctatt cagacgcgct tgaacctgat gttcctcggt     2280
cagttccgct tacagcctac cattaacacc aacaaagata gcgagattga tgcacacaaa     2340
caggagtctg gtatcgctcc taactttgta cacagccaag acgtagcca ccttcgtaag     2400 actgtagtgt gggcacacga gaagtacgga atcgaatctt ttgcactgat tcacgactcc     2460
ttcggtacca ttccggctga cgctgcgaac ctgttcaaag cagtgcgcga aactatggtt     2520
gacacatatg agtcttgtga tgtactggct gatttctacg accagttcgc tgaccagttg     2580
cacgagtctc aattggacaa aatgccagca cttccggcta aaggtaactt gaacctccgt     2640
gacatcttag agtcggactt cgcgttcgcg taa                                   2673
```

<210> SEQ ID NO 39
<211> LENGTH: 890
<212> TYPE: PRT
<213> ORGANISM: Artificial Sequence
<220> FEATURE:

<223> OTHER INFORMATION: T7RNAP variant

<400> SEQUENCE: 39

```
Met His His His His His Met Asn Thr Ile Asn Ile Ala Lys Asn
1               5                   10                  15

Asp Phe Ser Asp Ile Glu Leu Ala Ala Ile Pro Phe Asn Thr Leu Ala
            20                  25                  30

Asp His Tyr Gly Glu Arg Leu Ala Arg Glu Gln Leu Ala Leu Glu His
        35                  40                  45

Glu Ser Tyr Glu Met Gly Glu Ala Arg Phe Arg Lys Met Phe Glu Arg
    50                  55                  60

Gln Leu Lys Ala Gly Glu Val Ala Asp Asn Ala Ala Lys Pro Leu
65                  70                  75                  80

Ile Thr Thr Leu Leu Pro Lys Met Ile Ala Arg Ile Asn Asp Trp Phe
                85                  90                  95

Glu Glu Val Lys Ala Lys Arg Gly Lys Arg Pro Thr Ala Phe Gln Phe
            100                 105                 110

Leu Gln Glu Ile Lys Pro Glu Ala Val Ala Tyr Ile Thr Ile Lys Thr
        115                 120                 125

Thr Leu Ala Cys Leu Thr Ser Ala Asp Asn Thr Thr Val Gln Ala Val
    130                 135                 140

Ala Ser Ala Ile Gly Arg Ala Ile Glu Asp Glu Ala Arg Phe Gly Arg
145                 150                 155                 160

Ile Arg Asp Leu Glu Ala Lys His Phe Lys Lys Asn Val Glu Glu Gln
                165                 170                 175

Leu Asn Lys Arg Val Gly His Val Tyr Lys Lys Ala Phe Met Gln Val
            180                 185                 190

Val Glu Ala Asp Met Leu Ser Lys Gly Leu Leu Gly Gly Glu Ala Trp
        195                 200                 205

Ser Ser Trp His Lys Glu Asp Ser Ile His Val Gly Val Arg Cys Ile
    210                 215                 220

Glu Met Leu Ile Glu Ser Thr Gly Met Val Ser Leu His Arg Gln Asn
225                 230                 235                 240

Ala Gly Val Val Gly Gln Asp Ser Glu Thr Ile Glu Leu Ala Pro Glu
                245                 250                 255

Tyr Ala Glu Ala Ile Ala Thr Arg Ala Gly Ala Leu Ala Gly Ile Ser
            260                 265                 270

Pro Met Phe Gln Pro Cys Val Val Pro Pro Lys Pro Trp Thr Gly Ile
        275                 280                 285

Thr Gly Gly Gly Tyr Trp Ala Asn Gly Arg Arg Pro Leu Ala Leu Val
    290                 295                 300

Arg Thr His Ser Lys Lys Ala Leu Met Arg Tyr Glu Asp Val Tyr Met
305                 310                 315                 320

Pro Glu Val Tyr Lys Ala Ile Asn Ile Ala Gln Asn Thr Ala Trp Lys
                325                 330                 335

Ile Asn Lys Lys Val Leu Ala Val Ala Asn Val Ile Thr Lys Trp Lys
            340                 345                 350

His Cys Pro Val Glu Asp Ile Pro Ala Ile Glu Arg Glu Glu Leu Pro
        355                 360                 365

Met Lys Pro Glu Asp Ile Asp Met Asn Pro Glu Ala Leu Thr Ala Trp
    370                 375                 380

Lys Arg Ala Ala Ala Ala Val Tyr Arg Lys Asp Lys Ala Arg Lys Ser
385                 390                 395                 400
```

```
Arg Arg Ile Ser Leu Glu Phe Met Leu Glu Gln Ala Asn Lys Phe Ala
            405                 410                 415

Asn His Lys Ala Ile Trp Phe Pro Tyr Asn Met Asp Trp Arg Gly Arg
        420                 425                 430

Val Tyr Ala Val Ser Met Phe Asn Pro Gln Gly Asn Asp Met Thr Lys
        435                 440                 445

Gly Leu Leu Thr Leu Ala Lys Gly Lys Pro Ile Gly Lys Glu Gly Tyr
    450                 455                 460

Tyr Trp Leu Lys Ile His Gly Ala Asn Cys Ala Gly Val Asp Lys Val
465                 470                 475                 480

Pro Phe Pro Glu Arg Ile Lys Phe Ile Glu Glu Asn His Glu Asn Ile
                485                 490                 495

Met Ala Cys Ala Lys Ser Pro Leu Glu Asn Thr Trp Trp Ala Glu Gln
            500                 505                 510

Tyr Ser Pro Phe Cys Phe Leu Ala Phe Cys Phe Glu Tyr Ala Gly Val
        515                 520                 525

Gln His His Gly Leu Ser Tyr Asn Cys Ser Leu Pro Leu Ala Phe Asp
    530                 535                 540

Gly Ser Cys Ser Gly Ile Gln His Phe Ser Ala Met Leu Arg Asp Glu
545                 550                 555                 560

Val Gly Gly Arg Ala Val Asn Leu Leu Pro Ser Glu Thr Val Gln Asp
                565                 570                 575

Ile Tyr Gly Ile Val Ala Lys Lys Val Asn Glu Ile Leu Gln Ala Asp
            580                 585                 590

Ala Ile Asn Gly Thr Asp Asn Glu Val Val Thr Val Thr Asp Glu Asn
        595                 600                 605

Thr Gly Glu Ile Ser Glu Lys Val Lys Leu Gly Thr Lys Ala Leu Ala
    610                 615                 620

Gly Gln Trp Leu Ala Tyr Gly Val Thr Arg Trp Val Thr Lys Arg Ser
625                 630                 635                 640

Val Met Thr Leu Ala Tyr Gly Ser Lys Glu Phe Gly Phe Arg Gln Gln
                645                 650                 655

Val Leu Glu Phe Thr Ile Gln Pro Ala Ile Asp Ser Gly Lys Gly Leu
            660                 665                 670

Met Phe Thr Gln Pro Asn Gln Ala Ala Gly Tyr Met Ala Lys Leu Ile
        675                 680                 685

Trp Glu Ser Val Ser Val Thr Val Ala Ala Val Glu Ala Met Asn
    690                 695                 700

Trp Leu Lys Ser Ala Ala Lys Leu Leu Ala Ala Glu Val Lys Asp Lys
705                 710                 715                 720

Lys Thr Gly Glu Ile Leu Arg Lys Arg Cys Ala Val His Trp Val Thr
                725                 730                 735

Pro Asp Gly Phe Pro Val Trp Gln Glu Tyr Lys Lys Pro Ile Gln Thr
            740                 745                 750

Arg Leu Asn Leu Met Phe Leu Gly Gln Phe Arg Leu Gln Pro Thr Ile
        755                 760                 765

Asn Thr Asn Lys Asp Ser Glu Ile Asp Ala His Lys Gln Glu Ser Gly
    770                 775                 780

Ile Ala Pro Asn Phe Val His Ser Gln Asp Gly Ser His Leu Arg Lys
785                 790                 795                 800

Thr Val Val Trp Ala His Glu Lys Tyr Gly Ile Glu Ser Phe Ala Leu
                805                 810                 815

Ile His Asp Ser Phe Gly Thr Ile Pro Ala Asp Ala Ala Asn Leu Phe
```

```
                820               825               830
Lys Ala Val Arg Glu Thr Met Val Asp Thr Tyr Glu Ser Cys Asp Val
            835                 840                 845

Leu Ala Asp Phe Tyr Asp Gln Phe Ala Asp Gln Leu His Glu Ser Gln
    850                 855                 860

Leu Asp Lys Met Pro Ala Leu Pro Ala Lys Gly Asn Leu Asn Leu Arg
865                 870                 875                 880

Asp Ile Leu Glu Ser Asp Phe Ala Phe Ala
                885             890

<210> SEQ ID NO 40
<211> LENGTH: 25
<212> TYPE: DNA
<213> ORGANISM: Artificial Sequence
<220> FEATURE:
<223> OTHER INFORMATION: Substrate etc

<400> SEQUENCE: 40
tttttttttt tttttttttt ttttt                                     25
```

T7 RNA POLYMERASE VARIANTS

The present application is a Divisional of co-pending U.S. patent application Ser. No. 16/012,462, filed Jun. 19, 2018, which claims priority U.S. Prov. Pat. Appln. Ser. No. 62/527, 740, filed Jun. 30, 2017, and U.S. Prov. Pat. Appln. Ser. No. 62/528,840, filed Jul. 5, 2017, all of which are incorporated by reference in their entireties for all purposes.

FIELD OF THE INVENTION

The present invention provides engineered RNA polymerase variants and compositions comprising these variants. The present invention further provides engineered T7 RNA polymerase variants and compositions comprising these variants. These variants have been evolved for selective incorporation of the m7G(5')ppp(5')m7G cap analog over GTP at the initiation of in vitro transcription. The present invention also provides methods for selective capping of RNA transcripts.

REFERENCE TO SEQUENCE LISTING, TABLE OR COMPUTER PROGRAM

The official copy of the Sequence Listing is submitted concurrently with the specification as an ASCII formatted text file via EFS-Web, with a file name of "CX8-168USP1_ST25.txt", a creation date of Jul. 5, 2017, and a size of 184,320 bytes. The Sequence Listing filed via EFS-Web is part of the specification and is incorporated in its entirety by reference herein.

BACKGROUND OF THE INVENTION

RNA polymerases, also referred to as "DNA-dependent RNA polymerases" transcribe DNA into RNA transcripts. These enzymes represent the primary machinery that drives transcription. RNA polymerases have been isolated and purified sufficiently that they are useful for producing RNA in vitro. In vitro transcription is a procedure that allows for DNA-directed synthesis of RNA molecules of any sequence, ranging in size from short oligonucleotides to several kilobases. Typically, in vitro transcription involves engineering of a template that includes a bacteriophage promoter sequence (e.g., from the T7 coliphage) upstream of the sequence of interest followed by transcription using the corresponding RNA polymerase. Often, these RNA transcripts are subsequently modified (e.g., by capping, splicing, the addition of a poly-A tail, etc.). These transcripts are used in analytical techniques (e.g., hybridization analysis), structural studies (e.g., NMR and X-ray crystallography), in biochemical and genetic studies (e.g., as antisense reagents), as functional molecules (e.g., ribozymes and aptamers), and as therapeutic agents.

In addition, the development of mRNA as a therapeutic agent for enzyme replacement therapy has highlighted significant commercial hurdles that exist for the cost-effective, commercial production of mRNA, including efficient production of modified mRNA.

SUMMARY OF THE INVENTION

The present invention provides engineered T7 RNA polymerase variants and compositions thereof. These variants have been evolved for selective incorporation of the m7G (5')ppp(5')m7G cap analog over GTP at the initiation of in vitro transcription. The present invention also provides methods for selective capping of RNA transcripts. In addition, the present invention provides methods and compositions comprising the RNA polymerase variants provided herein.

The present invention provides engineered RNA polymerases comprising polypeptide sequences having at least 85%, 90%, 91%, 92%, 93%, 94%, 95%, 96%, 97%, 98%, 99%, or more sequence identity to the reference sequence of SEQ ID NOS: 4 and/or 15, or functional fragments thereof, wherein the engineered RNA polymerases comprise at least one substitution or substitution set in the polypeptide sequences, and wherein the amino acid positions of the polypeptide sequences are numbered with reference to SEQ ID NO:4 or 15.

In some embodiments, the engineered RNA polymerases comprise at least one substitution or substitution set is selected from 32/357, 49/642, 97/357, 136, 137, 160/643, 167/514, 250, 302/513, 314/401, 357, 392, 393, 394, 397, 401, 404, 444, 446, 478, 513, 514, 582, 635, 636, 637, 639, 642, 643, 645, 653, 656, 660, 660/806, 661, and 664, and/or any combinations thereof, wherein the amino acid positions are numbered with reference to SEQ ID NO:4. In some further embodiments, the engineered RNA polymerases comprise at least one substitution or substitution set is selected from 32V/357I, 49G/642L, 97D/357G, 136E/I, 137W, 160L/643S, 167N/514L, 250D, 302V/513G, 314C/401V, 357G/K/L/M/N/Q/R/S/T/V/W, 392D, 393L/Y, 394A/L/R, 397F/M/Q/W, 401A/I/L/S/V, 404E/Y, 444F/H/I/V, 446W/Y, 478F/M/W, 513C/F/K/L/R/T/W, 514F/I/L/Y, 582N, 635W, 636L, 637G/P/S, 639H, 642L, 643A, 645V, 653C, 656F/W, 660A/C/M/S/T/W, 660N/806Y, 661E/Y, and 664W, and/or any combinations thereof, wherein the amino acid positions are numbered with reference to SEQ ID NO:4. In some additional embodiments, the engineered RNA polymerases comprise at least one substitution or substitution set is selected from A32V/E357I, E49G/M642L, E97D/E357G, A136E/I, D137W, R160L/T643S, K167N/S514L, T250D, A302V/D513G, R314C/R401V, E357G/K/L/M/N/Q/R/S/T/V/W, Y392D, R393L/Y, K394A/L/R, A397F/M/Q/W, R401A/I/L/S/V, S404E/Y, N444F/H/I/V, M446W/Y, D478F/M/W, D513C/F/K/L/R/T/W, S514F/I/L/Y, A582N, S635W, V636L, T637G/P/S, R639H, M642L, T643A, A645V, F653C, Q656F/W, D660A/C/M/S/T/W, D660N/H806Y, T661E/Y, and P664W, and/or any combinations thereof, wherein the amino acid positions are numbered with reference to SEQ ID NO:4.

In some embodiments, the engineered RNA polymerases comprise at least one substitution or substitution set is selected from 397/513/635, 397/513/635/660, 513/660/664, 513/635/660, 513/635/664, 513/660/664, and 660/664, and/or any combinations thereof, wherein the amino acid positions are numbered with reference to SEQ ID NO: 4. In some further embodiments, the engineered RNA polymerases comprise at least one substitution or substitution set is selected from 397F/513W/635W, 397F/513Y/635W, 397W/513Y/635W, 397W/513W/635W, 397W/513Y/635W/660F, 397W/513W/635W/660W, 397Y/513W/635W/660F, 475V/513W/635W/660Y, 513F/660W/664Y, 513W/635W/660F, 513W/635W/664W, 513Y/635W/660F, 513Y/635W/660Y, 513Y/660W/664W, and 660Y/664W, and/or any combinations thereof, wherein the amino acid positions are numbered with reference to SEQ ID NO:4. In some additional embodiments, the engineered RNA polymerases comprise at least one substitution or substitution set is selected from A397F/D513W/S635W, A397F/D513Y/S635W, A397W/D513Y/S635W, A397W/D513W/S635W, A397W/D513Y/S635W/D660F, A397W/D513W/S635W/D660W, A397Y/

D513W/S635W/D660F, A475V/D513W/S635W/D660Y, D513F/D660W/P664Y, D513W/S635W/D660F, D513W/S635W/P664W, D513Y/S635W/D660F, D513Y/S635W/D660Y, D513Y/D660W/P664W, and D660Y/P664W, and/or any combinations thereof, wherein the amino acid positions are numbered with reference to SEQ ID NO:4.

In some embodiments, the engineered RNA polymerases comprise at least one substitution or substitution set is selected from 397, 397/513, 397/513/635, 397/513/635, 397/513/635/656, 397/513/635/656/660, 397/513/635/656/660/664, 397/513/635/656/664, 397/513/635/660, 397/513/635/660/664, 397/513/635/664, 397/513/656/660, 397/513/660, 397/513/660/664, 397/513/664, 397/513, 397/635, 397/635/656/660/664, 397/635/656/664, 397/635/660, 397/635/664, 397/635/664/850, 397/660, 397/664, 397/660/664, 397/837, 399/635/660, 475/513/635/660, 513, 513/635, 513/635/656, 513/635/656/660, 513/635/656/664, 513/635/660, 513/635/660/664, 513/635/664, 513/656/660, 513/656/664, 513/660, 513/660/664, 513/664, 635, 635/656, 635/656/664, 635/660, 635/660/664, 635/664, 656/660/664, 658, 660, 660/664, and 664, and/or any combinations thereof, wherein the amino acid positions are numbered with reference to SEQ ID NO:4. In some further embodiments, the engineered RNA polymerases comprise at least one substitution or substitution set is selected from 397F, 397F/513F, 397F/513F/635F, 397F/513F/635W, 397F/513F/635W/660W, 397F/513W/635W, 397F/513W/635W/656F/664F, 397F/513W/664W, 397F/513Y, 397F/513Y/635W, 397F/513Y/635W/656W, 397F/513Y/635W/664F, 37F/513Y/656H/660W, 397F/635F/660W, 397F/635W, 397F/660W, 397F/664W, 397W, 397W/513F, 397W/513F/635F/656F/660F/664W, 397W/513F/635F/660W, 397W/513F/635W, 397W/513F/660F, 397W/513F/660W, 397W/513F/660Y/664F, 397W/513W, 397W/513W/635F, 397W/513W/635F/656W/660F, 397W/513W/635W, 397W/513W/635W/656Y, 397W/513W/635W/660W, 397W/513W/635W/660W/664Y, 397W/513W/635W/660Y/664Y, 397W/513W/660W, 397W/513W/660W/664Y, 397W/513W/664F, 397W/513W/664W, 397W/513Y/635F, 397W/513Y/635W/656Y/660W/664W, 397W/513Y/635W, 397W/513Y/635W/656Y/664Y, 397W/513Y/635W/660F, 397W/635F, 397W/635F/664F, 397W/635W, 397W/635W/656F/664F, 397W/635W/656F/664W, 397W/635W/656F/664Y, 397W/635W/660W, 397W/635W/660Y, 397W/635W/664F, 397W/635W/664W/850T, 397W/660F/664F, 397W/660F/664Y, 397W/660W, 397W/837K, 397Y, 397Y/513F/635W/656F/660W/664F, 397Y/513F/635W/664W, 397Y/513W/635F/664Y, 397Y/513W/635W/660F, 397Y/513W/656W/660W, 397Y/513Y, 397Y/513Y/635W, 397Y/635F, 397Y/635F/660W, 397Y/635W, 397Y/635W/656F/660Y/664W, 397Y/635W/660F, 397Y/660F/664W, 397Y/664F, 399E/635F/660W, 475V/513W/635W/660Y, 513F, 513F/635F, 513F/635W, 513F/635W/656W, 513F/635W/664W, 513F/660W, 513F/660W/664F, 513F/660W/664Y, 513W, 513W/635F, 513W/635W, 513Y/635F/660F/664Y, 513W/635W/656W/660F, 513W/635W/660F, 513W/635W/664W, 513W/656W/664W, 513W/656Y/660W, 513W/660F, 513W/660W, 513Y/635F, 513Y/635F/664W, 513Y/635R/656F/664Y, 513Y/635W, 513Y/635W/660F, 513Y/635W/660Y, 513Y/635W/660Y/664F, 513Y/660W, 513Y/660W/664W, 513Y/660Y/664F, 513Y/664Y, 635F/656F/664Y, 635F/656Y/664W, 635F/660W/664F, 635W, 635W/656W, 635W/660F, 635W/660W, 635W/664W, 656W/660F/664Y, 656W/660W/664Y, 658P, 660F, 660F/664F, 660F/664Y, 660W/664F, 660W/664Y, 664W, 664F, and 664W, and/or any combinations thereof, wherein the amino acid positions are numbered with reference to SEQ ID NO:4. In some additional embodiments, the engineered RNA polymerases comprise at least one substitution or substitution set is selected from A397F, A397F/D513F, A397F/D513F/S635F, A397F/D513F/S635W, A397F/D513F/S635W/D660W, A397F/D513W/S635W, A397F/D513W/S635W/Q656F/P664F, A397F/D513W/P664W, A397F/D513Y, A397F/D513Y/S635W, A397F/D513Y/S635W/Q656W, A397F/D513Y/S635W/P664F, A397F/D513Y/Q656H/D660W, A397F/S635F/D660W, A397F/S635W, A397F/D660W, A397F/P664W, A397W, A397W/D513F, A397W/D513F/S635F/Q656F/D660F/P664W, A397W/D513F/S635F/D660W, A397W/D513F/S635W, A397W/D513F/D660F, A397W/D513F/D660W, A397W/D513F/D660Y/P664F, A397W/D513W, A397W/D513W/S635F, A397W/D513W/S635F/Q656W/D660F, A397W/D513W/S635W, A397W/D513W/S635W/Q656Y, A397W/D513W/S635W/D660W, A397W/D513W/S635W/D660W/P664Y, A397W/D513W/S635W/D660Y/P664Y, A397W/D513W/D660W, A397W/D513W/P664F, A397W/D513W/D660W/P664Y, A397W/D513W/P664W, A397W/D513Y/S635F, A397W/D513Y/S635W/Q656Y/D660W/P664W, A397W/D513Y/S635W, A397W/D513Y/S635W/Q656Y/P664Y, A397W/D513Y/S635W/D660F, A397W/S635F, A397W/S635F/P664F, A397W/S635W, A397W/S635W/Q656F/P664F, A397W/S635W/Q656F/P664W, A397W/S635W/Q656F/P664Y, A397W/S635W/D660W, A397W/S635W/D660Y, A397W/S635W/P664F, A397W/S635W/P664W/A850T, A397W/D660F/P664F, A397W/D660F/P664Y, A397W/D660W, A397W/E837K, A397Y, A397Y/D513F/S635W/Q656F/D660W/P664F, A397Y/D513F/S635W/P664W, A397Y/D513W/S635F/P664Y, A397Y/D513W/S635W/D660F, A397Y/D513W/Q656W/D660W, A397Y/D513Y, A397Y/D513Y/S635W, A397Y/S635F, A397Y/S635F/D660W, A397Y/S635W, A397Y/S635W/Q656F/D660Y/P664W, A397Y/S635W/D660F, A397Y/D660F/P664W, A397Y/P664F, K399E/S635F/D660W, A475V/D513W/S635W/D660Y, D513F, D513F/S635F, D513F/S635W, D513F/S635W/Q656W, D513F/S635W/P664W, D513F/D660W, D513F/D660W/P664F, D513F/D660W/P664Y, D513W, D513W/S635F, D513W/S635W, D513Y/S635F/D660F/P664Y, D513W/S635W/Q656F/D660F, D513W/S635W/D660F, D513W/S635W/P664W, D513W/Q656F/P664W, D513W/Q656Y/D660W, D513W/D660F, D513W/D660W, D513Y/S635F, D513Y/S635F/P664W, D513Y/S635R/Q656F/P664Y, D513Y/S635W, D513Y/S635W/D660F, D513Y/S635W/D660Y, D513Y/S635W/D660Y/P664F, D513Y/D660W, D513Y/D660W/P664W, D513Y/D660Y/P664F, D513Y/P664Y, S635F/Q656F/P664Y, S635F/Q656Y/P664W, S635F/D660W/P664F, S635W, S635W/Q656W, S635W/D660F, S635W/D660W, S635W/P664W, Q656W/D660F/P664F, Q656W/D660W/P664Y, L658P, D660F, D660F/P664F, D660F/P664Y, D660W/P664F, D660Y/P664W, P664F/W, and/or any combinations thereof, wherein the amino acid positions are numbered with reference to SEQ ID NO:4.

In some embodiments, the engineered RNA polymerases comprise at least one substitution or substitution set is selected from 113/137/513, 136/357/404/514, 136/357/514, 136/394/404/446, 136/401, 136/401/404, 136/404/446, 136/404/514, 136/446, 136/514, 137, 137/401, 137/401/513, 137/401/513, 137/513, 137/513/621, 137/635, 137/656, 357/394/401/404/514, 357/394/446/514, 357/514, 394/446/514, 401/404, 401/404/514, 401/513/635, 401/635, 513/635, 513/635/656, 513/660, 635/656, 635/660, and 660, and/or any combinations thereof, wherein the amino acid positions are numbered with reference to SEQ ID NO:15. In some further embodiments, the engineered RNA polymerases comprise at least one substitution or substitution set is selected from 113M/137W/513R, 136E/357I/404Y/514I, 136I/357I/514F, 136I/357K/514F, 136I/394R/404Y/446W, 136I/401V, 136I/401V/404Y, 136E/404Y/446W, 136E/404Y/514F, 136I/446W, 136E/514F, 136I/514I, 137W, 137W/401I, 137W/401S, 137W/401S/513R, 137W/401S/513W, 137W/401V, 137W/513W, 137W/513R/621R, 137W/635W, 137W/656F, 357N/394R/446W/514I, 357R/394R/401V/404Y/514L, 357R/514F, 394R/446W/514I, 401S/513R/635W, 401S/635W, 401V/404Y, 401V/404Y/514L, 513L/635W, 513L/660W, 513R/635W/656F, 635W/656F, 635W/660T, and 660S/T, and/or any combinations thereof, wherein the amino acid positions are numbered with reference to SEQ ID NO:15. In some additional embodiments, the engineered RNA polymerases comprise at least one substitution or substitution set is selected from L113M/D137W/D513R, A136E/E357I/S404Y/S514I, A136E/S404Y/M446W, A136E/S404Y/S514F, A136E/S514F, A136I/E357I/S514F, A136I/E357K/S514F, A136I/K394R/S404Y/M446W, A136I/R401V, A136I/R401V/S404Y, A136I/M446W, A136I/S514I, D137W, D137W/R401I, D137W/R401S, D137W/R401S/D513R, D137W/R401S/D513W, D137W/R401V, D137W/D513W, D137W/D513R/K621R, D137W/S635W, D137W/Q656F, E357N/K394R/M446W/S514I, E357R/K394R/R401V/S404Y/S514L, E357R/S514F, K394R/M446W/S514I, R401S/D513R/S635W, R401S/S635W, R401V/S404Y, R401V/S404Y/S514L, D513L/S635W, D513L/D660W, D513R/S635W/Q656F, S635W/Q656F, S635W/D660T, and D660S/T, and/or any combinations thereof, wherein the amino acid positions are numbered with reference to SEQ ID NO:15.

In some additional embodiments, the engineered RNA polymerases comprise polypeptide sequences at least 85%, 90%, 91%, 92%, 93%, 94%, 95%, 96%, 97%, 98%, 99% or more identical to the sequence of at least one engineered RNA polymerase variant set forth in Table 5.3, 5.4, 5.5, and/or 5.6. In some additional embodiments, the engineered RNA polymerase comprises a variant engineered polymerase provided in Table 5.3, 5.4, 5.5, and/or 5.6. In some additional embodiments, the engineered RNA polymerase is a variant engineered polymerase provided in Table 5.3, 5.4, 5.5, and/or 5.6.

In yet some additional embodiments, the engineered RNA polymerase comprises a polypeptide sequence that is at least 85%, 90%, 91%, 92%, 93%, 94%, 95%, 96%, 97%, 98%, 99% or more identical to the sequence of at least one engineered RNA polymerase variant set forth in SEQ ID NO: 4, 15, 17, 19, 21, 23, 25, 27, 29, 31, 33, 35, 37, and/or 39. In some further embodiments, the engineered RNA polymerase comprises a variant engineered polymerase set forth in SEQ ID NO: 4, 15, 17, 19, 21, 23, 25, 27, 29, 31, 33, 35, 37, or 39. In some further embodiments, the engineered RNA polymerase is a variant engineered polymerase set forth in SEQ ID NO: 4, 15, 17, 19, 21, 23, 25, 27, 29, 31, 33, 35, 37, or 39.

In some further embodiments, the engineered polymerase comprises at least one improved property compared to wild-type T7 RNA polymerase. In some further embodiments, the engineered RNA polymerase exhibits at least one improved property selected from improved selectivity for cap analog relative to GTP during transcription initiation, improved protein expression, improved stability in storage buffer, and improved stability under reaction conditions. In some additional embodiments, the engineered RNA polymerase maintains RNA yield, transcription fidelity, thermostability, protein expression, stability at −20C, or stability in reaction conditions equivalent to the wild-type T7 RNA polymerase. In yet some additional embodiments, the engineered RNA polymerase is purified. In still some further embodiments, the present invention provides compositions comprising at least one engineered RNA polymerase provided herein.

The present invention also provides polynucleotide sequences encoding at least one engineered RNA polymerase provided herein. In some embodiments, the polynucleotide sequences encoding at least one engineered RNA polymerase comprise at least 85%, 90%, 91%, 92%, 93%, 94%, 95%, 96%, 97%, 98%, 99%, or more sequence identity to the reference sequence of SEQ ID NO: 4 and/or 15, or a functional fragment thereof, wherein the engineered RNA polymerase comprises at least one substitution at one or more amino acid positions. In some further embodiments, the polynucleotide sequences encoding the engineered RNA polymerases provided herein comprise at least 85%, 90%, 91%, 92%, 93%, 94%, 95%, 96%, 97%, 98%, 99%, or more sequence identity to SEQ ID NO: 3, 15, 17, 19, 21, 23, 25, 27, 29, 31, 33, 35, 37 and/or 39, or a functional fragment thereof. In some further embodiments, the polynucleotide sequences encoding at least one engineered RNA polymerase comprise at least 85%, 90%, 91%, 92%, 93%, 94%, 95%, 96%, 97%, 98%, 99%, or more sequence identity SEQ ID NO: 3, 14, 16, 18, 20, 22, 24, 26, 28, 30, 32, 34, 36, and/or 38. In yet some additional embodiments, the polynucleotide sequences are operably linked to a control sequence. In still some further embodiments, the polynucleotide sequences are codon optimized.

The present invention also provides expression vectors comprising at least one polynucleotide sequence provided herein. The present invention further provides host cells comprising at least one expression vector provided herein. The present invention also provides methods for producing an engineered RNA polymerase in a host cell, comprising culturing the host cell provided herein, under suitable cultures conditions, such that at least one engineered RNA polymerase is produced. In some embodiments, the methods further comprise recovering at least one engineered RNA polymerase from the culture and/or host cell. In yet some additional embodiments, the methods further comprise the step of purifying at least one engineered RNA polymerase.

The present invention also provides methods for producing capped RNA transcripts, comprising providing a composition comprising: i) at least one engineered RNA polymerase provided herein, a dinucleotide cap analog, and ii) a DNA template; exposing the DNA template to the composition under conditions such that the engineered RNA polymerase produces a capped RNA transcript. In some embodiments of the methods, the dinucleotide cap analog is alpha, gamma-bis(N7-methylguanosine) triphosphate (m7G(5')ppp(5')m7G) or an anti-reverse cap analog3'-O-Me-m$^7$G(5')ppp(5')G. In some further embodiments of the methods, the dinucleotide cap analog is alpha, gamma-bis(N7-methylguanosine) triphosphate. In yet some additional embodiments of the methods, inorganic pyrophosphatase is added to the reaction.

BRIEF DESCRIPTION OF THE DRAWINGS

FIG. 1 provides the chemical structure of "m7G(5')ppp(5')m7G," also referred to as "alpha, gamma-bis(N7-methylguanosine) triphosphate", "capped-GTP," "symmetrical cap analog", or "Cap".

DESCRIPTION OF THE INVENTION

The present invention provides engineered T7 RNA polymerase variants and compositions thereof. These variants have been evolved for selective incorporation of the m7G (5')ppp(5')m7G cap analog over GTP at the initiation of in vitro transcription. The present invention also provides methods for selective capping of RNA transcripts. In addition, the present invention provides methods and compositions comprising the RNA polymerase variants provided herein.

RNA Polymerases, Transcription and Capping:

Eukaryotes have multiple types of nuclear RNA polymerases, each responsible for synthesis of a distinct subset of RNA. All are structurally and mechanistically related to each other and to bacterial RNA polymerases (RNAPs). RNAP I synthesizes a pre-rRNA 45S (35S in yeast); RNAP II synthesizes precursors of mRNAs and most snRNA and microRNAs; RNAP III synthesizes tRNAs, rRNA 5S and other small RNAs found in the nucleus and cytosol; RNAP IV synthesizes siRNA in plants; and RNAP V synthesizes RNAs involved in siRNA-directed heterochromatin formation in plants. Eukaryotic chloroplasts contain an RNAP that is very highly structurally and mechanistically similar to bacterial RNAP ("plastid-encoded polymerase"). Eukaryotic chloroplasts also contain a second, structurally and mechanistically unrelated, RNAP ("nucleus-encoded polymerase"; member of the "single-subunit RNAP" protein family). Eukaryotic mitochondria contain a structurally and mechanistically unrelated RNAP (member of the "single-subunit RNAP" protein family).

The single-subunit RNAPs typical of viruses (including phages), chloroplasts and mitochondria have been characterized and are particularly useful for in vitro transcription. Many viruses use a single-subunit DNA-dependent RNAP that is structurally and mechanistically related to the single-subunit RNAP of eukaryotic chloroplasts and mitochondria and, more distantly, to DNA polymerases and reverse transcriptases.

Transcription occurs in at least three distinct stages (i.e., initiation, elongation and termination). The initiation phase begins with the formation of an open complex and ends when the RNAP makes the transition into a stable elongation complex (See, Hsu, Biochim. Biophys. Acta, 1577:191-207 [2002]; Kinsella et al., Biochem., 21:2719-23 [1982]; Straney and Crothers, J. Mol. Biol., 193:267-78 [1987]; and Young et al., Cell, 109:417-20 [2002]). During transcription initiation, RNAPs make short abortive products from 2 to about 8 nucleotides in length, while maintaining stable interactions with the promoter (See, Carpousis and Gralla, J. Mol. Biol., 183:165-77 [1985]; Hieb et al., EMBO J., 25:3100-09 [2006]; Ikeda and Richardson, Proc. Natl. Acad. Sci. USA, 83:3614-8 [1986]; Ikeda and Richardson, J. Biol. Chem., 262:3800-8 [1987]; and Krummel and Chamberlin, Biochem., 21:2719-23 [1989]). When the length of the RNA transcript reaches more than 8 nucleotides in length, the RNAP starts to release itself from the promoter, as it transitions into an elongation complex (See, Bandwar et al., J. Mol. Biol., 360:466-83 [2006]; Esposito and Martin, J. Biol. Chem., 279:44270-6 [2004]; Guo and Sousa, J. Biol. Chem., 280:3474-82 [2005]; and Temiakov et al., Proc. Natl. Acad. Sci. USA, 97:14109-14 [2000]). The transition from the initiation complex (IC) to the elongation complex (EC) in some RNAPs (e.g., single-subunit T7 RNAP) involves large scale protein structural reorganizations (See, Cheetham et al., Cold Spring Harb. Symp. Quant. Biol., 63:263-7 [1998]; Cheetham et al., Nature, 399:80-83 [1999]; Cheetham and Steitz, Science, 286:2305-9 [1999]; Guo et al., J. Mol. Biol., 353:256-70 [2005]; Ma et al., J. Biol. Chem., 277:43206-15 [2002]; Mukherjee et al., Cell, 110: 81-91 [2002]; Tahirov et al., Nature, 420:43-50 [2002]; and Yin and Steitz, Science, 298:1387-95 [2002]).

Transcription and subsequent processing involves multiple processes and enzymes. As described above, transcription is achieved through the actions of an RNA polymerase. Although capping typically occurs while transcription is still ongoing, with interactions between capping enzymes and the RNA polymerase, the process involves separate enzymatic machinery.

The present invention provides RNA polymerases that have been modified to preferentially accept a cap (also referred to as an RNA cap, an RNA 7-methylguanosine cap or an RNA $m^7G$ cap) or cap analog (e.g., the "Anti Reverse Cap Analog" (3'-O-Me-$m^7G$(5')ppp(5')G; "ARCA"), or a methylated cap analog with one or more nucleotides at the transcription initiation site (e.g., $m^7G$(5')ppp(5')N, wherein N is any nucleotide) to begin transcription during transcription initiation. The 5' cap is an altered nucleotide on the 5' end of some eukaryotic primary transcripts such as precursor messenger RNA. The typical cap structure consists of a 7-methylguanosine linked to the first nucleotide of the transcript (the "cap-1" position) via a 5'-5' triphosphate bridge. Cap analogs can comprise, for example, one, two or more methyl (or other substitution) groups at specific positions.

Thus, the present invention provides compositions and methods for the efficient generation of capped RNA. Most eukaryotic cellular mRNA transcripts and most eukaryotic viral mRNA transcripts, as well as other form of eukaryotic RNS (e.g, small nuclear RNA [snRNA], and pre-micro RNA [pre-miRNA]) are blocked or "capped" at their 5' termini (See e.g., U.S. Pat. No. 8,846,348, incorporated herein by reference in its entirety). The cap is a guanine nucleoside that is joined via its 5'-carbon to a triphosphate group that is joined to the 5' carbon the most 5' nucleotide of the primary mRNA transcript. In most eukaryotes, the nitrogen at the 7 position of guanine in the cap nucleotide is methylated. Capping typically occurs after initiation through an enzymatic process when the mRNA is only about 30 nucleotides in length. The starting point is the unaltered 5' end of an RNA molecule, which terminates with a hydroxyl group. The capping process is initiated before the completion of transcription, as the nascent pre-mRNA is being synthesized. The capping process involves having one of the terminal phosphate groups removed by RNA triphosphatase, leaving a bisphosphate group. GTP is added to the terminal bisphosphate by mRNA guanylyltransferase, losing a pyrophosphate from the GTP substrate in the process. This results in the 5'-5' triphosphate linkage, producing G(5')ppp(5')N[pN]. The 7-nitrogen of guanine is methylated by mRNA (guanine-N7)-methyltransferase, with S-adenosyl-L-methionine being demethylated to produce S-adenosyl-L-homocysteine and $m^7G$(5')ppp(5')N[pN]. Cap-adjacent modifications can occur, normally to the first and second nucleotide positions of the nascent RNA transcript (i.e., positions cap-1 and cap-2). If the nearest cap-adjacent nucleotide is 2'-O-ribose methyl-adenosine, it can be further methylated at the $N^6$ methyl position to form $N^6$-methyladenosine.

The 5' caps of these RNA molecules play important roles in RNA stability and processing. The cap plays a very important role in mRNA metabolism and is required for processing and maturation of RNA transcripts in the nucleus, transport of mRNA from the nucleus to the cytoplasm, mRNA stability, and efficient translation of the mRNA to protein (See e.g., Lewis et. al., Eur. J. Biochem., 247:461-9 [1997].). As indicated above, the 5' cap structure is involved in the initiation of protein synthesis of eukaryotic and viral mRNAs. The 5' cap also provides resistance to 5'-exonuclease activity and its absence results in rapid degradation of mRNA (See e.g., U.S. Pat. No. 8,836,348; and Furiichi et. al., Nature, 266:235-9 [1997]). Due to the advantages provided by capping, the efficient synthesis of capped RNA transcripts provides considerable value for a variety of functions, including but not limited to in vitro and in vivo protein synthesis.

In vitro synthesis of capped RNA can be practically accomplished through one of two enzymatic routes. The Vaccinia virus capping enzyme has two subunits and three enzymatic activities that add the 7-methylguanosine cap structure to the 5' phosphate of in vitro transcribed RNA (See, Mao and Shuman, J. Biol. Chem., 269:24472-9 [1994]).

T7 RNA Polymerase:

The present invention provides single-subunit RNAPs (e.g., modified T7 RNAPs), that have been modified such that they preferentially produce capped RNA transcripts comprising a 5' cap or a 5' cap analog without an additional enzymatic capping step. The present invention provides engineered T7 RNA polymerase variants and compositions thereof. These variants have been evolved for selective incorporation of the m7G(5')ppp(5')m7G analog over GTP at the initiation of in vitro transcription. The present invention also provides methods for using the variants provided herein. The present invention further provides for the use of the compositions provided herein.

T7 RNA polymerase (E.C. 2.7.7.6), is a monomeric bacteriophage-encoded DNA directed RNA polymerase that catalyzes the formation of RNA in the 5' to 3' direction. In the process of transcription initiation, T7 RNA polymerase recognizes a specific promoter sequence (i.e., the T7 promoter). The naturally-occurring T7 RNA polymerase comprises 883 amino acids. It is highly homologous to T3 RNA polymerase and somewhat homologous to SP6 RNA polymerase. T7 is comprised of multiple domains, including the N-terminal domain, the "thumb," the "palm" and the "fingers" (See e.g., Sousa and Mukherjee, Prog. Nucl. Acid Res. Mol. Biol., 73:1-41 [2003], and U.S. Pat. No. 9,193,959). The conformation of the N-terminal domain changes between the initiation and elongation phases of the functioning enzyme. The IC and the EC structures of T7 RNAP are the beginning and the final conformations in the transition process involved in transcription. The T7 RNAP is a highly processive DNA-dependent RNAP in its EC conformation. In its IC conformation, it recognizes a specific promoter sequence and enters first into an "abortive phase" where very short transcripts are synthesized and released before proceeding to the processive transcription of long RNA chains. The structure of the IC allows for the incorporation of a cap or cap analog, e.g., ARCA, thereby allowing for the loading of a cap or cap analog at the 5' end of the mRNA transcript. Cap rates of up to 80% have been reported using the single-subunit T7 RNAP in vitro with an excess of m$^7$G(5')ppp(5')G (or simply m$^7$GpppG) over GTP (See, Nielsen and Shapiro, Nucl. Acids Res., 14:5936, [1986]). The structure of bound guanosine and m$^7$GpppG has been determined for T7 RNAP (See, Kennedy et al., J. Mol. Biol., 370:256-68 [2007]), indicating only a single additional contact for m$^7$GpppG over that for guanosine. Thus, in some embodiments, alterations to amino acids in the RNAP that are structurally close to the binding site in the initiation conformation phase are utilized to confer further specificity and efficiency for using a cap or cap analog to commence transcription (i.e., preferential incorporation of a cap or cap analog at the cap position while the RNAP is in its IC conformation). Modification of one or more residues within 15 Å, and particularly those residues within 7 Å of the nucleotide cap or cap analog creates an altered pocket where the T7 RNAP preferentially incorporates a cap or cap analog that is added to the 5' end of the nascent transcript. In some embodiments, such a modified RNAP can yield commercially feasible yields of capped RNA transcripts using amounts of cap or analog nucleotides that are equimolar or less than the amount of the corresponding nucleotide in an in vitro transcription reaction.

Although in vitro transcription is not entirely dependent on using capping enzymes to produce capped transcripts, the 80% yield typically produced by currently used methods is often times too low to be of commercial utility.

Cloning and expression of the gene encoding T7 RNA polymerase have been described (See e.g., U.S. Pat. No. 4,952,496). Due to its promoter specificity and high RNA polymerase activity, T7 has been used for various applications. It is also useful for the high-level expression of recombinant genes in *E. coli* (See, Studier and Moffat, J. Mol. Biol., 18:113-130 [1986]). T7 is also used in various nucleic acid amplification methods, including those used in diagnostic methods. As stability and thermostability are often important considerations in the development of components of diagnostic methods, work has been reported on improving the thermostability and stability of T7 (See e.g., U.S. Pat. Nos. 9,193,959, 8,551,752, and 7,507,567, etc.). Nonetheless, there remains a need in the art for variant T7 enzymes that exhibit improved properties, as compared to the naturally-occurring enzyme.

An alternative method for in vitro synthesis of capped RNA discussed above, is to incorporate a cap structure during in vitro transcription with the use of a cap analog. These 7-methylguanosine-containing dinucleotides contain a 5'-5' triphosphate linkage, and are incorporated at the initiation site of transcription, resulting in a 7-methylguanosine capped RNA product. T7 RNA polymerase natively initiates transcription with incorporation of a guanosine opposite a cytosine residue on the template. To achieve a high efficiency of capping, the guanosine cap analog must be present in the in vitro transcription reaction at a high concentration relative to GTP, with which it competes for incorporation at the first position in the mRNA. One useful feature of co-transcriptional in vitro capping is that because the cap incorporation in achieved during initiation, the final sequence or secondary structure of the full-length mRNA does not influence the extent of capping. In addition, the process requires the use of only one enzyme (RNA polymerase), in a single-step reaction. The use of a chemically synthesized cap analog also increases the flexibility to use alternative nucleotide cap structures that are not well recognized for methylation by the Vaccinia capping enzyme. However, the cap analog is expensive relative to nucleotides and other reaction components, and must be present at a high concentration in the reaction. The present invention provides T7 RNA polymerase variants that are selective for the incorporating of cap analogs over GTP at the initiation of transcription to enable efficient capping using a reduced concentration of cap analog, providing a more cost-effective and scalable production process for capped RNA.

In some embodiments of the invention, inorganic pyrophosphatase is present during the in vitro transcription reaction to degrade pyrophosphate, a product inhibitor of transcription by RNA polymerase, into orthophosphate.

Thus, the present invention provides modified RNAPs that incorporate a cap or cap analog proficiently to allow for a yield of greater than about 80% capped mRNA relative to uncapped mRNA. The modified RNAP, for example, can produce mRNA of greater than 85% or about 85%, greater than 90% or about 90%, greater than 95% or about 95%, greater than 99% or about 99% capped mRNA relative to uncapped mRNA.

In some embodiments, the modified RNAP is derived from the sequence and structure of a single-subunit RNAP (i.e., the T7 RNAP). Modified T7 RNAPs with increased efficiency to incorporate "capped-G" ($m^7GpppG$), $m^7GpppN$ and/or ARCA are provided by the present invention. The improved T7 RNAP variants facilitate more efficient and cost-effective manufacture of capped RNAs for pharmaceutical and medical use. These modified RNAPs also provide improved capped RNA yields without compromising or only minimally altering the efficiency of transcription relative to the unmodified RNAP.

Abbreviations and Definitions

Unless defined otherwise, all technical and scientific terms used herein generally have the same meaning as commonly understood by one of ordinary skill in the art to which this invention pertains. Generally, the nomenclature used herein and the laboratory procedures of cell culture, molecular genetics, microbiology, biochemistry, organic chemistry, analytical chemistry and nucleic acid chemistry described below are those well-known and commonly employed in the art. Such techniques are well-known and described in numerous texts and reference works well known to those of skill in the art. Standard techniques, or modifications thereof, are used for chemical syntheses and chemical analyses. All patents, patent applications, articles and publications mentioned herein, both supra and infra, are hereby expressly incorporated herein by reference.

Although any suitable methods and materials similar or equivalent to those described herein find use in the practice of the present invention, some methods and materials are described herein. It is to be understood that this invention is not limited to the particular methodology, protocols, and reagents described, as these may vary, depending upon the context they are used by those of skill in the art. Accordingly, the terms defined immediately below are more fully described by reference to the application as a whole. All patents, patent applications, articles and publications mentioned herein, both supra and infra, are hereby expressly incorporated herein by reference.

Also, as used herein, the singular "a", "an," and "the" include the plural references, unless the context clearly indicates otherwise.

Numeric ranges are inclusive of the numbers defining the range. Thus, every numerical range disclosed herein is intended to encompass every narrower numerical range that falls within such broader numerical range, as if such narrower numerical ranges were all expressly written herein. It is also intended that every maximum (or minimum) numerical limitation disclosed herein includes every lower (or higher) numerical limitation, as if such lower (or higher) numerical limitations were expressly written herein.

The term "about" means an acceptable error for a particular value. In some instances "about" means within 0.05%, 0.5%, 1.0%, or 2.0%, of a given value range. In some instances, "about" means within 1, 2, 3, or 4 standard deviations of a given value.

Furthermore, the headings provided herein are not limitations of the various aspects or embodiments of the invention which can be had by reference to the application as a whole.

Accordingly, the terms defined immediately below are more fully defined by reference to the application as a whole. Nonetheless, in order to facilitate understanding of the invention, a number of terms are defined below.

Unless otherwise indicated, nucleic acids are written left to right in 5' to 3' orientation; amino acid sequences are written left to right in amino to carboxy orientation, respectively.

As used herein, the term "comprising" and its cognates are used in their inclusive sense (i.e., equivalent to the term "including" and its corresponding cognates).

"EC" number refers to the Enzyme Nomenclature of the Nomenclature Committee of the International Union of Biochemistry and Molecular Biology (NC-IUBMB). The IUBMB biochemical classification is a numerical classification system for enzymes based on the chemical reactions they catalyze.

"ATCC" refers to the American Type Culture Collection whose biorepository collection includes genes and strains.

"NCBI" refers to National Center for Biological Information and the sequence databases provided therein.

As used herein, "T7 RNA polymerase" refers to a monomeric T7 bacteriophage-encoded DNA directed RNA polymerase that catalyzes the formation of RNA in the 5' to 3' direction.

As used herein, the term "cap" refers to the guanine nucleoside that is joined via its 5' carbon to a triphosphate group that is, in turn, joined to the 5' carbon of the most 5' nucleotide of an mRNA transcript. In some embodiments, the nitrogen at the 7 position of guanine in the cap is methylated.

As used herein, the terms "capped RNA," "5' capped RNA," and "capped mRNA" refer to RNA and mRNA, respectively that comprise the cap.

As used herein, "polynucleotide" and "nucleic acid' refer to two or more nucleosides that are covalently linked together. The polynucleotide may be wholly comprised of ribonucleotides (i.e., RNA), wholly comprised of 2' deoxyribonucleotides (i.e., DNA), or comprised of mixtures of ribo- and 2' deoxyribonucleotides. While the nucleosides will typically be linked together via standard phosphodiester linkages, the polynucleotides may include one or more non-standard linkages. The polynucleotide may be single-stranded or double-stranded, or may include both single-stranded regions and double-stranded regions. Moreover, while a polynucleotide will typically be composed of the naturally occurring encoding nucleobases (i.e., adenine, guanine, uracil, thymine and cytosine), it may include one or more modified and/or synthetic nucleobases, such as, for example, inosine, xanthine, hypoxanthine, etc. In some embodiments, such modified or synthetic nucleobases are nucleobases encoding amino acid sequences.

"Protein," "polypeptide," and "peptide" are used interchangeably herein to denote a polymer of at least two amino acids covalently linked by an amide bond, regardless of length or post-translational modification (e.g., glycosylation or phosphorylation).

"Amino acids" are referred to herein by either their commonly known three-letter symbols or by the one-letter symbols recommended by IUPAC-IUB Biochemical Nomenclature Commission. Nucleotides, likewise, may be referred to by their commonly accepted single letter codes. The abbreviations used for the genetically encoded amino acids are conventional and are as follows: alanine (Ala or A), arginine (Are or R), asparagine (Asn or N), aspartate (Asp or D), cysteine (Cys or C), glutamate (Glu or E), glutamine (Gln or Q), histidine (His or H), isoleucine (Ile or I), leucine (Leu or L), lysine (Lys or K), methionine (Met or M), phenylalanine (Phe or F), proline (Pro or P), serine (Ser or S), threonine (Thr or T), tryptophan (Trp or W), tyrosine (Tyr or Y), and valine (Val or V).

When the three-letter abbreviations are used, unless specifically preceded by an "L" or a "D" or clear from the context in which the abbreviation is used, the amino acid may be in either the L- or D-configuration about α-carbon ($C_\alpha$). For example, whereas "Ala" designates alanine without specifying the configuration about the α-carbon, "D-Ala" and "L-Ala" designate D-alanine and L-alanine, respectively. When the one-letter abbreviations are used, upper case letters designate amino acids in the L-configuration about the α-carbon and lower case letters designate amino acids in the D-configuration about the α-carbon. For example, "A" designates L-alanine and "a" designates D-alanine. When polypeptide sequences are presented as a string of one-letter or three-letter abbreviations (or mixtures thereof), the sequences are presented in the amino (N) to carboxy (C) direction in accordance with common convention.

The abbreviations used for the genetically encoding nucleosides are conventional and are as follows: adenosine (A); guanosine (G); cytidine (C); thymidine (T); and uridine (U). Unless specifically delineated, the abbreviated nucleosides may be either ribonucleosides or 2'-deoxyribonucleosides. The nucleosides may be specified as being either ribonucleosides or 2'-deoxyribonucleosides on an individual basis or on an aggregate basis. When nucleic acid sequences are presented as a string of one-letter abbreviations, the sequences are presented in the 5' to 3' direction in accordance with common convention, and the phosphates are not indicated.

The term "engineered," "recombinant," "non-naturally occurring," and "variant," when used with reference to a cell, a polynucleotide or a polypeptide refers to a material or a material corresponding to the natural or native form of the material that has been modified in a manner that would not otherwise exist in nature or is identical thereto but produced or derived from synthetic materials and/or by manipulation using recombinant techniques.

As used herein, "wild-type" and "naturally-occurring" refer to the form found in nature. For example a wild-type polypeptide or polynucleotide sequence is a sequence present in an organism that can be isolated from a source in nature and which has not been intentionally modified by human manipulation.

"Coding sequence" refers to that part of a nucleic acid (e.g., a gene) that encodes an amino acid sequence of a protein.

The term "percent (%) sequence identity" is used herein to refer to comparisons among polynucleotides and polypeptides, and are determined by comparing two optimally aligned sequences over a comparison window, wherein the portion of the polynucleotide or polypeptide sequence in the comparison window may comprise additions or deletions (i.e., gaps) as compared to the reference sequence for optimal alignment of the two sequences. The percentage may be calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Alternatively, the percentage may be calculated by determining the number of positions at which either the identical nucleic acid base or amino acid residue occurs in both sequences or a nucleic acid base or amino acid residue is aligned with a gap to yield the number of matched positions, dividing the number of matched positions by the total number of positions in the window of comparison and multiplying the result by 100 to yield the percentage of sequence identity. Those of skill in the art appreciate that there are many established algorithms available to align two sequences. Optimal alignment of sequences for comparison can be conducted, e.g., by the local homology algorithm of Smith and Waterman (Smith and Waterman, Adv. Appl. Math., 2:482 [1981]), by the homology alignment algorithm of Needleman and Wunsch (Needleman and Wunsch, J. Mol. Biol., 48:443 [1970], by the search for similarity method of Pearson and Lipman (Pearson and Lipman, Proc. Natl. Acad. Sci. USA 85:2444 [1988]), by computerized implementations of these algorithms (e.g., GAP, BESTFIT, FASTA, and TFASTA in the GCG Wisconsin Software Package), or by visual inspection, as known in the art. Examples of algorithms that are suitable for determining percent sequence identity and sequence similarity include, but are not limited to the BLAST and BLAST 2.0 algorithms, which are described by Altschul et al. (See, Altschul et al., J. Mol. Biol., 215: 403-410 [1990]; and Altschul et al., Nucleic Acids Res., 25:3389-3402 [1977], respectively). Software for performing BLAST analyses is publicly available through the National Center for Biotechnology Information website. This algorithm involves first identifying high scoring sequence pairs (HSPs) by identifying short words of length W in the query sequence, which either match or satisfy some positive-valued threshold score T when aligned with a word of the same length in a database sequence. T is referred to as, the neighborhood word score threshold (See, Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (See, Henikoff and Henikoff, Proc. Natl. Acad. Sci. USA 89:10915 [1989]). Exemplary determination of sequence alignment and % sequence identity can employ the BESTFIT or GAP programs in the GCG Wisconsin Software package (Accelrys, Madison Wis.), using default parameters provided.

"Reference sequence" refers to a defined sequence used as a basis for a sequence comparison. A reference sequence may be a subset of a larger sequence, for example, a segment of a full-length gene or polypeptide sequence. Generally, a reference sequence is at least 20 nucleotide or amino acid residues in length, at least 25 residues in length, at least 50 residues in length, at least 100 residues in length or the full length of the nucleic acid or polypeptide. Since two polynucleotides or polypeptides may each (1) comprise a sequence (i.e., a portion of the complete sequence) that is similar between the two sequences, and (2) may further comprise a sequence that is divergent between the two sequences, sequence comparisons between two (or more) polynucleotides or polypeptide are typically performed by comparing sequences of the two polynucleotides or polypeptides over a "comparison window" to identify and compare local regions of sequence similarity. In some embodiments, a "reference sequence" can be based on a primary amino acid sequence, where the reference sequence is a sequence that can have one or more changes in the primary sequence.

"Comparison window" refers to a conceptual segment of at least about 20 contiguous nucleotide positions or amino acids residues wherein a sequence may be compared to a reference sequence of at least 20 contiguous nucleotides or amino acids and wherein the portion of the sequence in the comparison window may comprise additions or deletions (i.e., gaps) of 20 percent or less as compared to the reference sequence (which does not comprise additions or deletions) for optimal alignment of the two sequences. The comparison window can be longer than 20 contiguous residues, and includes, optionally 30, 40, 50, 100, or longer windows.

"Corresponding to", "reference to" or "relative to" when used in the context of the numbering of a given amino acid or polynucleotide sequence refers to the numbering of the residues of a specified reference sequence when the given amino acid or polynucleotide sequence is compared to the reference sequence. In other words, the residue number or residue position of a given polymer is designated with respect to the reference sequence rather than by the actual numerical position of the residue within the given amino acid or polynucleotide sequence. For example, a given amino acid sequence, such as that of an engineered T7 RNA polymerase, can be aligned to a reference sequence by introducing gaps to optimize residue matches between the two sequences. In these cases, although the gaps are present, the numbering of the residue in the given amino acid or polynucleotide sequence is made with respect to the reference sequence to which it has been aligned.

"Amino acid difference" or "residue difference" refers to a difference in the amino acid residue at a position of a polypeptide sequence relative to the amino acid residue at a corresponding position in a reference sequence. The positions of amino acid differences generally are referred to herein as "Xn," where n refers to the corresponding position in the reference sequence upon which the residue difference is based. For example, a "residue difference at position X93 as compared to SEQ ID NO:2" refers to a difference of the amino acid residue at the polypeptide position corresponding to position 93 of SEQ ID NO:2. Thus, if the reference polypeptide of SEQ ID NO:2 has a serine at position 93, then a "residue difference at position X93 as compared to SEQ ID NO:2" an amino acid substitution of any residue other than serine at the position of the polypeptide corresponding to position 93 of SEQ ID NO:2. In most instances herein, the specific amino acid residue difference at a position is indicated as "XnY" where "Xn" specified the corresponding position as described above, and "Y" is the single letter identifier of the amino acid found in the engineered polypeptide (i.e., the different residue than in the reference polypeptide). In some instances (e.g., in the Tables provided in the Examples herein), the present disclosure also provides specific amino acid differences denoted by the conventional notation "AnB", where A is the single letter identifier of the residue in the reference sequence, "n" is the number of the residue position in the reference sequence, and B is the single letter identifier of the residue substitution in the sequence of the engineered polypeptide. In some instances, a polypeptide of the present disclosure can include one or more amino acid residue differences relative to a reference sequence, which is indicated by a list of the specified positions where residue differences are present relative to the reference sequence. In some embodiments, where more than one amino acid can be used in a specific residue position of a polypeptide, the various amino acid residues that can be used are separated by a "/" (e.g., X10H/X10P or X10H/P). In some embodiments, the enzyme variants comprise more than one substitution. These substitutions are separated by a slash for ease in reading (e.g., C14A/K122A). The present application includes engineered polypeptide sequences comprising one or more amino acid differences that include either/or both conservative and non-conservative amino acid substitutions.

"Conservative amino acid substitution" refers to a substitution of a residue with a different residue having a similar side chain, and thus typically involves substitution of the amino acid in the polypeptide with amino acids within the same or similar defined class of amino acids. By way of example and not limitation, an amino acid with an aliphatic side chain may be substituted with another aliphatic amino acid (e.g., alanine, valine, leucine, and isoleucine); an amino acid with hydroxyl side chain is substituted with another amino acid with a hydroxyl side chain (e.g., serine and threonine); an amino acids having aromatic side chains is substituted with another amino acid having an aromatic side chain (e.g., phenylalanine, tyrosine, tryptophan, and histidine); an amino acid with a basic side chain is substituted with another amino acid with a basis side chain (e.g., lysine and arginine); an amino acid with an acidic side chain is substituted with another amino acid with an acidic side chain (e.g., aspartic acid or glutamic acid); and/or a hydrophobic or hydrophilic amino acid is replaced with another hydrophobic or hydrophilic amino acid, respectively.

"Non-conservative substitution" refers to substitution of an amino acid in the polypeptide with an amino acid with significantly differing side chain properties. Non-conservative substitutions may use amino acids between, rather than within, the defined groups and affects (a) the structure of the peptide backbone in the area of the substitution (e.g., proline for glycine) (b) the charge or hydrophobicity, or (c) the bulk of the side chain. By way of example and not limitation, an exemplary non-conservative substitution can be an acidic amino acid substituted with a basic or aliphatic amino acid; an aromatic amino acid substituted with a small amino acid; and a hydrophilic amino acid substituted with a hydrophobic amino acid.

"Deletion" refers to modification to the polypeptide by removal of one or more amino acids from the reference polypeptide. Deletions can comprise removal of 1 or more amino acids, 2 or more amino acids, 5 or more amino acids, 10 or more amino acids, 15 or more amino acids, or 20 or more amino acids, up to 10% of the total number of amino acids, or up to 20% of the total number of amino acids making up the reference enzyme while retaining enzymatic activity and/or retaining the improved properties of an engineered enzyme. Deletions can be directed to the internal portions and/or terminal portions of the polypeptide. In various embodiments, the deletion can comprise a continuous segment or can be discontinuous.

"Insertion" refers to modification to the polypeptide by addition of one or more amino acids from the reference polypeptide. Insertions can be in the internal portions of the polypeptide, or to the carboxy or amino terminus. Insertions as used herein include fusion proteins as is known in the art. The insertion can be a contiguous segment of amino acids or separated by one or more of the amino acids in the naturally occurring polypeptide.

"Isolated polypeptide" refers to a polypeptide which is substantially separated from other contaminants that naturally accompany it (e.g., protein, lipids, and polynucleotides). The term embraces polypeptides which have been removed or purified from their naturally-occurring environment or expression system (e.g., host cell or in vitro synthesis). The recombinant T7 RNA polymerase polypeptides may be present within a cell, present in the cellular medium, or prepared in various forms, such as lysates or isolated preparations. As such, in some embodiments, the recombinant T7 RNA polymerase polypeptides can be an isolated polypeptide.

"Substantially pure polypeptide" refers to a composition in which the polypeptide species is the predominant species present (i.e., on a molar or weight basis it is more abundant than any other individual macromolecular species in the composition), and is generally a substantially purified composition when the object species comprises at least about 50 percent of the macromolecular species present by mole or % weight. Generally, a substantially pure T7 RNA polymerase composition comprises about 60% or more, about 70% or more, about 80% or more, about 90% or more, about 95% or more, and about 98% or more of all macromolecular species by mole or % weight present in the composition. In some embodiments, the object species is purified to essential homogeneity (i.e., contaminant species cannot be detected in the composition by conventional detection methods) wherein the composition consists essentially of a single macromolecular species. Solvent species, small molecules (<500 Daltons), and elemental ion species are not considered macromolecular species. In some embodiments, the isolated recombinant T7 RNA polymerase polypeptides are substantially pure polypeptide compositions.

"Improved enzyme property" of a T7 RNA polymerase refers to an engineered T7 RNA polymerase polypeptide that exhibits an improvement in any enzyme property as compared to a reference T7 RNA polymerase polypeptide and/or a wild-type T7 RNA polymerase polypeptide and/or another engineered T7 RNA polymerase polypeptide. Improved properties include, but are not limited to such properties as increased selectivity for cap analog over GTP, increased fidelity of replication, increased RNA yield, increased protein expression, increased thermoactivity, increased thermostability, increased pH activity, increased stability, increased enzymatic activity, increased substrate specificity or affinity, increased specific activity, increased resistance to substrate or end-product inhibition (including pyrophosphate), increased chemical stability, improved solvent stability, increased tolerance to acidic or basic pH, increased tolerance to proteolytic activity (i.e., reduced sensitivity to proteolysis), reduced aggregation, increased solubility, and altered temperature profile.

"Increased enzymatic activity" or "enhanced catalytic activity" refers to an improved property of the engineered T7 RNA polymerase, which can be represented by an increase in specific activity (e.g., product produced/time/weight protein) or an increase in percent conversion of the substrate to the product (e.g., percent conversion of starting amount of substrate to product in a specified time period using a specified amount of variant T7 RNA polymerase as compared to the reference T7 RNA polymerase. Exemplary methods to determine enzyme activity are provided in the Examples. Any property relating to enzyme activity may be affected.

"Hybridization stringency" relates to hybridization conditions, such as washing conditions, in the hybridization of nucleic acids. Generally, hybridization reactions are performed under conditions of lower stringency, followed by washes of varying but higher stringency. The term "moderately stringent hybridization" refers to conditions that permit target-DNA to bind a complementary nucleic acid that has about 60% identity, preferably about 75% identity, about 85% identity to the target DNA, with greater than about 90% identity to target-polynucleotide. Exemplary moderately stringent conditions are conditions equivalent to hybridization in 50% formamide, 5× Denhart's solution, 5×SSPE, 0.2% SDS at 42° C., followed by washing in 0.2×SSPE, 0.2% SDS, at 42° C. "High stringency hybridization" refers generally to conditions that are about 10° C. or less from the thermal melting temperature $T_m$, as determined under the solution condition for a defined polynucleotide sequence. In some embodiments, a high stringency condition refers to conditions that permit hybridization of only those nucleic acid sequences that form stable hybrids in 0.018M NaCl at 65° C. (i.e., if a hybrid is not stable in 0.018M NaCl at 65° C., it will not be stable under high stringency conditions, as contemplated herein). High stringency conditions can be provided, for example, by hybridization in conditions equivalent to 50% formamide, 5× Denhart's solution, 5×SSPE, 0.2% SDS at 42° C., followed by washing in 0.1×SSPE, and 0.1% SDS at 65° C. Another high stringency condition is hybridizing in conditions equivalent to hybridizing in 5×SSC containing 0.1% (w:v) SDS at 65° C. and washing in 0.1×SSC containing 0.1% SDS at 65° C. Other high stringency hybridization conditions, as well as moderately stringent conditions, are described in the references cited above.

"Codon optimized" refers to changes in the codons of the polynucleotide encoding a protein to those preferentially used in a particular organism such that the encoded protein is more efficiently expressed in the organism of interest. Although the genetic code is degenerate in that most amino acids are represented by several codons, called "synonyms" or "synonymous" codons, it is well known that codon usage by particular organisms is nonrandom and biased towards particular codon triplets. This codon usage bias may be higher in reference to a given gene, genes of common function or ancestral origin, highly expressed proteins versus low copy number proteins, and the aggregate protein coding regions of an organism's genome. In some embodiments, the polynucleotides encoding the T7 RNA polymerase enzymes may be codon optimized for optimal production from the host organism selected for expression.

"Control sequence" refers herein to include all components, which are necessary or advantageous for the expression of a polynucleotide and/or polypeptide of the present application. Each control sequence may be native or foreign to the nucleic acid sequence encoding the polypeptide. Such control sequences include, but are not limited to, a leader, polyadenylation sequence, propeptide sequence, promoter sequence, signal peptide sequence, initiation sequence and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a polypeptide.

"Operably linked" is defined herein as a configuration in which a control sequence is appropriately placed (i.e., in a functional relationship) at a position relative to a polynucleotide of interest such that the control sequence directs or regulates the expression of the polynucleotide and/or polypeptide of interest.

"Promoter sequence" refers to a nucleic acid sequence that is recognized by a host cell for expression of a polynucleotide of interest, such as a coding sequence. The promoter sequence contains transcriptional control sequences, which mediate the expression of a polynucleotide of interest. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

"Suitable reaction conditions" refers to those conditions in the enzymatic conversion reaction solution (e.g., ranges of enzyme loading, substrate loading, temperature, pH, buffers, co-solvents, etc.) under which a T7 RNA polymerase polypeptide of the present application is capable of converting a substrate to the desired product compound.

"Substrate" in the context of an enzymatic conversion reaction process refers to the compound or molecule acted on by the T7 RNA polymerase polypeptide.

"Product" in the context of an enzymatic conversion process refers to the compound or molecule resulting from the action of the T7 RNA polymerase polypeptide on a substrate.

As used herein the term "culturing" refers to the growing of a population of microbial cells under any suitable conditions (e.g., using a liquid, gel or solid medium).

Recombinant polypeptides can be produced using any suitable methods known the art. Genes encoding the wild-type polypeptide of interest can be cloned in vectors, such as plasmids, and expressed in desired hosts, such as *E. coli, S. cerevisiae*, etc. Variants of recombinant polypeptides can be generated by various methods known in the art. Indeed, there is a wide variety of different mutagenesis techniques well known to those skilled in the art. In addition, mutagenesis kits are also available from many commercial molecular biology suppliers. Methods are available to make specific substitutions at defined amino acids (site-directed), specific or random mutations in a localized region of the gene (regio-specific), or random mutagenesis over the entire gene (e.g., saturation mutagenesis). Numerous suitable methods are known to those in the art to generate enzyme variants, including but not limited to site-directed mutagenesis of single-stranded DNA or double-stranded DNA using PCR, cassette mutagenesis, gene synthesis, error-prone PCR, shuffling, and chemical saturation mutagenesis, or any other suitable method known in the art. Non-limiting examples of methods used for DNA and protein engineering are provided in the following patents: U.S. Pat. Nos. 6,117,679; 6,420,175; 6,376,246; 6,586,182; 7,747,391; 7,747,393; 7,783,428; and 8,383,346. After the variants are produced, they can be screened for any desired property (e.g., high or increased activity, or low or reduced activity, increased thermal activity, increased thermal stability, and/or acidic pH stability, etc.).

In some embodiments, "recombinant T7 RNA polymerase polypeptides" (also referred to herein as "engineered T7 RNA polymerase polypeptides," "variant T7 RNA polymerase enzymes," and "T7 RNA polymerase variants") find use.

As used herein, a "vector" is a DNA construct for introducing a DNA sequence into a cell. In some embodiments, the vector is an expression vector that is operably linked to a suitable control sequence capable of effecting the expression in a suitable host of the polypeptide encoded in the DNA sequence. In some embodiments, an "expression vector" has a promoter sequence operably linked to the DNA sequence (e.g., transgene) to drive expression in a host cell, and in some embodiments, also comprises a transcription terminator sequence.

As used herein, the term "expression" includes any step involved in the production of the polypeptide including, but not limited to, transcription, post-transcriptional modification, translation, and post-translational modification. In some embodiments, the term also encompasses secretion of the polypeptide from a cell.

As used herein, the term "produces" refers to the production of proteins and/or other compounds by cells. It is intended that the term encompass any step involved in the production of polypeptides including, but not limited to, transcription, post-transcriptional modification, translation, and post-translational modification. In some embodiments, the term also encompasses secretion of the polypeptide from a cell.

As used herein, an amino acid or nucleotide sequence (e.g., a promoter sequence, signal peptide, terminator sequence, etc.) is "heterologous" to another sequence with which it is operably linked if the two sequences are not associated in nature.

As used herein, the terms "host cell" and "host strain" refer to suitable hosts for expression vectors comprising DNA provided herein (e.g., the polynucleotides encoding the T7 RNA polymerase variants). In some embodiments, the host cells are prokaryotic or eukaryotic cells that have been transformed or transfected with vectors constructed using recombinant DNA techniques as known in the art.

The term "analogue" when used in reference to a polypeptide, means a polypeptide having more than 70% sequence identity but less than 100% sequence identity (e.g., more than 75%, 78%, 80%, 83%, 85%, 88%, 90%, 91%, 92%, 93%, 94%, 95%, 96%, 97%, 98%, 99% sequence identity) with a reference polypeptide. In some embodiments, analogues means polypeptides that contain one or more non-naturally occurring amino acid residues including, but not limited, to homoarginine, ornithine and norvaline, as well as naturally occurring amino acids. In some embodiments, analogues also include one or more D-amino acid residues and non-peptide linkages between two or more amino acid residues.

The term "effective amount" means an amount sufficient to produce the desired result. One of general skill in the art may determine what the effective amount by using routine experimentation.

The terms "isolated" and "purified" are used to refer to a molecule (e.g., an isolated nucleic acid, polypeptide, etc.) or other component that is removed from at least one other component with which it is naturally associated. The term "purified" does not require absolute purity, rather it is intended as a relative definition.

As used herein, "composition" and "formulation" encompass products comprising at least one engineered T7 RNA polymerase of the present invention, intended for any suitable use (e.g., research, diagnostics, etc.).

The term "transcription" is used to refer to the process whereby a portion of a DNA template is copied into RNA by the action of an RNA polymerase enzyme.

The term "DNA template" is used to refer to a double or single-stranded DNA molecule including a promoter sequence and a sequence coding for the RNA product of transcription.

The term "promoter" is used to refer to a DNA sequence that is recognized by RNA polymerase as the start site of transcription. The promoter recruits RNA polymerase, and in the case of T7RNA polymerase, determines the start site of transcription.

The term "RNA polymerase" is used to refer to a DNA-directed RNA polymerase, which copies a DNA template into an RNA polynucleotide, by incorporating nucleotide triphosphates stepwise into the growing RNA polymer The terms "messenger RNA" and "mRNA" are used to refer to RNA molecules that code for a protein. This protein is decoded through the action of translation.

The terms "7-methylguanosine cap," "7meG," "five-prime cap," and "5' cap" are used in reference to a specific modified nucleotide structure present at the 5' end of eukaryotic mRNAs. The 7-methylguanosine cap structure is attached through a 5' to 5' triphosphate linkage to the first nucleotide in the mRNA. In vivo, this cap structure is added to the 5' end of a nascent mRNA through the successive activities of multiple enzymes. In vitro, the cap can be incorporated directly at the initiation of transcription by an RNA polymerase by use of a cap analog.

The term "Cap analog" refers to a dinucleotide containing a 5'-5' di-, tri-, or tetra-phosphate linkage. One end of the dinucleotide terminates in a either a guanosine or substituted guanosine residue; it is this end from which RNA polymerase will initiate transcription by extending from the 3' hydroxyl. The other end of the dinucleotide is a guanosine that mimics the eukaryotic cap structure, and will typically have 7-methyl-, 7-benzyl-, or 7-ethyl-substitutions and/or 7-aminomethyl or 7-aminoethyl substitutions. In some cases, this nucleotide also is methoxy substituted at the 3' hydroxyl group to prevent initiation of transcription from the cap end of the molecule.

The terms "ARCA" and "anti-reverse cap analog" refer to chemically modified forms of cap analogs, designed to maximize the efficient of in vitro translation by ensuring that the cap analog is properly incorporated into the transcript in the correct orientation. These analogs find use in enhancing translation. In some embodiments, the ARCAs known in the art find use (e.g., Peng et al., Org. Lett., 4:161-164 [2002]).

The term "riboswitch" is used to refer to an autocatalytic RNA enzyme that cleaves itself or another RNA in the presence of a ligand.

The term "fidelity" is used to refer to the accuracy of an RNA polymerase in transcribing, or copying, a DNA template into an RNA polynucleotide. Inaccurate transcription can result in single-nucleotide polymorphisms (SNPs) or Indels.

The terms "single-nucleotide polymorphism" or "SNP" refer to a change in the nucleotide present at a single position in polynucleotide. In the context of transcription, SNPs can result from misincorporation of a non-complementary ribonucleotide (A, C, G, or U) by RNA polymerase at a position on the DNA template.

The term "Indel" is used to refer to an insertion or deletion of one or more polynucleotides. In the context of transcription by RNA polymerase, indel errors can result from the addition of a one or more extra ribonucleotides or failure to incorporate one or more nucleotides at a position on the DNA template.

The term "selectivity" is used to refer to the trait of an enzyme to have higher activity against one substrate as compared to another substrate during a catalyzed reaction. In the context of co-transcriptional capping, the RNA polymerase may have high or low selectivity for a cap analog over GTP.

The term "inorganic pyrophosphatase" is used to refer to an enzyme that degrades inorganic pyrophosphate to orthophosphate.

Engineered T7 RNA Polymerase Activity:

In some embodiments, the engineered T7 RNA polymerase provided herein, that exhibits an improved property has at least about 85%, at least about 88%, at least about 90%, at least about 91%, at least about 92%, at least about 93%, at least about 94%, at least about 95%, at least about 96%, at least about 97%, at least about 98%, at least about 99%, or at about 100% amino acid sequence identity with SEQ ID NO: 4 and/or 15, and an amino acid residue difference as compared to SEQ ID NO: 4 and/or 15, at one or more amino acid positions (such as at 1, 2, 3, 4, 5, 6, 7, 8, 9, 10, 11, 12, 14, 15, 20 or more amino acid positions compared to SEQ ID NO: 4 and/or 15, or a sequence having at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO: 4 and/or 15). In some embodiment the residue difference as compared to SEQ ID NO:4, at one or more positions will include at least 1, 2, 3, 4, 5, 6, 7, 8, 9, 10 or more conservative amino acid substitutions. In some embodiments, the engineered T7 RNA polymerase polypeptide is a polypeptide listed in Table 5.3, 5.5, and/or 5.6. In some embodiments, the engineered T7 RNA polymerase polypeptide is selected from SEQ ID NOS: 4, 15, 17, 19, 21, 23, 25, 27, 29, 32, 33, 35, 37, and/or 39. In some embodiment the residue difference as compared to SEQ ID NO: 15, at one or more positions will include at least 1, 2, 3, 4, 5, 6, 7, 8, 9, 10 or more conservative amino acid substitutions. In some embodiments, the engineered T7 RNA polymerase polypeptide is a polypeptide listed in Table 5.4. In some embodiments, the engineered T7 RNA polymerase polypeptide is selected from SEQ ID NOS: 4, 15, 17, 19, 21, 23, 25, 27, 29, 32, 33, 35, 37, and/or 39.

In some embodiments, the engineered T7 RNA polymerase polypeptide comprises a functional fragment of an engineered T7 RNA polymerase polypeptide encompassed by the invention. Functional fragments have at least 80%, 81%, 82%, 83%, 84%, 85%, 86%, 87%, 88%, 89%, 90%, 91%, 92%, 93%, 94%, 95%, 96%, 97%, 98%, or 99% of the activity of the engineered T7 RNA polymerase polypeptide from which is was derived (i.e., the parent engineered T7 RNA polymerase). A functional fragment comprises at least 80%, 81%, 82%, 83%, 84%, 85%, 86%, 87%, 88%, 89%, 90%, 91%, 92%, 93%, 94%, 95%, 96%, 97%, 98% and even 99% of the parent sequence of the engineered T7 RNA polymerase. In some embodiments the functional fragment is truncated by less than 5, less than 10, less than 15, less than 10, less than 25, less than 30, less than 35, less than 40, less than 45, and less than 50 amino acids.

Polynucleotides Encoding Engineered Polypeptides, Expression Vectors and Host Cells:

The present invention provides polynucleotides encoding the engineered T7 RNA polymerase polypeptides described herein. In some embodiments, the polynucleotides are operatively linked to one or more heterologous regulatory sequences that control gene expression to create a recombinant polynucleotide capable of expressing the polypeptide. Expression constructs containing a heterologous polynucleotide encoding the engineered T7 RNA polymerase polypeptides can be introduced into appropriate host cells to express the corresponding T7 RNA polymerase polypeptide.

As will be apparent to the skilled artisan, availability of a protein sequence and the knowledge of the codons corresponding to the various amino acids provide a description of all the polynucleotides capable of encoding the subject polypeptides. The degeneracy of the genetic code, where the same amino acids are encoded by alternative or synonymous codons, allows an extremely large number of nucleic acids to be made, all of which encode the engineered T7 RNA polymerase polypeptide. Thus, having knowledge of a particular amino acid sequence, those skilled in the art could make any number of different nucleic acids by simply modifying the sequence of one or more codons in a way which does not change the amino acid sequence of the protein. In this regard, the present invention specifically contemplates each and every possible variation of polynucleotides that could be made encoding the polypeptides described herein by selecting combinations based on the possible codon choices, and all such variations are to be considered specifically disclosed for any polypeptide described herein, including the variants provided in Tables 5.3, 5.4., 5.5, and/or 5.6.

In various embodiments, the codons are preferably selected to fit the host cell in which the protein is being produced. For example, preferred codons used in bacteria are used for expression in bacteria. Consequently, codon optimized polynucleotides encoding the engineered T7 RNA polymerase polypeptides contain preferred codons at about 40%, 50%, 60%, 70%, 80%, or greater than 90% of codon positions of the full length coding region.

In some embodiments, as described above, the polynucleotide encodes an engineered polypeptide having T7 RNA polymerase activity with the properties disclosed herein, wherein the polypeptide comprises an amino acid sequence having at least 80%, 81%, 82%, 83%, 84%, 85%, 86%, 87%, 88%, 89%, 90%, 91%, 92%, 93%, 94%, 95%, 96%, 97%, 98%, 99% or more identity to a reference sequence selected from SEQ ID NOS: 4 and 15, or the amino acid sequence of any variant as disclosed in Tables 5.3, 5.4., 5.5, and/or 5.6, and one or more residue differences as compared to the reference polypeptide of SEQ ID NOS: 17, 19, 21, 23, 25, 27, 29, 32, 33, 35, 37, and/or 39, or the amino acid sequence of any variant as disclosed in Tables 5.3, 5.4., 5.5, and/or 5.6 (for example 1, 2, 3, 4, 5, 6, 7, 8, 9, 10 or more amino acid residue positions). In some embodiments, the reference sequence is selected from SEQ ID NO:4 and/or 15. In some embodiments, the polynucleotide encodes an engineered polypeptide having T7 RNA polymerase activity with the properties disclosed herein, wherein the polypeptide comprises an amino acid sequence having at least 80%, 81%, 82%, 83%, 84%, 85%, 86%, 87%, 88%, 89%, 90%, 91%, 92%, 93%, 94%, 95%, 96%, 97%, 98%, 99% or more sequence identity to reference sequence SEQ ID NO:4 and/or 15, and one or more residue differences as compared to SEQ ID NO: 4 and/or 15, at residue positions selected from those provided in Tables 5.3, 5.4., 5.5, and/or 5.6, when optimally aligned with the polypeptide of SEQ ID NO:4 and/or 15.

In some embodiments, the polynucleotide encoding the engineered T7 RNA polymerase polypeptides comprises a polynucleotide sequence selected from a polynucleotide sequence encoding SEQ ID NOS: 4, 15, 17, 19, 21, 23, 25, 27, 29, 32, 33, 35, 37, and 39. In some embodiments, the polynucleotide encoding an engineered T7 RNA polymerase polypeptide has at least 80%, 81%, 82%, 83%, 84%, 85%, 86%, 87%, 88%, 89%, 90%, 93%, 95%, 96%, 97%, 98%, 99% nucleotide residue identity to SEQ ID NOS: 3, 14, 16, 18, 20, 22, 24, 26, 28, 30, 32, 34, 36, and 38. In some embodiments, the polynucleotide encoding the engineered T7 RNA polymerase polypeptides comprises a polynucleotide sequence selected from SEQ ID NOS: 3, 14, 16, 18, 20, 22, 24, 26, 28, 30, 32, 34, 36, and 38.

In some embodiments, the polynucleotides are capable of hybridizing under highly stringent conditions to a reference polynucleotide sequence selected from SEQ ID NOS: 3 and/or 14, or a complement thereof, or a polynucleotide sequence encoding any of the variant T7 RNA polymerase polypeptides provided herein. In some embodiments, the polynucleotide capable of hybridizing under highly stringent conditions encodes a T7 RNA polymerase polypeptide comprising an amino acid sequence that has one or more residue differences as compared to SEQ ID NO:4 and/or 15, at residue positions selected from any positions as set forth in Tables 5.3, 5.4., 5.5, and/or 5.6.

In some embodiments, an isolated polynucleotide encoding any of the engineered T7 RNA polymerase polypeptides provided herein is manipulated in a variety of ways to provide for expression of the polypeptide. In some embodiments, the polynucleotides encoding the polypeptides are provided as expression vectors where one or more control sequences is present to regulate the expression of the polynucleotides and/or polypeptides. Manipulation of the isolated polynucleotide prior to its insertion into a vector may be desirable or necessary depending on the expression vector. The techniques for modifying polynucleotides and nucleic acid sequences utilizing recombinant DNA methods are well known in the art.

In some embodiments, the control sequences include among other sequences, promoters, leader sequences, polyadenylation sequences, propeptide sequences, signal peptide sequences, and transcription terminators. As known in the art, suitable promoters can be selected based on the host cells used. Exemplary promoters for filamentous fungal host cells, include promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (See e.g., WO 96/00787), as well as the NA2-tpi promoter (a hybrid of the promoters from the genes for *Aspergillus niger* neutral alpha-amylase and *Aspergillus oryzae* triose phosphate isomerase), and mutant, truncated, and hybrid promoters thereof. Exemplary yeast cell promoters can be from the genes can be from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase. Other useful promoters for yeast host cells are known in the art (See e.g., Romanos et al., Yeast 8:423-488 [1992]). Exemplary promoters for use in mammalian cells include, but are not limited to those from cytomegalovirus (CMV), Simian vacuolating virus 40 (SV40), from *Homo sapiens* phosphoglycerate kinase, beta actin, elongation factor-1a or glyceraldehyde-3-phosphate dehydrogenase, or from *Gallus gallus* β-actin.

In some embodiments, the control sequence is a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice finds use in the present invention. For example, exemplary transcription terminators for filamentous fungal host cells can be obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease. Exemplary terminators for yeast host cells can be obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are known in the art (See e.g., Romanos et al., supra). Exemplary terminators for mammalian cells include, but are not limited to those from cytomegalovirus (CMV), Simian vacuolating virus 40 (SV40), or from *Homo sapiens* growth hormone.

In some embodiments, the control sequence is a suitable leader sequence, a non-translated region of an mRNA that is important for translation by the host cell. The leader sequence is operably linked to the 5' terminus of the nucleic acid sequence encoding the polypeptide. Any leader sequence that is functional in the host cell of choice may be used. Exemplary leaders for filamentous fungal host cells are obtained from the genes for *Aspergillus oryzae* TAKA amylase and *Aspergillus nidulans* triose phosphate isomerase. Suitable leaders for yeast host cells include, but are not limited to those obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention. Exemplary polyadenylation sequences for filamentous fungal host cells include, but are not limited to those from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase. Useful polyadenylation sequences for yeast host cells are also known in the art (See e.g., Guo and Sherman, Mol. Cell. Bio., 15:5983-5990 [1995]).

In some embodiments, the control sequence is a signal peptide coding region that codes for an amino acid sequence linked to the amino terminus of a polypeptide and directs the encoded polypeptide into the cell's secretory pathway. The 5' end of the coding sequence of the nucleic acid sequence may inherently contain a signal peptide coding region naturally linked in translation reading frame with the segment of the coding region that encodes the secreted polypeptide. Alternatively, the 5' end of the coding sequence may contain a signal peptide coding region that is foreign to the coding sequence. Any signal peptide coding region that directs the expressed polypeptide into the secretory pathway of a host cell of choice finds use for expression of the engineered T7 RNA polymerase polypeptides provided herein. Effective signal peptide coding regions for filamentous fungal host cells include, but are not limited to the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase. Useful signal peptides for yeast host cells include, but are not limited to those from the genes for *Saccharomyces cerevisiae* alpha-factor and *Saccharomyces cerevisiae* invertase. Useful signal peptides for mammalian host cells include but are not limited to those from the genes for immunoglobulin gamma (IgG).

In some embodiments, the control sequence is a propeptide coding region that codes for an amino acid sequence positioned at the amino terminus of a polypeptide. The resultant polypeptide is referred to as a "proenzyme", "propolypeptide", or "zymogen", in some cases). A propolypeptide can be converted to a mature active polypeptide by catalytic or autocatalytic cleavage of the propeptide from the propolypeptide.

In another aspect, the present invention also provides a recombinant expression vector comprising a polynucleotide encoding an engineered T7 RNA polymerase polypeptide, and one or more expression regulating regions such as a promoter and a terminator, a replication origin, etc., depending on the type of hosts into which they are to be introduced. In some embodiments, the various nucleic acid and control sequences described above are joined together to produce a recombinant expression vector which includes one or more convenient restriction sites to allow for insertion or substitution of the nucleic acid sequence encoding the variant T7 RNA polymerase polypeptide at such sites. Alternatively, the polynucleotide sequence(s) of the present invention are expressed by inserting the polynucleotide sequence or a nucleic acid construct comprising the polynucleotide sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus), that can be conveniently subjected to recombinant DNA procedures and can result in the expression of the variant T7 RNA polymerase polynucleotide sequence. The choice of the vector will typically depend on the compatibility of the vector with the host cell into which the vector is to be introduced. The vectors may be linear or closed circular plasmids.

In some embodiments, the expression vector is an autonomously replicating vector (i.e., a vector that exists as an extra-chromosomal entity, the replication of which is independent of chromosomal replication, such as a plasmid, an extra-chromosomal element, a minichromosome, or an artificial chromosome). The vector may contain any means for assuring self-replication. In some alternative embodiments, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

In some embodiments, the expression vector preferably contains one or more selectable markers, which permit easy selection of transformed cells. A "selectable marker" is a gene the product of which provides for biocide or viral resistance, resistance to heavy metals, prototrophy to auxotrophs, and the like. Suitable markers for yeast host cells include, but are not limited to ADE2, HIS3, LEU2, LYS2, MET3, TRP1, and URA3. Selectable markers for use in a filamentous fungal host cell include, but are not limited to, amdS (acetamidase), argB (ornithine carbamoyltransferases), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. In another aspect, the present invention provides a host cell comprising a polynucleotide encoding at least one engineered T7 RNA polymerase polypeptide of the present application, the polynucleotide being operatively linked to one or more control sequences for expression of the engineered T7 RNA polymerase enzyme(s) in the host cell. Host cells for use in expressing the polypeptides encoded by the expression vectors of the present invention are well known in the art and include but are not limited to, fungal cells, such as yeast cells (e.g., *Saccharomyces cerevisiae* and *Pichia pastoris* [e.g., ATCC Accession No. 201178]); insect cells (e.g., *Drosophila* S2 and *Spodoptera* Sf9 cells), plant cells, animal cells (e.g., CHO, COS, and BHK), and human cells (e.g., HEK293T, human fibroblast, THP-1, Jurkat and Bowes melanoma cell lines).

Accordingly, in another aspect, the present invention provides methods for producing the engineered T7 RNA polymerase polypeptides, where the methods comprise culturing a host cell capable of expressing a polynucleotide encoding the engineered T7 RNA polymerase polypeptide under conditions suitable for expression of the polypeptide. In some embodiments, the methods further comprise the steps of isolating and/or purifying the T7 RNA polymerase polypeptides, as described herein.

Appropriate culture media and growth conditions for the above-described host cells are well known in the art. Polynucleotides for expression of the T7 RNA polymerase polypeptides may be introduced into cells by various methods known in the art. Techniques include, among others, electroporation, biolistic particle bombardment, liposome mediated transfection, calcium chloride transfection, and protoplast fusion.

The engineered T7 RNA polymerase with the properties disclosed herein can be obtained by subjecting the polynucleotide encoding the naturally occurring or engineered T7 RNA polymerase polypeptide to mutagenesis and/or directed evolution methods known in the art, and as described herein. An exemplary directed evolution technique is mutagenesis and/or DNA shuffling (See e.g., Stemmer, Proc. Natl. Acad. Sci. USA 91:10747-10751 [1994]; WO 95/22625; WO 97/0078; WO 97/35966; WO 98/27230; WO 00/42651; WO 01/75767 and U.S. Pat. No. 6,537,746). Other directed evolution procedures that can be used include, among others, staggered extension process (StEP), in vitro recombination (See e.g., Zhao et al., Nat. Biotechnol., 16:258-261 [1998]), mutagenic PCR (See e.g., Caldwell et al., PCR Methods Appl., 3:S136-S140 [1994]), and cassette mutagenesis (See e.g., Black et al., Proc. Natl. Acad. Sci. USA 93:3525-3529 [1996]).

For example, mutagenesis and directed evolution methods can be readily applied to polynucleotides to generate variant libraries that can be expressed, screened, and assayed. Mutagenesis and directed evolution methods are well known in the art (See e.g., U.S. Pat. Nos. 5,605,793, 5,811,238, 5,830,721, 5,834,252, 5,837,458, 5,928,905, 6,096,548, 6,117,679, 6,132,970, 6,165,793, 6,180,406, 6,251,674, 6,277,638, 6,287,861, 6,287,862, 6,291,242, 6,297,053, 6,303,344, 6,309,883, 6,319,713, 6,319,714, 6,323,030, 6,326,204, 6,335,160, 6,335,198, 6,344,356, 6,352,859, 6,355,484, 6,358,740, 6,358,742, 6,365,377, 6,365,408, 6,368,861, 6,372,497, 6,376,246, 6,379,964, 6,387,702, 6,391,552, 6,391,640, 6,395,547, 6,406,855, 6,406,910, 6,413,745, 6,413,774, 6,420,175, 6,423,542, 6,426,224, 6,436,675, 6,444,468, 6,455,253, 6,479,652, 6,482,647, 6,489,146, 6,506,602, 6,506,603, 6,519,065, 6,521,453, 6,528,311, 6,537,746, 6,573,098, 6,576,467, 6,579,678, 6,586,182, 6,602,986, 6,613,514, 6,653,072, 6,716,631, 6,777,218, 6,917,882, 6,946,296, 6,961,664, 6,995,017, 7,024,312, 7,058,515, 7,105,297, 7,148,054, 7,288,375, 7,421,347, 7,430,477, 7,534,564, 7,620,500, 7,620,502, 7,629,170, 7,702,464, 7,747,391, 7,747,393, 7,751,986, 7,776,598, 7,783,428, 7,795,030, 7,853,410, 7,868,138, 7,873,477, 7,873,499, 7,904,249, 7,957,912, 8,014,961, 8,029,988, 8,058,001, 8,076,138, 8,018,150, 8,170,806, 8,377,681, 8,383,346, 8,457,903, 8,504,498, 8,589,085, 8,762,066, 8,849,575, 8,876,066, 8,768,871, 9,593,326, 9,665,694, and all related US and non-US counterparts; Ling et al., Anal. Biochem., 254(2):157-78 [1997]; Dale et al., Meth. Mol. Biol., 57:369-74 [1996]; Smith, Ann. Rev. Genet., 19:423-462 [1985]; Botstein et al., Science, 229: 1193-1201 [1985]; Carter, Biochem. J., 237:1-7 [1986]; Kramer et al., Cell, 38:879-887 [1984]; Wells et al., Gene, 34:315-323 [1985]; Minshull et al., Curr. Op. Chem. Biol., 3:284-290 [1999]; Christians et al., Nat. Biotechnol., 17:259-264 [1999]; Crameri et al., Nature, 391:288-291 [1998]; Crameri, et al., Nat. Biotechnol., 15:436-438 [1997]; Zhang et al., Proc. Nat. Acad. Sci. U.S.A., 94:4504-4509 [1997]; Crameri et al., Nat. Biotechnol., 14:315-319 [1996]; Stemmer, Nature, 370:389-391 [1994]; Stemmer, Proc. Nat. Acad. Sci. USA, 91:10747-10751 [1994]; US Pat. Appln. Publn. Nos. 2008/0220990, US 2009/0312196, US2014/ 0005057, US2014/0214391, US2014/0221216; US2015/ 0050658, US2015/0133307, US2015/0134315 and all related US and non-US counterparts; WO 95/22625, WO 97/0078, WO 97/35966, WO 98/27230, WO 00/42651, WO 01/75767, and WO 2009/152336; all of which are incorporated herein by reference).

In some embodiments, the enzyme variants obtained following mutagenesis treatment are screened by subjecting the enzyme variants to a defined temperature (or other assay conditions) and measuring the amount of enzyme activity remaining after heat treatments or other assay conditions. DNA containing the polynucleotide encoding the T7 RNA polymerase polypeptide is then isolated from the host cell, sequenced to identify the nucleotide sequence changes (if any), and used to express the enzyme in a different or the same host cell. Measuring enzyme activity from the expression libraries can be performed using any suitable method known in the art (e.g., standard biochemistry techniques, such as HPLC analysis).

For engineered polypeptides of known sequence, the polynucleotides encoding the enzyme can be prepared by standard solid-phase methods, according to known synthetic methods. In some embodiments, fragments of up to about 100 bases can be individually synthesized, then joined (e.g., by enzymatic or chemical litigation methods, or polymerase mediated methods) to form any desired continuous sequence. For example, polynucleotides and oligonucleotides disclosed herein can be prepared by chemical synthesis using the classical phosphoramidite method (See e.g., Beaucage et al., Tetra. Lett., 22:1859-69 [1981]; and Matthes et al., EMBO J., 3:801-05 [1984]), as it is typically practiced in automated synthetic methods. According to the phosphoramidite method, oligonucleotides are synthesized (e.g., in an automatic DNA synthesizer), purified, annealed, ligated and cloned in appropriate vectors.

Accordingly, in some embodiments, a method for preparing the engineered T7 RNA polymerase polypeptide can comprise: (a) synthesizing a polynucleotide encoding a polypeptide comprising an amino acid sequence selected from the amino acid sequence of any variant provided in Table 5.3, 5.4., 5.5, and/or 5.6, as well as SEQ ID NOS: 15, 17, 19, 21, 23, 25, 27, 29, 31, 33, 35, 37, and 39, and (b) expressing the T7 RNA polymerase polypeptide encoded by the polynucleotide. In some embodiments of the method, the amino acid sequence encoded by the polynucleotide can optionally have one or several (e.g., up to 3, 4, 5, or up to 10) amino acid residue deletions, insertions and/or substitutions. In some embodiments, the amino acid sequence has optionally 1-2, 1-3, 1-4, 1-5, 1-6, 1-7, 1-8, 1-9, 1-10, 1-15, 1-20, 1-21, 1-22, 1-23, 1-24, 1-25, 1-30, 1-35, 1-40, 1-45, or 1-50 amino acid residue deletions, insertions and/or substitutions. In some embodiments, the amino acid sequence has optionally 1, 2, 3, 4, 5, 6, 7, 8, 9, 10, 11, 12, 13, 14, 15, 16, 17, 18, 19, 20, 21, 22, 23, 24, 25, 30, 30, 35, 40, 45, or 50 amino acid residue deletions, insertions and/or substitutions. In some embodiments, the amino acid sequence has optionally 1, 2, 3, 4, 5, 6, 7, 8, 9, 10, 11, 12, 13, 14, 15, 16, 18, 20, 21, 22, 23, 24, or 25 amino acid residue deletions, insertions and/or substitutions. In some embodiments, the substitutions can be conservative or non-conservative substitutions.

The expressed engineered T7 RNA polymerase polypeptide can be assessed for any desired improved property (e.g., activity, selectivity, stability, acid tolerance, protease sensitivity, etc.), using any suitable assay known in the art, including but not limited to the assays and conditions described herein.

In some embodiments, any of the engineered T7 RNA polymerase polypeptides expressed in a host cell are recovered from the cells and/or the culture medium using any one or more of the well-known techniques for protein purification, including, among others, lysozyme treatment, sonication, filtration, salting-out, ultra-centrifugation, and chromatography.

Chromatographic techniques for isolation of the T7 RNA polymerase polypeptides include, among others, reverse phase chromatography high performance liquid chromatography, ion exchange chromatography, hydrophobic interaction chromatography, gel electrophoresis, and affinity chromatography. Conditions for purifying a particular enzyme depends, in part, on factors such as net charge, hydrophobicity, hydrophilicity, molecular weight, molecular shape, etc., and will be apparent to those having skill in the art. In some embodiments, affinity techniques may be used to isolate the improved variant T7 RNA polymerase enzymes. In some embodiments utilizing affinity chromatography purification, any antibody which specifically binds the variant T7 RNA polymerase polypeptide finds use. In some embodiments utilizing affinity chromatography purification, proteins that bind to the glycans covalently attached to T7 RNA polymerase find use. In still other embodiments utilizing affinity-chromatography purifications, any small molecule that binds to the T7 RNA polymerase active site finds use. For the production of antibodies, various host animals, including but not limited to rabbits, mice, rats, etc., are immunized by injection with a T7 RNA polymerase polypeptide (e.g., a T7 RNA polymerase variant), or a fragment thereof. in some embodiments, the T7 RNA polymerase polypeptide or fragment is attached to a suitable carrier, such as BSA, by means of a side chain functional group or linkers attached to a side chain functional group.

In some embodiments, the engineered T7 RNA polymerase polypeptide is produced in a host cell by a method comprising culturing a host cell (e.g., S. cerevisiae, Daucus carota, Nicotiana tabacum, H. sapiens (e.g., HEK293T), or Cricetulus griseus (e.g., CHO)) comprising a polynucleotide sequence encoding an engineered T7 RNA polymerase polypeptide as described herein under conditions conducive to the production of the engineered T7 RNA polymerase polypeptide and recovering the engineered T7 RNA polymerase polypeptide from the cells and/or culture medium.

In some embodiments, the invention encompasses a method of producing an engineered T7 RNA polymerase polypeptide comprising culturing a recombinant eukaryotic cell comprising a polynucleotide sequence encoding an engineered T7 RNA polymerase polypeptide having at least 80%, 81%, 82%, 83%, 84%, 85%, 86%, 87%, 88%, 89%, 90%, 95%, 96%, 97%, 98%, 99%, or 100% sequence identity to reference sequences SEQ ID NOS: 4 and/or 15, and one or more amino acid residue differences as compared to SEQ ID NO: 4 and/or 15, selected from those provided in Tables 5.3, 5.4., 5.5, and/or 5.6, and/or combinations thereof when optimally aligned with the amino acid sequence of SEQ ID NO: 4 and/or 15, under suitable culture conditions to allow the production of the engineered T7 RNA polymerase polypeptide and optionally recovering the engineered T7 RNA polymerase polypeptide from the culture and/or cultured bacterial cells.

In some embodiments, once the engineered T7 RNA polymerase polypeptides are recovered from the recombinant host cells or cell culture medium, they are further purified by any suitable method(s) known in the art. In some additional embodiments, the purified T7 RNA polymerase polypeptides are combined with other ingredients and compounds to provide compositions and formulations comprising the engineered T7 RNA polymerase polypeptide as appropriate for different applications and uses (e.g., pharmaceutical compositions). In some additional embodiments, the purified T7 RNA polymerase polypeptides, or the formulated T7 RNA polymerase polypeptides are lyophilized Compositions:

The present invention provides various compositions and formats, including but not limited to those described below. In some embodiments, the present invention provides engineered T7 RNA polymerase polypeptides suitable for use in compositions for diagnostic purposes.

EXPERIMENTAL

The following Examples, including experiments and results achieved, are provided for illustrative purposes only and are not to be construed as limiting the present invention.

In the experimental disclosure below, the following abbreviations apply: ppm (parts per million); M (molar); mM (millimolar), uM and μM (micromolar); nM (nanomolar); mol (moles); gm and g (gram); mg (milligrams); ug and μg (micrograms); L and l (liter); ml and mL (milliliter); cm (centimeters); mm (millimeters); um and μm (micrometers); sec. (seconds); min(s) (minute(s)); h(s) and hr(s) (hour(s)); U (units); MW (molecular weight); rpm (rotations per minute); rcf (relative centrifugal force); ° C. (degrees Centigrade); CDS (coding sequence); DNA (deoxyribonucleic acid); RNA (ribonucleic acid); E. coli W3110 (commonly used laboratory E. coli strain, available from the Coli Genetic Stock Center [CGSC], New Haven, Conn.); HPLC (high pressure liquid chromatography); MWCO (molecular weight cut-off); SDS-PAGE (sodium dodecyl sulfate polyacrylamide gel electrophoresis); T7RNAP (T7 RNA polymerase); PES (polyethersulfone); CFSE (carboxyfluorescein succinimidyl ester); IPTG (isopropyl β-D-1-thiogalactopyranoside); PMBS (polymyxin B sulfate); NADPH (nicotinamide adenine dinucleotide phosphate); GlDH (glutamate dehydrogenase); FIOPC (fold improvements over positive control); LB (Luria broth); MeOH (methanol); Athens Research (Athens Research Technology, Athens, Ga.); NEB (New England Biolabs, Ipswich, Mass.); Ion Torrent (Ion Torrent, Gilford, N.H.); ProSpec (ProSpec Tany Technogene, East Brunswick, N.J.); Sigma-Aldrich (Sigma-Aldrich, St. Louis, Mo.); Ram Scientific (Ram Scientific, Inc., Yonkers, N.Y.); Pall Corp. (Pall, Corp., Pt. Washington, N.Y.); Millipore (Millipore, Corp., Billerica Mass.); Difco (Difco Laboratories, BD Diagnostic Systems, Detroit, Mich.); Molecular Devices (Molecular Devices, LLC, Sunnyvale, Calif.); Kuhner (Adolf Kuhner, AG, Basel, Switzerland); Axygen (Axygen, Inc., Union City, Calif.); Toronto Research Chemicals (Toronto Research Chemicals Inc., Toronto, Ontario, Canada); Cambridge Isotope Laboratories, (Cambridge Isotope Laboratories, Inc., Tewksbury, Mass.); Applied Biosystems (Applied Biosystems, part of Life Technologies, Corp., Grand Island, N.Y.), Agilent (Agilent Technologies, Inc., Santa Clara, Calif.); Thermo Scientific (part of Thermo Fisher Scientific, Waltham, Mass.); Ion Torrent NGS (Ion Torrent Next Generation Sequencing); Li-COR (Li-COR, Lincoln, Nebr.); UVP (UVP, Upland, Calif.); Biotium (Biotium, Inc., Fremont, Calif.); Corning (Corning, Inc., Palo Alto, Calif.); Megazyme (Megazyme International, Wicklow, Ireland); Enzo (Enzo Life Sciences, Inc., Farmingdale, N.Y.); GE Healthcare (GE Healthcare Biosciences, Piscataway, N.J.); Pierce (Pierce Biotechnology (now part of Thermo Fisher Scientific), Rockford, Ill.); LI-COR (LI-COR Biotechnology, Lincoln, Nebr.); Amicus (Amicus Therapeutics, Cranbury, N.J.); Phenomenex (Phenomenex, Inc., Torrance, Calif.); Optimal (Optimal Biotech Group, Belmont, Calif.); and Bio-Rad (Bio-Rad Laboratories, Hercules, Calif.).

Example 1

T7 RNA Polymerase Gene Acquisition and Construction of Expression Vectors

The wild-type (WT) T7 RNA Polymerase enzyme (SEQ ID NO:2) is encoded by the genome of the bacteriophage T7 (SEQ ID NO:1). A synthetic gene (SEQ ID NO:3) encoding a 6-histidine tagged version of the T7 RNA Polymerase (SEQ ID NO:4) was constructed and subcloned into the *Escherichia coli* expression vector pCK100900i (See e.g., U.S. Pat. No. 7,629,157 and US Pat. Appln. Publn. 2016/0244787, both of which are hereby incorporated by reference). These plasmid constructs were transformed into an *E. coli* strain derived from W3110. Directed evolution techniques generally known by those skilled in the art were used to generate libraries of gene variants from these plasmids (See e.g., U.S. Pat. No. 8,383,346 and WO 2010/144103, both of which are hereby incorporated by reference). The substitutions in the enzyme variants described herein are indicated with reference to the 6His-tagged WT T7 RNA Polymerase enzyme (i.e., SEQ ID NO:4) or variants thereof, as indicated.

Example 2

T7 RNA Polymerase Expression and Purification in High-Throughput (HTP)

In this Example, experiments conducted on T7 RNA polymerase expression and purification of T7 RNA polymerase variants are described.
High-Throughput (HTP) Growth of T7 DNA Polymerase and Variants
Transformed *E. coli* cells were selected by plating onto LB agar plates containing 1% glucose and 30 µg/ml chloramphenicol. After overnight incubation at 37° C., colonies were placed into the wells of 96-well shallow flat bottom NUNC™ (Thermo-Scientific) plates filled with 180 µl/well LB medium supplemented with 1% glucose and 30 µg/ml chloramphenicol. The cultures were allowed to grow overnight for 18-20 hours in a shaker (200 rpm, 30° C., and 85% relative humidity; Kuhner). Overnight growth samples (20 µL) were transferred into Costar 96-well deep plates filled with 3804 of Terrific Broth supplemented with 30 µg/ml chloramphenicol. The plates were incubated for 120 minutes in a shaker (250 rpm, 30° C., and 85% relative humidity; Kuhner) until the $OD_{600}$ reached between 0.4-0.8. The cells were then induced with 40 µL of 10 mM IPTG in sterile water and incubated overnight for 18-20 hours in a shaker (250 rpm, 30° C., and 85% relative humidity; Kuhner). The cells were pelleted (4000 rpm×20 min), the supernatants were discarded, and the cells were frozen at −80° C. prior to analysis.
Lysis of HTP Pellets
Cell pellets were resuspended in 400 µL of lysis buffer (50 mM sodium phosphate, pH 7.5, 10 mM imidazole, 0.1% Tween 20®, 1 mg/ml lysozyme, and 0.5 mg/ml polymyxin B sulfate), and the mixture was agitated for 2 h at room temperature. Lysates were then pelleted (4000 rpm×5 mM), and the clarified supernatants were reserved for purification.
HTP Purification of T7RNAP from Crude Lysates
T7RNAP was purified from clarified *E. coli* lysates by metal-affinity chromatography using HisPur™ Ni-NTA spin plate (Thermo Fisher) according to the manufacturer's instructions. HisPur™ Ni-NTA spin plate was equilibrated with a total of 800 µl of wash buffer (50 mM sodium phosphate pH 7.5, 300 mM NaCl, 10 mM imidazole, 0.1% v/v TWEEN-20® reagent) per well. Then, 100 µl of binding buffer was added to each well followed by 100 ul of HTP lysate containing T7RNAP. The plate was briefly shaken, centrifuged for 1 min at 1100 relative centrifugal force (rcf) and 4° C., and then incubated at room temperature for 15 min. The plate was washed twice with 600 µl of wash buffer (50 mM sodium phosphate pH 7.5, 300 mM NaCl, 25 mM imidazole, 0.1% v/v TWEEN-20® reagent) per well, with 3 min centrifugations at 1100 rcf and 4° C. for each wash. Enzyme samples were eluted with the addition of 105 µl elution buffer (50 mM sodium phosphate pH 7.5, 300 mM NaCl, 250 mM imidazole, 0.1% v/v TWEEN®-20 reagent) by centrifugation for 1 min @ 1100 rcf at 4° C.
Eluates were buffer-exchanged using Zeba™ Spin desalting plates (Thermo Fisher). Briefly, plates were equilibrated twice with 375µl of 2×T7RNAP storage buffer (100 mM Tris.HCl pH 8.0, 200 mM NaCl, 2 mM DTT, 2 mM EDTA, 0.2% w/v Triton X-100) per well and centrifuged for 2 min @ 1100 rcf at 4° C. Desalting plates were loaded with 90µl of the HisPur™ Ni-NTA spin plate eluate and centrifuged for 2 min @ 1100 rcf at 4° C. The eluate from the desalting plate was retained and mixed with an equal volume of glycerol for a final storage buffer concentration of 50 mM Tris HCl pH 7.9, 100 mM NaCl, 1 mM DTT, 1 mM EDTA, 0.1% v/v Triton X-100 and 50% glycerol (v/v).
The absence of RNase contamination in purified preps was confirmed using the RNase Alert assay (IDT, Life Technologies). SDS-PAGE analysis of T7RNAP samples showed no detectable contaminating bands for most samples.
For in vitro transcription reactions using HTP-purified T7RNAP, purified polymerase was added to a final concentration of 10% of the total reaction volume (5% for enzyme from shake flask cultures).

Example 3

Shake Flask Expression and Purification of T7 RNA Polymerase

In this Example, experiments involving shake flask expression and purification of T7RNAP are described.

Shake Flask Expression

Selected HTP cultures grown as described in Example 2, were plated onto LB agar plates with 1% glucose and 30 µg/ml chloramphenicol and grown overnight at 37° C. A single colony from each culture was transferred to 6 ml of LB broth with 1% glucose and 30 µg/ml chloramphenicol. The cultures were grown for 18 h at 30° C., 250 rpm, and subcultured at a dilution of approximately 1:10 into 250 ml of Terrific Broth with 30 µg/ml of chloramphenicol, to a final $OD_{600}$ of 0.2. The cultures were incubated for approximately 3 hours at 30° C., 250 rpm, to an $OD_{600}$ of 0.6-0.8, and then induced with the addition of IPTG at a final concentration of 1 mM. The induced cultures were incubated for 20 h at 30° C., 250 rpm. Following this incubation period, the cultures were centrifuged at 4000 rpm×10 min. The culture supernatant was discarded, and the pellets were resuspended in 35 mls Lysis buffer (50 mM $NaH_2PO_4$, pH 7.5, 500 mM NaCl, 0.1% Tween-20, 10 mM imidazole). This cell suspension was chilled in an ice bath and lysed using a Microfluidizer cell disrupter (Microfluidics M-110L). The crude lysate was pelleted by centrifugation (16,000 rpm for 60 mM at 4° C.), and the supernatant was then filtered through a 0.2 µm PES membrane to further clarify the lysate.

Purification of T7 RNA Polymerase from Shake Flask Lysates

T7RNAP lysates were purified using an AKTA Start purification system and a 5 ml HisTrap FF column (GE Healthcare) using the AC Step HiF setting (the run parameters are provided below). The SF wash buffer was comprised of 50 mM sodium phosphate pH 7.5, 500 mM NaCl, 0.1% v/v TWEEN-20® reagent (Sigma), and 25 mM imidazole. The SF Elution buffer was comprised of 50 mM sodium phosphate pH 7.5, 500 mM NaCl, 0.1% v/v TWEEN-20® reagent (Sigma), and 300 mM imidazole.

TABLE 3.1

Purification Parameters

| Parameter | Volume |
| --- | --- |
| Column volume | 5 ml |
| Flow rate | 5 ml/min |
| Pressure limit | 0.3 MPa |
| Sample volume | 35 mls |
| Equilibration volume | 5 column volumes (CV) = 25 mls |
| Wash Unbound volume | 15 CV = 75 mls |
| Elution | Isocratic (step) |
| Elution volume | 5 CV = 25 mls |
| Fraction volume | 3 mls |
| RE-equilibration volume | 5 CV = 25 mls |

The single five most concentrated 3 ml fractions were identified by UV absorption (A280), and dialyzed overnight in 2×T7RNAP storage buffer (100 mM Tris HCl pH 7.9, 200 mM NaCl, 2 mM DTT, 2 mM EDTA, 0.2% v/v Triton X-100) overnight in a 10K Slide-A-Lyzer™ dialysis cassette (Thermo Fisher) for buffer exchange for 16 hours, followed by a second buffer exchange for 24 hours. An equal volume of glycerol was added to the dialyzed material. Enzyme concentrations in the preparations were measured by gel densitometry and absorption at 280 nm.

Example 4

Transcription Reactions

Transcription reactions were assembled with the cap analog alpha, gamma-Bis (N7-methylguanosine) triphosphate (also referred to herein as "m7G(5')ppp(5')m7G," "capped-GTP," or "Cap") (See, Grudzien et. al., RNA, 10:1479-87 [2004]). An engineered transcription DNA template GlmS-16A (SEQ ID NO: 5) includes a T7RNAP promoter sequence coupled to coding sequence for the *Bacillus anthracis* GlmS riboswitch (SEQ ID NO:6). Upon induction with its ligand, glucosamine-6-phosphate, the GlmS riboswitch self-cleaves and releases a 16-mer RNA nucleotide (SEQ ID NO: 7) from the 5' end of the transcript, which includes the cap structure or an uncapped 5' phosphate. This small 16-mer RNA oligonucleotide cleavage product was amenable to ionization and analysis by LC-MS, which was used to distinguish the capped and uncapped species.

Reactions were assembled in a total of 30 ul per well with final concentrations of 50 mM Tris HCl pH 7.9, 30 mM $MgCl_2$, 10 mM DTT, 6 mM ATP, 6 mM CTP, 6 mM UTP, 4.8 mM GTP, 1.2 mM m7G(5')ppp(5')m7G, 50 ng/µl GlmS-16A transcription template, 1 U/µl RNasin inhibitor, and 6.4 mM glucosamine-6-phosphate, and included 10% (v/v) (3 ul) of purified and desalted T7RNAP from Example 3. For HTP screening, reactions were incubated at 37° C. for 4 h and quenched with an equal (30 µl) volume of 40 mM EDTA. The total of m7G(5')ppp(5')m7G and GTP was held at 6 mM. Glucosamine-6-phosphate was included at the start of the reaction, and cleavage of the riboswitch was allowed to proceed during the 4 hour in vitro transcription.

Example 5

LC-MS Activity Assay

This Example describes an LC-MS method developed for separation of smaller RNA fragments using a Thermo LTQ MS system for the analysis of shorter capped 5'- and uncapped 5' triphosphate cleavage products.

The 7meG-capped and 5' triphosphate uncapped 16-mer cleavage products (SEQ ID NO: 7) were chromatographically separated (See, FIG. 1) from reactants and higher MW RNAs with a reverse phase ion-paired HPLC method using a C18 column and HFIP mobile phase commonly used for the resolution of oligonucleotides for mass spectrometry (See, Table 5.1).

TABLE 5.1

LC-MS Method Used for Detecting Capped and Uncapped 16-mer Cleavage Products

| | |
| --- | --- |
| Instrument | Accela HPLC coupled with Thermo LTQ MS system; fused silica tubing from column to MS; bypass UV. The UV detector was reconnected for Stage 2 screening experiments to allow measurement of cleaved product |

TABLE 5.1-continued

LC-MS Method Used for Detecting Capped and Uncapped 16-mer Cleavage Products

| | |
|---|---|
| Column | Waters Xterra MS C18, 50 × 2.1 mm, 5 μm, with Phenomenex C18 guard |
| Mobile Phase | A: 400 mM HFIP, ~16.3 mM* TEA in water, pH 7.9 (*adjust TEA to reach pH)<br>(weigh HFIP, dissolve TEA additions slowly)<br>B: 200 mM HFIP, ~8.15 mM TEA in 50/50 water/methanol (use A to make B) |
| Flow Rate | 240 ul/min |
| Gradient | 60% A at 0'; ramp to 50% A at 1.25'; ramp to 20% A at 5'; back to 60% A at 5.5', and hold at 60% A through 7.5' (end). |
| Detection | LTQ; divert flow from MS between 0-2 min and again between 5.5-7.5 min.<br>BP extracted ions for:<br>Uncapped 16-mer product = 903.8, 1084.6, 1355.9, 1361.4, 1808.1, 1815.6, 1820.8<br>Capped 16-mer product = 952.7, 1143.4, 1429.2, 1438.7, 1906.1, 1918.6, 1931.3 |
| MS Conditions | MS Polarity: Negative; Ionization: ESI; Mode: Q1 Scan from 800-2000; Probe Height: B; Sheath gas: 20; Aux gas: 5; Sweep gas: 0; Spray V: 5; Cap temp: 275 C.; Cap V: −20; Tube lens: −85; Multipole 00: 3.5; Lens 0: 5.5; Multipole 0: 5.75; Lens 1: 38; Gate: 78; Multipole 1: 16; Multipole RF: 400; Front Lens 5.75. |
| Column Temp. | 35° C. |
| Sampler Temp. | 7° C. |
| Injection Volume | 10 μL |
| Runtime | 7.5 min (with injector cycle time, it takes ~8.4 min/sample.) |
| Peak Identification Details | RT of capped & uncapped products: ~4.5 min (RT shifts with each batch of mobile phase) |

Base-peak extractions for capped and uncapped 16-mer cleavage products were performed using seven ions for each species, including multiple negatively charged ions and metal adducts. The peak intensities for these seven ions were used to derive the signal for each of the capped and uncapped 16-mer cleavage products. These ions include multiple charged states as well as sodium and potassium adducts (See, Table 5.2). All ions were observed within 1 mass unit of the expected values.

TABLE 5.2

Ions Measured for Mass Spec Integration

| Product | Ion Name | Charge State | Adduct | Theoretical m/z | Measured m/z | Measured-Theoretical m/z |
|---|---|---|---|---|---|---|
| Uncapped 16-mer | (M − 6H)/6 | 6− | | 903.7 | 903.8 | 0.1 |
| | (M − 5H)/5 | 5− | | 1084.6 | 1084.6 | 0 |
| | (M − 4H)/4 | 4− | | 1356 | 1355.9 | −0.1 |
| | (M + Na − 5H)/4 | 4− | Na | 1361.5 | 1361.4 | −0.1 |
| | (M − 3H)/3 | 3− | | 1808.3 | 1808.1 | −0.2 |
| | (M + Na − 4H)/3 | 3− | Na | 1815.7 | 1815.6 | −0.1 |
| | (M + K − 4H)/3 | 3− | K | 1821 | 1820.8 | −0.2 |
| Capped 16-mer | (M − 6H)/6 | 6− | | 952.9 | 952.7 | −0.02 |
| | (M − 5H)/5 | 5− | | 1143.6 | 1143.4 | −0.02 |
| | (M − 4H)/4 | 4− | | 1429.8 | 1429.2 | −0.06 |
| | (M + K − 5H)/4 | 4− | K | 1439.3 | 1438.7 | −0.06 |
| | (M − 3H)/3 | 3− | | 1906.7 | 1906.1 | −0.06 |
| | (M + K − 4H)/3 | 3− | K | 1919.4 | 1918.6 | −0.08 |
| | (M + 2K − 5H)/3 | 3− | 2K | 1932.1 | 1931.3 | −0.08 |

Capping performance relative the WT T7RNAP (i.e., the "Fold-Improvement Over Parent," or "FIOP") was calculated by dividing the capped/uncapped peak intensity ratios for each sample by the ratios calculated for WT parental controls present on each plate (n=6 to 10). The FIOP value was used to rank variant performance relative to the WT T7RNAP or the library parent, which were included as controls on every plate. By using this relative quantitation method, it was possible to cancel out differences in ionization that were inherent between the capped and uncapped species, as well as variations in signal caused by the batch of HFIP mobile phase and EDTA concentration. In vitro transcription reactions were performed as described in Example 4, with reaction times and m7G(5')ppp(5')m7G concentrations as indicated in the tables that follow. Table 5.3, 5.4, and 5.5 report the average activity improvement for 3 to 6 replicates. Table 5.6 reports the average activity improvement for variants where replicated information is available.

TABLE 5.3

T7RNAP Variant Activity Improvement

| Variant # | Activity improvement | Amino Acid Changes Relative to SEQ ID NO: 4 |
|---|---|---|
| 1 | +++ | A397W |
| 2 | +++ | R401V |
| 3 | +++ | A397M |
| 4 | +++ | A397F |
| 5 | +++ | R401S |
| 6 | +++ | R401I |
| 7 | +++ | E357R |
| 8 | +++ | E357K |
| 9 | +++ | A32V/E357I |
| 10 | +++ | K394R |
| 11 | +++ | E357N |
| 12 | +++ | E357W |
| 13 | +++ | K394A |
| 14 | +++ | K394L |
| 15 | ++ | E97D/E357G |
| 16 | ++ | E357Q |
| 17 | ++ | E357L |
| 18 | ++ | E357S |
| 19 | ++ | A397Q |
| 20 | ++ | E357M |
| 21 | ++ | E357V |
| 22 | ++ | E357T |

TABLE 5.3-continued

T7RNAP Variant Activity Improvement

| Variant # | Activity improvement | Amino Acid Changes Relative to SEQ ID NO: 4 |
|---|---|---|
| 23 | ++ | R639H |
| 24 | ++ | E357L |
| 25 | ++ | E357G |
| 26 | ++++ | P664W |
| 27 | +++ | D660W |
| 28 | +++ | D513W |
| 29 | +++ | D660T |
| 30 | +++ | D660S |
| 31 | +++ | K167N/S514L |
| 32 | +++ | D660C |
| 33 | +++ | D513R |
| 34 | ++ | S514L |
| 35 | ++ | D513L |
| 36 | ++ | S514I |
| 37 | ++ | A136I |
| 38 | ++ | D513T |
| 39 | ++ | A136E |
| 40 | ++ | S514F |
| 41 | ++ | D660A |
| 42 | ++ | D513C |
| 43 | ++ | D513F |
| 44 | ++ | D660N/H806Y |
| 45 | + | A302V/D513G |
| 46 | + | D660M |
| 47 | + | S514Y |
| 48 | + | D513K |
| 49 | +++ | S635W |
| 50 | +++ | D137W |
| 51 | +++ | T637G |
| 52 | +++ | Q656F |
| 53 | ++ | S404Y |
| 54 | ++ | R314C/R401V |
| 55 | ++ | M446W |
| 56 | ++ | T661E |
| 57 | ++ | T637G |
| 58 | + | T250D |
| 59 | + | T643A |
| 60 | + | R401L |
| 61 | + | D478F |
| 62 | + | A582N |
| 63 | + | Q656W |
| 64 | + | N444I |
| 65 | + | S404E |
| 66 | + | N444F |
| 67 | + | V636L |
| 68 | + | N444V |
| 69 | + | T661Y |
| 70 | + | Y392D |
| 71 | + | T637P |
| 72 | + | F653C |
| 73 | + | E49G/M642L |
| 74 | + | M446Y |
| 75 | + | D478M |
| 76 | + | R393L |
| 77 | + | R401A |
| 78 | + | T637S |
| 79 | + | R160L/T643S |
| 80 | + | M642L |
| 81 | + | D478W |
| 82 | + | R393Y |
| 83 | + | N444H |
| 84 | + | A645V |

Reactions were performed with 1.2 mM m7G(5')ppp(5')m7G and 4.8 mM GTP in a 4 hour reaction. Activity levels were determined relative to the reference polypeptide of SEQ ID NO: 4. The activity improvement values correspond to:
++++ = >5
+++ = 1.9 to 4.99
++ = 1.5 to 1.89
+ = 1.3 to 1.49

TABLE 5.4

T7RNAP Variant Activity Improvement

| Variant # | Activity improvement | Amino Acid Changes Relative to SEQ ID NO: 15 |
|---|---|---|
| 85 | +++ | D513L/D660W |
| 86 | +++ | S635W/D660T |
| 87 | +++ | D137W/R401S/D513R |
| 88 | +++ | D137W/R401I |
| 89 | +++ | D137W/Q656F |
| 90 | +++ | S635W/Q656F |
| 91 | +++ | D137W/S635W |
| 92 | +++ | D660T |
| 93 | +++ | D137W/D513W |
| 94 | +++ | D137W/D513R/K621R |
| 95 | ++ | D137W/R401S/D513W |
| 96 | ++ | D137W/R401V |
| 97 | ++ | L113M/D137W/D513R |
| 98 | ++ | D137W/R401S |
| 99 | ++ | D513R/S635W/Q656F |
| 100 | ++ | D137W/R401S |
| 101 | + | D513L/S635W |
| 102 | + | D660S |
| 103 | + | D137W |
| 104 | + | R401S/S635W |
| 105 | + | R401S/D513R/S635W |
| 106 | +++ | E357R/K394R/R401V/S404Y/S514L |
| 107 | +++ | R401V/S404Y/S514L |
| 108 | +++ | A136I/K394R/S404Y/M446W |
| 109 | ++ | A136E/S404Y/M446W |
| 110 | ++ | A136I/R401V/S404Y |
| 111 | ++ | R401V/S404Y |
| 112 | ++ | A136E/E357I/S404Y/S514I |
| 113 | + | A136I/E357I/S514F |
| 114 | + | A136E/S404Y/S514F |
| 115 | + | E357R/S514F |
| 116 | + | A136I/E357K/S514F |
| 117 | + | A136I/M446W |
| 118 | + | E357N/K394R/M446W/S514I |
| 119 | + | A136I/R401V |
| 120 | + | A136E/S514F |
| 121 | + | A136I/S514I |
| 122 | + | K394R/M446W/S514I |

Screening was conducted with 1 mM m7G(5')ppp(5')m7G, 5 mM GTP in a 16 hour reaction. Activity levels were determined relative to the reference polypeptide of SEQ ID NO: 15. The reported activity improvement values correspond to:
+++ = ≥2.5
++ = 2 to 2.49
+ = 1.3 to 1.99

It was noted that Variant 85 had undetectable levels of uncapped mRNA in the LC-MS assay.

TABLE 5.5

T7RNAP Variant Activity Improvement

| Variant # | Activity improvement | Amino Acid Changes Relative to SEQ ID NO: 4 |
|---|---|---|
| 123 | +++ | D513W/S635W/D660F |
| 124 | +++ | D513Y/D660W/P664W |
| 125 | +++ | D513W/S635W/D660F |
| 126 | +++ | D513W/S635W/P664W |
| 127 | +++ | A475V/D513W/S635W/D660Y |
| 128 | +++ | D660Y/P664W |
| 129 | ++ | D513F/D660W/P664Y |
| 130 | ++ | A397W/D513W/S635W/D660W |
| 131 | ++ | A397W/D513W/S635W |
| 132 | ++ | A397Y/D513W/S635W/D660F |
| 133 | + | D513Y/S635W/D660F |
| 134 | + | D513Y/S635W/D660Y |
| 135 | + | A397F/D513W/S635W |
| 136 | + | A397W/D513Y/S635W/D660F |

TABLE 5.5-continued

T7RNAP Variant Activity Improvement

| Variant # | Activity improvement | Amino Acid Changes Relative to SEQ ID NO: 4 |
|---|---|---|
| 137 | + | A397W/D513Y/S635W |
| 138 | + | A397F/D513Y/S635W |

Screening with 1 mM m7G(5')ppp(5')m7G, 5 mM GTP in a 16 hour reaction. Activity levels were determined relative to the reference polypeptide of SEQ ID NO: 15. The activity improvement values correspond to:
+++ = ≥2.5
++ = 2 to 2.49
+ = 1.3 to 1.99

TABLE 5.6

T7RNAP Variant Activity Improvement

| Variant # | Activity improvement | Amino Acid Changes Relative to SEQ ID NO: 4 |
|---|---|---|
| 130 | +++ | A397W/D513W/S635W/D660W |
| 123 | +++ | D513W/S635W/D660F |
| 124 | +++ | D513Y/D660W/P664W |
| 131 | +++ | A397W/D513W/S635W |
| 128 | +++ | D660Y/P664W |
| 129 | +++ | D513F/D660W/P664Y |
| 135 | +++ | A397F/D513W/S635W |
| 127 | +++ | A475V/D513W/S635W/D660Y |
| 139 | +++ | A397Y/D660F/P664W |
| 126 | +++ | D513W/S635W/P664W |
| 140 | +++ | A397W/D513W/S635W/Q656Y |
| 134 | +++ | D513Y/S635W/D660Y |
| 141 | +++ | A397W/S635W/Q656F/P664W |
| 133 | +++ | D513Y/S635W/D660F |
| 136 | +++ | A397W/D513W/S635W/D660F |
| 142 | +++ | D660W/P664F |
| 132 | +++ | A397Y/D513W/S635W/D660F |
| 143 | ++ | A397F/D513F/S635W/D660W |
| 137 | ++ | A397W/D513Y/S635W |
| 144 | ++ | S635F/Q656Y/P664W |
| 145 | ++ | D513W/S635W |
| 146 | ++ | A397W/D513W/S635W/D660Y/P664Y |
| 147 | ++ | A397F/D513Y/S635W |
| 148 | ++ | S635W/D660W |
| 138 | ++ | A397F/D513Y/S635W |
| 149 | ++ | A397W/D513Y/S635W/Q656Y/D660W/P664W |
| 150 | ++ | A397W/D513F/S635W |
| 151 | ++ | D513F/D660W/P664F |
| 152 | ++ | D513F/S635W/P664W |
| 153 | ++ | D513F/S635W/Q656W |
| 154 | ++ | A397W/D513W/P664W |
| 155 | ++ | S635W/P664W |
| 156 | ++ | A397W/S635W/D660W |
| 157 | ++ | D513Y/S635W/D660Y/P664F |
| 158 | ++ | A397Y/D513F/S635W/P664W |
| 159 | ++ | S635W/D660F |
| 160 | ++ | A397W/D660F/P664Y |
| 161 | ++ | A397W/S635W |
| 162 | ++ | A397F/D513W/S635W/Q656F/P664F |
| 163 | ++ | D513Y/S635W |
| 164 | ++ | A397F/D513F/S635W |
| 165 | ++ | A397W/D513W/S635F |
| 166 | ++ | A397W/D660F/P664F |
| 167 | ++ | A397W/S635W/D660Y |
| 168 | ++ | A397F/D513Y/S635W/P664F |
| 169 | ++ | A397W/D513F/D660Y/P664F |
| 170 | ++ | P664W |
| 171 | ++ | S635W/Q656W |
| 172 | ++ | A397F/S635W/D660F |
| 173 | ++ | A397W/S635W/P664F |
| 174 | ++ | D513Y/S635F/P664W |
| 175 | ++ | A397F/P664W |
| 176 | ++ | A397Y/S635W |
| 177 | + | L658P |
| 178 | + | S635F/Q656F/P664Y |
| 179 | + | A397W/S635F/P664F |
| 180 | + | D513Y/D660Y/P664F |
| 181 | + | A397Y/D513W/S635F/P664Y |
| 182 | + | D660F/P664Y |
| 183 | + | A397F/S635W |
| 184 | + | A397F/D513W/P664W |
| 185 | + | A397W/D513F/D660W |
| 186 | + | A397W/S635W/P664W/A850T |
| 187 | + | A397W/D513F/S635F/Q656F/D660F/P664W |
| 188 | + | A397W/D513W/P664F |
| 189 | + | A397W/S635W/Q656F/P664Y |
| 190 | + | A397W/D513W/S635F/D660W |
| 191 | + | D513F/S635W |
| 192 | + | A397W/S635W/Q656F/P664F |
| 193 | + | A397W/D513Y/S635W/Q656Y/P664Y |
| 194 | + | S635W |
| 195 | + | D513S/S635W/Q656W/D660F |
| 196 | + | D513Y/S635R/Q656F/P664Y |
| 197 | + | D513W/S635F |
| 198 | + | Q656W/D660W/P664Y |
| 199 | + | A397W/D660W |
| 200 | + | A397W/D513W/S635W/D660W/P664Y |
| 201 | + | D513W/Q656Y/D660W |
| 202 | + | K399E/S635F/D660W |
| 203 | + | D513W/D660W |
| 204 | + | A397Y/S635W/Q656F/D660Y/P664W |
| 205 | + | D660F/P664F |
| 206 | + | A397W/S635F |
| 207 | + | A397Y/D513W/Q656W/D660W |
| 208 | + | D513S/S635F/D660F/P664Y |
| 209 | + | A397F/D513Y/S635W/Q656W |
| 210 | + | D513F/D660W |
| 211 | + | D513W/D660F |
| 212 | + | A397W/D513F |
| 213 | + | A397W/D513W |
| 214 | + | Q656W/D660F/P664Y |
| 215 | + | D513Y/P664Y |
| 216 | + | A397W/D513Y/S635F |
| 217 | + | D513W/Q656W/P664W |
| 218 | + | A397W/D513W/D660W |
| 219 | + | A397W/D513F/D660F |
| 220 | + | A397F/D660W |
| 221 | + | A397F/S635F/D660W |
| 222 | + | A397Y/S635W/D660W |
| 223 | + | D513Y/D660W |
| 224 | + | A397W/P664F |
| 225 | + | A397W/D513W/D660W/P664Y |
| 226 | + | P664F |
| 227 | + | A397Y/D513F/S635W/Q656F/D660W/P664F |
| 228 | + | S635F/D660W/P664F |
| 229 | + | A397W/D513Y/Q656H/D660W |
| 230 | + | A397F/D513F/S635F |
| 231 | + | A397W |
| 232 | + | A397Y/S635F |
| 233 | + | A397Y/D513Y |
| 234 | + | D513F/S635F |
| 235 | + | A397F/D513F |
| 236 | + | A397F/D513Y |
| 237 | + | D513W |
| 238 | + | A397Y |
| 239 | + | A397F |
| 240 | + | D513F |
| 241 | + | A397W/D513W/S635F/Q656W/D660F |
| 242 | + | A397W/E837K |
| 243 | + | D660F |
| 244 | + | D513Y/S635F |

Screening with 1 mM m7G(5')ppp(5')m7G, 5 mM GTP. Activity levels were determined relative to the reference polypeptide of SEQ ID NO: 4. The activity improvement values correspond to:
+++ = ≥15
++ = 7 to 14.9
+ = 2 to 6.9

Example 6

Determination of RNA Yield

In vitro transcription reactions were performed as described in Example 4, but using a luciferase template (SEQ ID NO: 10). mRNA yields from in vitro transcription reactions were performed according to the manufacturer's protocol for the Quant-iT RNA Assay kit (broad-range, Q-33140, Thermo Fisher). mRNA abundance was calculated using a standard curve derived for the mRNA standards provided with the assay kit.

TABLE 6.1

RNA Yields

| SEQ ID NO: | VARIANT ID NO: | RNA Yield |
|---|---|---|
| 4 | N/A | ++ |
| 15 | 26 | ++ |
| 17 | 86 | + |
| 19 | 85 | + |
| 30 | 125 | ++ |
| 33 | 134 | ++ |
| 35 | 107 | ++ |
| 37 | 106 | ++ |

Reported yield values correspond to:
++ = >1.8 mg/ml RNA yield
+ = 1 to 1.8 ug/ul RNA yield

Example 7

Determination of T7RNAP Variant Transcription Fidelity

Polymerase fidelity was measured based on directly sequencing a large number of RT-PCR clones derived from mRNA transcribed from variant polymerases. In vitro transcription reactions were performed as described in Example 4, using 0.5 mM m7G(5')ppp(5')m7G, 5.5 mM GTP, and omitting glucosamine-6-phosphate. The inclusion of m7G (5')ppp(5')m7G allowed the measurement of the contribution of this cap analog (if any) to the error rate of WT and variant polymerases under process-relevant conditions. A 1.7 kb luciferase template DNA (SEQ ID NO: 8) served as a DNA template for transcription using wild-type and variant T7 RNAPs to generate full-length mRNA transcripts. RNA was isolated using the Zymo RNA Clean and concentrator-25 kit (Zymo Research), and residual DNA was removed from the RNA samples by two successive treatments with the DNA-free DNAase I kit (Ambion/Thermo Fisher). Samples were reverse-transcribed with Accuprime Reverse Transcriptase (Agilent) using an oligo-(dT)$_{25}$ primer (SEQ ID NO: 40) annealing to the poly(A) tail on the luciferase template. The RT reaction was then amplified using PHUSION® high-fidelity DNA polymerase using HF buffer (New England Biolabs) via PCR to generate a 1675-bp amplicon, using gene-specific primers (SEQ ID NO: 12, SEQ ID NO:13) annealing to the luciferase coding sequence. Amplified fragments were digested with BglI (New England Biolabs), ligated into a cloning vector, and transformed to generate single clones in *E. coli*.

Individual clones were picked and sequenced using a multiplex barcoding strategy on the Ion Torrent PGM platform (Thermo Fisher). Barcoded reads were deconvoluted, and sequences of individual clones were then assembled against the expected template sequences for the 1632-bp region between SEQ ID NO: 12 and SEQ ID NO: 13. Mutations including small insertion, deletions (i.e., indels), and single-nucleotide polymorphisms were tallied. Most mutations observed were substitutions, although insertions and deletions were also observed. The total number of mutations per base of sequenced mRNA-derived clones was calculated, and is reported in Tables 7.1 and 7.2. The expected overall rate of mutations per base based on the literature is the sum of errors due to the T7RNAP ($1\times10^{-4}$) (Huang et al., Biochem., 39:11571-11580 [2000]), Accuscript reverse transcriptase ($6\times10$-5) (Agilent; See, product literature), and Phusion DNA polymerase ($1.2\times10$-5) (20 cycles; See, NEB product literature), or $1.72\times10^{-4}$ overall. Most variant polymerases demonstrated overall error rates near the reported literature value for T7RNAP, even in the presence of 0.5 mM m7G(5')ppp(5')m7G.

A one-tailed (right-side) binomial test was used to calculate the probability of sampling the observed number of errors (or greater) given number of bases sequenced if the actual error rate in the experiment is equal to the observed overall error rate for T7RNAP-WT in the separate experiments presented in Tables 7.1 and 7.2. The fidelity of a given variant was considered indistinguishable from the WT T7RNAP in this assay for p values greater than 0.05. In Table 7.1, "+" is less than $1.7*10^{-4}$, and "−" is greater than $1.7*10^{-4}$ in the observed error rate result column, while "+" is p>0.05 and "−" is 0<0.05 in the binomial test result column. In Table 7.2, "+" is less than $1.5\times10^{-4}$ and "−" is greater than $1.5\times10^{-4}$ in the observed error rate result column, while "+" is p>0.05 and "−" is p<0.05 in the binomial test result column.

TABLE 7.1

Error Rates for Some T7RNAP Variants

| SEQ ID NO: | Variant ID NO: | Observed Error Rate | Binomial Test |
|---|---|---|---|
| 4 | N/A | + | + |
| 15 | 26 | + | + |
| 17 | 86 | + | + |
| 19 | 85 | + | − |
| 21 | 87 | + | + |
| 23 | 93 | − | − |
| 25 | 95 | + | + |
| 27 | 88 | + | + |

TABLE 7.2

Error Rates for Some T7RNAP Variants

| SEQ ID NO: | Variant ID NO: | Observed Error Rate | Binomial Test |
|---|---|---|---|
| 4 | N/A | + | + |
| 29 | 108 | + | + |
| 31 | 125 | − | − |
| 33 | 134 | + | + |
| 35 | 107 | + | + |
| 37 | 106 | + | + |
| 39 | 133 | + | − |

While the invention has been described with reference to the specific embodiments, various changes can be made and equivalents can be substituted to adapt to a particular situation, material, composition of matter, process, process step or steps, thereby achieving benefits of the invention without departing from the scope of what is claimed.

For all purposes in the United States of America, each and every publication and patent document cited in this application is incorporated herein by reference as if each such publication or document was specifically and individually indicated to be incorporated herein by reference. Citation of publications and patent documents is not intended as an indication that any such document is pertinent prior art, nor does it constitute an admission as to its contents or date.

What is claimed is:

1. An engineered polynucleotide sequence encoding at least one engineered RNA polymerase, wherein said polymerase utilizes a cap or cap analog during transcription initiation, and wherein said engineered RNA polymerase comprises a polypeptide sequence having at least 95% sequence identity to SEQ ID NO: 15 and further comprises a substitution at position 404, wherein said position is numbered with reference to SEQ ID NO: 15, and wherein said engineered RNA polymerase exhibits improved selectivity for cap analog relative to GTP during transcription initiation.

2. The engineered polynucleotide sequence encoding said RNA polymerase of claim 1, wherein said RNA polymerase preferentially utilizes a cap or cap analog during transcription initiation.

3. The engineered polynucleotide sequence encoding said RNA polymerase of claim 1, wherein said RNA polymerase does not utilize a cap or cap analog during transcription elongation.

4. The engineered polynucleotide sequence encoding said RNA polymerase of claim 1, wherein said engineered RNA polymerase is an engineered T7 RNA polymerase.

5. The engineered polynucleotide sequence encoding said engineered RNA polymerase of claim 1, wherein said polypeptide sequence further comprises a substitution set selected from 113/137/513, 136/357/404/514, 136/357/514, 136/394/404/446, 136/401, 136/401/404, 136/404/446, 136/404/514, 136/446, 136/514, 137, 137/401, 137/401/513, 137/401/513, 137/513, 137/513/621, 137/635, 137/656, 357/394/401/404/514, 357/394/446/514, 357/514, 394/446/514, 401/404, 401/404/514, 401/513/635, 401/635, 513/635, 513/635/656, 513/660, 635/656, 635/660, and 660, and/or any combinations thereof, wherein the amino acid positions are numbered with reference to SEQ ID NO: 15.

6. The engineered polynucleotide sequence encoding said RNA polymerase of claim 1, wherein said engineered RNA polymerase comprises a polypeptide sequence that is at least 95%, 96%, 97%, 98%, 99% or more identical to the sequence of at least one engineered RNA polymerase variant set forth in SEQ ID NO: 29, 31, 35, or 37.

7. The engineered polynucleotide sequence encoding said RNA polymerase of claim 1, wherein said engineered RNA polymerase exhibits at least one additional improved property selected from improved protein expression, improved stability in storage buffer, and improved stability under reaction conditions.

8. The engineered polynucleotide sequence encoding said RNA polymerase of claim 1, wherein the polymerase maintains RNA yield, transcription fidelity, thermostability, protein expression, stability at −20° C., or stability in reaction conditions equivalent to the wild-type T7 RNA polymerase.

9. The engineered polynucleotide sequence encoding said RNA polymerase of claim 1, wherein said RNA polymerase generates greater than about 80%, 85%, 90%, 91%, 92%, 93%, 94%, 95%, 96%, 97%, 98%, 99%, or more capped RNA transcripts relative to uncapped transcripts.

10. The engineered polynucleotide sequence encoding said RNA polymerase of claim 8, wherein said RNA polymerase generates greater than 90% capped RNA transcripts relative to uncapped transcripts.

11. The engineered polynucleotide sequence encoding said RNA polymerase of claim 1, wherein said engineered polymerase is purified.

12. The engineered polynucleotide sequence encoding said RNA polymerase of claim 1, wherein said engineered polynucleotide is purified.

13. The engineered polynucleotide sequence of claim 1, wherein said polynucleotide sequence is operably linked to a control sequence.

14. The engineered polynucleotide sequence of claim 1, wherein said polynucleotide sequence is codon optimized.

15. An expression vector comprising at least one polynucleotide sequence of claim 13.

16. An expression vector comprising at least one polynucleotide sequence of claim 14.

17. A host cell comprising at least one expression vector of claim 15.

18. A host cell comprising at least one expression vector of claim 16.

19. A method of producing an engineered RNA polymerase in a host cell, comprising culturing the host cell of claim 17, under suitable cultures conditions, such that at least one engineered RNA polymerase is produced.

20. The method of claim 19, further comprising recovering at least one engineered RNA polymerase from the culture and/or host cell.

21. The method of claim 20, further comprising the step of purifying said at least one engineered RNA polymerase.

22. A method of producing an engineered RNA polymerase in a host cell, comprising culturing the host cell of claim 18, under suitable culture conditions, such that at least one engineered RNA polymerase is produced.

23. The method of claim 22, further comprising recovering at least one engineered RNA polymerase from the culture and/or host cell.

24. The method of claim 23, further comprising the step of purifying said at least one engineered RNA polymerase.

25. The engineered polynucleotide sequence of claim 1, wherein said engineered RNA polymerase comprises a polypeptide sequence having at least 96%, 97%, 98%, or 99% sequence identity to SEQ ID NO: 15.

* * * * *